US012544387B2

(12) United States Patent
Sepah

(10) Patent No.: US 12,544,387 B2
(45) Date of Patent: *Feb. 10, 2026

(54) METHODS AND COMPOSITIONS FOR TESTOSTERONE PRODUCTION

(71) Applicant: Saviz Cameron Sepah, Santa Monica, CA (US)

(72) Inventor: Saviz Cameron Sepah, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/230,961

(22) Filed: Jun. 6, 2025

(65) Prior Publication Data

US 2025/0295670 A1 Sep. 25, 2025

Related U.S. Application Data

(63) Continuation of application No. 19/199,292, filed on May 5, 2025, now abandoned, which is a continuation-in-part of application No. 19/025,668, filed on Jan. 16, 2025, now Pat. No. 12,318,397, which is a continuation of application No. 18/664,867, filed on May 15, 2024, now Pat. No. 12,290,524.

(Continued)

(51) Int. Cl.

| | |
|---|---|
| ***A61K 31/568*** | (2006.01) |
| ***A61K 9/00*** | (2006.01) |
| ***A61K 31/138*** | (2006.01) |
| ***A61K 31/573*** | (2006.01) |
| ***A61K 47/12*** | (2006.01) |
| ***A61K 47/38*** | (2006.01) |
| ***A61K 47/44*** | (2017.01) |
| ***A61P 5/26*** | (2006.01) |

(52) U.S. Cl.

CPC .......... *A61K 31/568* (2013.01); *A61K 9/0053* (2013.01); *A61K 9/006* (2013.01); *A61K 31/138* (2013.01); *A61K 31/573* (2013.01); *A61K 47/12* (2013.01); *A61K 47/38* (2013.01); *A61K 47/44* (2013.01); *A61P 5/26* (2018.01)

(58) Field of Classification Search

CPC ........ A61K 31/568; A61K 9/0053; A61P 5/26

See application file for complete search history.

(56) References Cited

U.S. PATENT DOCUMENTS

| | | | | |
|---|---|---|---|---|
| 12,290,524 | B1 * | 5/2025 | Sepah .................. | A61K 31/138 |
| 12,318,397 | B1 * | 6/2025 | Sepah .................. | A61K 31/573 |

(Continued)

OTHER PUBLICATIONS

Final Office Action for U.S. Appl. No. 18/664,846, mailed Dec. 20, 2024, 11 pages.

Non-Final Office Action for U.S. Appl. No. 18/664,846, mailed Aug. 12, 2024, 11 pages.

Non-Final Office Action for U.S. Appl. No. 18/664,867, mailed Sep. 20, 2024, 5 pages.

Non-Final Office Action for U.S. Appl. No. 19/025,668, mailed Mar. 18, 2025, 7 pages.

Non-Final Office Action for U.S. Appl. No. 19/216,474, mailed Aug. 15, 2025, 6 pages.

(Continued)

*Primary Examiner* — Carlos A Azpuru

(74) *Attorney, Agent, or Firm* — Sterne, Kessler, Goldstein & Fox P.L.L.C.

(57) ABSTRACT

The present disclosure provides a pharmaceutical composition that includes enclomiphene and pregnenolone, and pharmaceutical combinations and uses thereof. The present disclosure also provides a pharmaceutical combination that includes a selective estrogen receptor modulator and testosterone in a form suitable for oral administration, sublingual administration, topical administration, transdermal administration, or combinations thereof and uses thereof.

29 Claims, 33 Drawing Sheets

Related U.S. Application Data

(60) Provisional application No. 63/615,679, filed on Dec. 28, 2023.

(56) References Cited

U.S. PATENT DOCUMENTS

| | | | |
|---|---|---|---|
| 2015/0031656 | A1 | 1/2015 | Podoloski et al. |
| 2025/0213589 | A1 | 7/2025 | Sepah |
| 2025/0241929 | A1 | 7/2025 | Sepah |
| 2025/0262224 | A1 | 8/2025 | Sepah |
| 2025/0268915 | A1 | 8/2025 | Sepah |
| 2025/0281505 | A1 | 9/2025 | Sepah |
| 2025/0288598 | A1 | 9/2025 | Sepah |

OTHER PUBLICATIONS

Non-Final Office Action for U.S. Appl. No. 19/224,452, mailed on Jul. 31, 2025, 7 Pages.
Notice of Allowance for U.S. Appl. No. 18/664,867, mailed Mar. 17, 2025, 8 Pages.
Notice of Allowance for U.S. Appl. No. 19/025,668, mailed Apr. 25, 2025, 4 Pages.

* cited by examiner

METHODS AND COMPOSITIONS FOR TESTOSTERONE PRODUCTION

BACKGROUND

Testosterone Replacement Therapy (TRT) is a widely used treatment for men with low testosterone levels and symptomatic hypogonadism. But despite its promise as a frontline therapy, TRT affects endogenous hormone production by the hypothalamus, pituitary gland, adrenal glands, and gonads, including, but not limited to affecting the production of gonadotropins (e.g., luteinizing hormone (LH) and follicle stimulating hormone (FSH)), neurosteroids (e.g., pregnenolone, allopregnanolone, progesterone, dehydroepiandrosterone), and endogenous testosterone. For example, during TRT, endogenous testosterone release can be inhibited through feedback inhibition of pituitary LH. Likewise, spermatogenesis can be suppressed through feedback inhibition of pituitary FSH, thereby impairing sperm production and fertility.

Therefore, there is a need for TRTs that increase the levels of testosterone without altering endogenous hormone production by the hypothalamus, pituitary gland, adrenal glands, and gonads.

BRIEF SUMMARY

The present disclosure is directed to a pharmaceutical composition for stimulating endogenous testosterone production comprising a therapeutically effective amount of a selective estrogen receptor modulator (SERM) and a therapeutically effective amount of a neurosteroid. In some aspects, the pharmaceutical composition can comprise a therapeutically effective amount of enclomiphene and a therapeutically effective amount of pregnenolone.

In some aspects, the pharmaceutical composition can be formulated for sublingual administration. In some aspects, the pharmaceutical composition can be in the form of a sublingual tablet. In some aspects, the composition can comprise (i) about 1 mg to about 80 mg of enclomiphene; and (ii) about 1 mg to about 60 mg of pregnenolone.

In some aspects, the composition can comprise about 1.5 mg to about 50 mg of enclomiphene. In some aspects, the composition can comprise about 2 mg to about 40 mg of pregnenolone. In some aspects, the composition can comprise about 3.125 mg of enclomiphene. In some aspects, the composition can comprise about 6.25 mg of enclomiphene. In some aspects, the composition can comprise about 12.5 mg of enclomiphene. In some aspects, the composition can comprise about 25 mg of enclomiphene. In some aspects, the composition can comprise about 50 mg of enclomiphene. In some aspects, the composition can comprise about 5 mg of pregnenolone. In some aspects, the composition can comprise about 10 mg of pregnenolone. In some aspects, the composition can comprise about 20 mg of pregnenolone. In some aspects, the composition can comprise about 40 mg of pregnenolone.

In some aspects, the composition can comprise a filler. In some aspects, the filler can comprise cellulose.

In some aspects, the composition can comprise a sweetener. In some aspects, the sweetener can be a non-nutritive sweetener. In some aspects, the non-nutritive sweetener can comprise a mixture of steviol glycosides.

In some aspects, the composition can comprise a flavoring agent. In some aspects, the flavoring agent can be an orange flavoring agent.

In some aspects, the composition can comprise a lubricant. In some aspects, the lubricant can be magnesium stearate.

The present disclosure also discloses a pharmaceutical combination comprising the pharmaceutical composition described herein and a second composition comprising testosterone in a form suitable for oral administration.

In some aspects, the second composition comprising testosterone in a form suitable for oral administration can be a tablet or capsule that can comprise a lipid bilayer. In some aspects, the second composition comprising testosterone in a form suitable for oral administration can be a tablet or capsule suitable for lymphatic absorption.

In some aspects, the second composition can comprise about 100 mg to about 1,500 mg of testosterone. In some aspects, the second composition can comprise about 200 mg to about 1,200 mg of testosterone. In some aspects, the second composition can comprise about 200 mg of testosterone. In some aspects, the second composition can comprise about 200 mg of testosterone. In some aspects, the second composition can comprise about 400 mg of testosterone. In some aspects, the second composition can comprise about 600 mg of testosterone. In some aspects, the second composition can comprise about 800 mg of testosterone. In some aspects, the second composition can comprise about 1,000 mg of testosterone. In some aspects, the second composition can comprise about 1,200 mg of testosterone.

In some aspects, the second composition can comprise an oil. In some aspects, the oil can comprise safflower oil.

In some aspects, the second composition can comprise a filler. In some aspects, the filler can comprise cellulose.

In some aspects, the second composition can comprise a lubricant. In some aspects, the lubricant can be magnesium stearate.

Also disclosed herein is a pharmaceutical combination comprising (i) a first composition comprising a selective estrogen receptor modulator, and (ii) a second composition comprising testosterone in a form suitable for oral administration. In some aspects, the selective estrogen receptor modulator can be selected from the group consisting of clomiphene, enclomiphene, toremifene, acolbifene, lasoxifene, bazedoxifene, tamoxifen, droloxifene, raloxifene, metabolites thereof, and pharmaceutically acceptable salts or solvates thereof. In some aspects, the selective estrogen receptor modulator can be enclomiphene.

In some aspects, the first composition can comprise about 1 mg to about 80 mg of enclomiphene. In some aspects, the first composition can comprise about 1.5 mg to about 50 mg of enclomiphene.

In some aspects, the first composition can further comprise a neurosteroid. In some aspects, the neurosteroid can be selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof. In some aspects, the neurosteroid can be pregnenolone.

In some aspects, the first composition can comprise about 1 mg to about 60 mg of pregnenolone. In some aspects, the first composition can comprise about 2 mg to about 40 mg of pregnenolone.

In some aspects, the first composition can be in a form suitable for sublingual administration. In some aspects, the first composition can be a sublingual tablet.

In some aspects, the second composition comprising testosterone can be a tablet or capsule comprising a lipid bilayer.

In some aspects, the second composition comprising testosterone can be a tablet or capsule suitable for lymphatic absorption.

In some aspects, the second composition can comprise about 100 mg to about 1,500 mg of testosterone. In some aspects, the second composition can comprise about 200 mg to about 1,200 mg of testosterone. In some aspects, the second composition can comprise about 200 mg of testosterone. In some aspects, the second composition can comprise about 200 mg of testosterone. In some aspects, the second composition can comprise about 400 mg of testosterone. In some aspects, the second composition can comprise about 600 mg of testosterone. In some aspects, the second composition can comprise about 800 mg of testosterone. In some aspects, the second composition can comprise about 1,000 mg of testosterone. In some aspects, the second composition can comprise about 1,200 mg of testosterone.

In some aspects, the pharmaceutical combination can further comprise a 5α-reductase inhibitor.

In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects, the 5α-reductase inhibitor can be dutasteride. In some aspects, the 5α-reductase inhibitor can be finasteride.

In some aspects, the pharmaceutical combination can further comprise an aromatase inhibitor.

In some aspects, the aromatase inhibitor can be selected from the group consisting of atamestane, exemestane, and formestane, and non-steroids, such as aminoglutethimide, roglethimide, pyridoglutethimide, trilostane, testolactone, vorozole, fadrozole, anastrozole, letrozole, and combinations thereof. In some aspects, the aromatase inhibitor can be anastrozole. In some aspects, the aromatase inhibitor can be exemestane.

Also described herein are methods for increasing testosterone levels in a subject in need thereof. In some aspects, the method can comprise administering the pharmaceutical composition described herein or the pharmaceutical combination described herein.

In some aspects, a method of increasing testosterone levels in a subject in need thereof, can comprise:

(i) administering to the subject an oral or sublingual tablet or capsule comprising about 5 mg to about 80 mg of enclomiphene citrate, clomiphene citrate, or toremifene citrate; and (ii) topically administering to the subject about 50 mg to about 400 mg of testosterone base or testosterone ester.

In some aspects, administering the oral or sublingual tablet or capsule and topically administering testosterone base or testosterone ester can maintain a subject's LH level and FSH level at about 1 IU/L or more, or can increase a subject's LH level and FSH level to about 1 IU/L or more.

In some aspects, administering the oral or sublingual tablet or capsule and topically administering testosterone base or testosterone ester can maintain testicular function, size, and volume and reduce risk of testicular shrinkage, impaired fertility, and dependence.

In some aspects of the method herein, the oral or sublingual tablet or capsule can be a sublingual tablet.

In some aspects of the method herein, the oral or sublingual tablet or capsule can comprise enclomiphene citrate.

In some aspects of the method herein, the oral or sublingual tablet or capsule can comprise about 5 mg to about 80 mg of enclomiphene citrate.

In some aspects of the method herein, the oral or sublingual tablet or capsule can comprise about 6.25 mg, about 12.5 mg, about 25 mg, or about 50 mg of the enclomiphene citrate.

In some aspects of the method herein, the oral or sublingual tablet or capsule can comprise clomiphene citrate.

In some aspects of the method herein, the oral or sublingual tablet or capsule can comprise about 5 mg to about 80 mg of clomiphene citrate.

In some aspects of the method herein, the oral or sublingual tablet or capsule can comprise toremifene citrate.

In some aspects of the method herein, the oral or sublingual tablet or capsule can comprise about 5 mg to about 120 mg of toremifene citrate.

In some aspects of the method herein, the subject can be topically administered about 50 mg to about 250 mg of testosterone base or testosterone ester.

In some aspects of the method herein, the oral or sublingual tablet or capsule can further comprise a neurosteroid.

In some aspects of the method herein, the neurosteroid can be pregnenolone.

In some aspects of the method herein, the oral or sublingual tablet or capsule can comprise about 1 mg to about 40 mg of pregnenolone.

In some aspects of the method herein, the oral or sublingual tablet or capsule can further comprise cellulose, a non-nutritive sweetener, a flavoring agent, and magnesium stearate.

In some aspects of the method herein, the subject can be a human subject and administering the oral or sublingual tablet or capsule and topically administering testosterone base or testosterone ester can increase the subject's total testosterone level by at least about 50% compared to the subject's baseline total testosterone level.

Also disclosed herein is a method of increasing testosterone levels in a subject in need thereof, that can comprise administering to the subject:

(i) about 5 mg to about 250 mg of enclomiphene citrate, clomiphene citrate, or toremifene citrate; and (ii) about 50 mg to about 400 mg of testosterone base or testosterone ester, wherein at least the testosterone base or testosterone ester can be administered topically or transdermally.

In some aspects, administering enclomiphene citrate, clomiphene citrate, or toremifene citrate and testosterone base or testosterone ester can maintain a subject's LH level and FSH level at about 1 IU/L or more, or can increase the subject's LH level and FSH level to about 1 IU/L or more.

In some aspects, administering enclomiphene citrate, clomiphene citrate, or toremifene citrate and testosterone base or testosterone ester can maintain testicular function, size, and volume and reduce risk of testicular shrinkage, impaired fertility, and dependence.

In some aspects of the method herein, the subject can be topically administered testosterone base or testosterone ester.

In some aspects of the method herein, the subject can be topically administered about 100 mg to about 400 mg of testosterone base or testosterone ester daily.

In some aspects of the methods herein, the subject can be topically administered about 100 mg to about 200 mg of testosterone base or testosterone ester daily.

In some aspects of the methods herein, the subject can be topically administered enclomiphene citrate.

In some aspects of the methods herein, the subject can be topically administered about 5 mg to about 150 mg per day of enclomiphene citrate.

In some aspects of the methods herein, the subject can be topically administered clomiphene citrate.

In some aspects of the methods herein, the subject can be topically administered about 5 mg to about 150 mg per day of clomiphene citrate.

In some aspects of the methods herein, the subject can be topically administered toremifene citrate.

In some aspects of the methods herein, the subject can be topically administered about 5 mg to about 240 mg per day of toremifene citrate.

In some aspects of the methods herein, the enclomiphene citrate, clomiphene citrate, or toremifene citrate can be administered orally or sublingually.

In some aspects of the methods herein, the subject can be transdermally administered testosterone base or testosterone ester.

In some aspects of the methods herein, the subject can be transdermally administered enclomiphene citrate, clomiphene citrate, or toremifene citrate.

In some aspects of the methods herein, the subject can be transdermally administered enclomiphene citrate.

In some aspects of the methods herein, the enclomiphene citrate, clomiphene citrate, or toremifene citrate can be administered as a first topical or transdermal composition and the testosterone can be administered as a second topical or transdermal composition.

In some aspects of the methods herein, the enclomiphene citrate, clomiphene citrate, or toremifene citrate and the testosterone can be administered as a topical or transdermal composition.

In some aspects of the methods herein, the enclomiphene citrate, clomiphene citrate, or toremifene citrate and the testosterone can be administered by a transdermal patch.

In some aspects of the methods herein, the subject is a human subject and administering the therapeutically effective amount of enclomiphene citrate, clomiphene citrate, or toremifene citrate and the therapeutically effective amount of testosterone base or testosterone ester can increase the subject's total testosterone level by at least about 50% compared to the subject's baseline total testosterone level.

DETAILED DESCRIPTION

Figure 1:
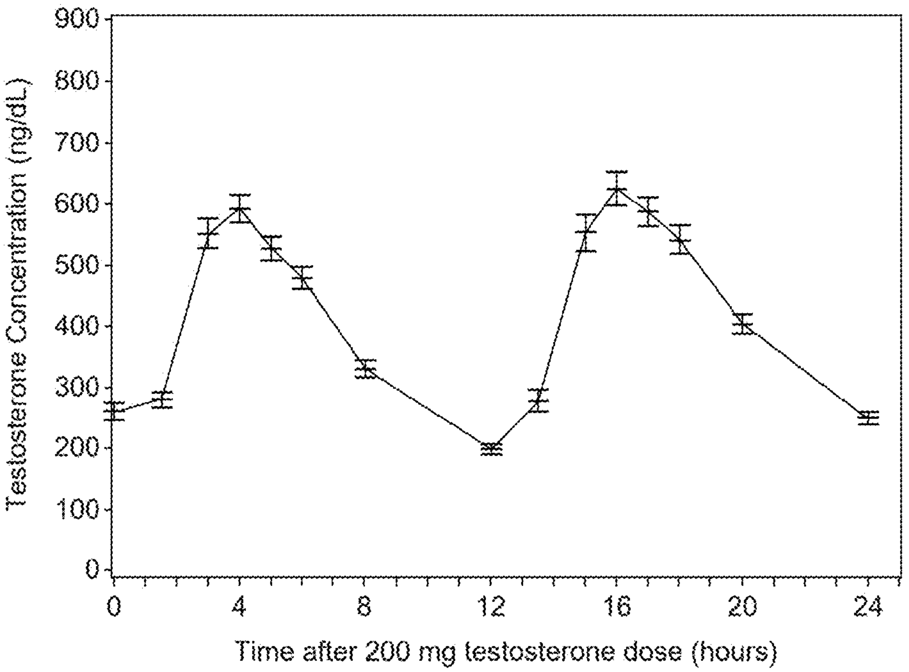
FIG. 1 is a phase diagram of the testosterone concentration in a patient at various time points after being administered 200 mg of testosterone.

The present disclosure is directed to a pharmaceutical composition comprising a therapeutically effective amount of a selective estrogen receptor modulator (SERM) and a therapeutically effective amount of a neurosteroid. Without wishing to be bound by any particular theory, it is believed that the administration of a composition that comprises therapeutically effective amounts of a SERM and a neurosteroid can increase the production of endogenous testosterone (i.e., at least partially reduce the suppression of endogenous testosterone when a subject is on TRT) and maintain baseline levels of LH and FSH production when a subject is also on TRT.

In some embodiments, the pharmaceutical composition comprises a therapeutically effective amount of enclomiphene, or an equivalent amount of a pharmaceutically acceptable salt thereof, and a therapeutically effective amount of pregnenolone. The chemical structure of enclomiphene is provided below:

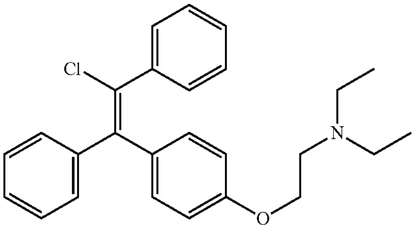 [SMILES: CCN(CC)CCOc1ccc(/C(=C(/Cl)c2ccccc2)c2ccccc2)cc1]

The chemical structure of pregnenolone is provided below:

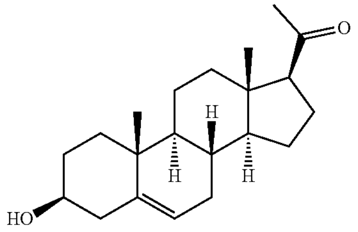

The present disclosure is also directed to a pharmaceutical combination comprising the pharmaceutical composition comprising a therapeutically effective amount of the selective estrogen receptor modulator (SERM) and a therapeutically effective amount of the neurosteroid, and a second composition comprising testosterone in a form suitable for oral or topical or transdermal administration. The chemical structure of testosterone is provided below:

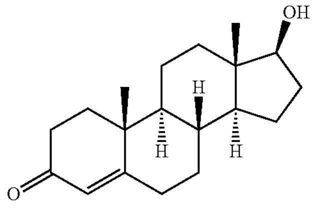

Without wishing to be bound by any particular theory, it is believed that the co-administration of a first composition that comprises therapeutically effective amounts of the SERM and the neurosteroid and a second composition that comprises testosterone in a form suitable for oral or topical or transdermal administration can increase testosterone levels in a subject (i.e., at least partially reduce the suppression of endogenous testosterone when a subject is on TRT) and maintain baseline levels of LH and FSH production when a subject is on TRT.

The present disclosure is further directed to a method of increasing testosterone levels in a subject in need thereof comprising administering the pharmaceutical composition or the pharmaceutical combination described herein.

Definitions

The singular forms "a," "an," and "the" include plural referents unless the context clearly dictates otherwise.

As used herein, the term "or" is a logical disjunction (i.e., and/or) and does not indicate an exclusive disjunction unless expressly indicated as such with the terms "either," "unless," "alternatively," and words of similar effect.

As used herein, the term "about" refers to ±5% of the noted value, unless otherwise specified, and unless the upper bound of the range would exceed 100% of the composition, in which case the upper limit of the range is limited to 99.9%. Thus, and by way of example only, a composition including about 10 weight percent of a given ingredient could have from 9.5 to 10.5 weight percent of the compound. Similarly, a composition including about 95 weight percent of a given ingredient could have from 90.25 to 99.9 weight percent of the ingredient in the composition.

As used herein, "administration" and "administering" may be used interchangeably, and refer to the act of presenting, applying, or introducing a compound or formulation to a subject in order to achieve a desired physiological or psychological response.

As used herein, "co-administration" and "co-administering" may be used interchangeably, and refer to the act of presenting, applying, or introducing at least two compounds or formulations to a subject in order to achieve a desired physiological or psychological response.

As used herein, a "selective estrogen receptor modulator" or "SERM" includes any compound that either directly or through its active metabolite functions as an estrogen receptor antagonist ("antiestrogen"). Non-steroidal compounds that can function as SERMs include, but are not limited to, clomiphene, enclomiphene, tamoxifen, toremifene, acolbifene, lasoxifene, bazedoxifene, droloxifene, raloxifene, metabolites thereof, and pharmaceutically acceptable salts of any of the foregoing.

As used herein, a "neurosteroid" includes any steroid synthesized within the central nervous system and peripheral tissues that can modulate neuronal excitability. Examples of neurosteroids include, but are not limited to, 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof.

As used herein, "testosterone" refers to 17β-hydroxy-4-androsten-3-one and 17β-hydroxy-8α-4-androsten-3-one, as well as its isomers and derivatives, including but not limited to, testosterone cypionate, testosterone phenylacetate, testosterone enanthate, testosterone acetate, testosterone buciclate, testosterone heptanoate, testosterone decanoate, testosterone caprate, testosterone isocaprate, and testosterone undecanoate.

Pharmaceutical Compositions

In one aspect, the present disclosure provides a pharmaceutical composition comprising a therapeutically effective amount of a selective estrogen receptor modulator (SERM) and a therapeutically effective amount of a steroid hormone. In some aspects, the steroid hormone is selected from the group consisting of a neurosteroid, dehydroepiandrosterone (DHEA), estrogen, dihydrotestosterone (DHT), and combinations thereof. In some aspects, the steroid hormone is a neurosteroid. In some aspects, the pharmaceutical composition can be suitable for oral administration. In some aspects, the pharmaceutical composition can be suitable for sublingual administration.

In some aspects, the SERM can be selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof.

In some aspects, the SERM can be enclomiphene or a pharmaceutically acceptable salt or solvate thereof. In some aspects, the pharmaceutically acceptable salt of enclomiphene can be enclomiphene citrate.

In some aspects, the SERM can be toremifene or a pharmaceutically acceptable salt or solvate thereof. In some aspects, the pharmaceutically acceptable salt of toremifene can be toremifene citrate.

In some aspects, the composition can comprise about 1 mg to about 80 mg of the SERM, or an equivalent amount of a pharmaceutically acceptable salt thereof. In some aspects, the composition can comprise about 1 mg to about 70 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of the SERM, or an equivalent amount of a pharmaceutically acceptable salt thereof.

In some aspects, the composition can comprise about 1.5 mg to about 50 mg of the SERM, or an equivalent amount of a pharmaceutically acceptable salt thereof. In some aspects, the composition can comprise about 1.5 mg to about 40 mg, about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of the SERM, or an equivalent amount of a pharmaceutically acceptable salt thereof.

In some aspects, the composition can comprise about 2 mg to about 50 mg of the SERM, or an equivalent amount of a pharmaceutically acceptable salt thereof. In some aspects, the composition can comprise about 2 mg to about 40 mg, about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of the SERM, or an equivalent amount of a pharmaceutically acceptable salt thereof.

In some aspects, the composition can comprise about 2.5 mg to about 50 mg of the SERM, or an equivalent amount of a pharmaceutically acceptable salt thereof. In some aspects, the composition can comprise about 2.5 mg to about 40 mg, about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of the SERM, or an equivalent amount of a pharmaceutically acceptable salt thereof.

In some aspects, the composition can comprise about 3 mg to about 50 mg of the SERM, or an equivalent amount of a pharmaceutically acceptable salt thereof. In some aspects, the composition can comprise about 3 mg to about 40 mg, about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of the SERM, or an equivalent amount of a pharmaceutically acceptable salt thereof.

In some aspects, the composition can comprise about 4 mg to about 50 mg of the SERM, or an equivalent amount of a pharmaceutically acceptable salt thereof. In some aspects, the composition can comprise about 4 mg to about 40 mg, about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of the SERM, or an equivalent amount of a pharmaceutically acceptable salt thereof.

In some aspects, the composition can comprise about 5 mg to about 50 mg of the SERM, or an equivalent amount of a pharmaceutically acceptable salt thereof. In some aspects, the composition can comprise about 5 mg to about 40 mg, about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, about 5 mg to about 5.5, about 5.5 mg to about 7.5 mg, about 5.5 mg to about 7 mg, about 5.5 to about 6.5 mg, about 5.5 to about 6 mg, about 6 mg to about 8 mg, about 6 mg to about 7.5 mg, about 6 mg to about 7 mg, or about 6 mg to about 6.5 mg of the SERM, or an equivalent amount of a pharmaceutically acceptable salt thereof.

In some aspects, the composition can comprise about 8 mg to about 50 mg of the SERM, or an equivalent amount of a pharmaceutically acceptable salt thereof. In some aspects, the composition can comprise about 8 mg to about 40 mg, about 8 mg to about 30 mg, about 8 mg to about 25 mg, about 8 mg to about 20 mg, about 8 mg to about 15 mg, about 8 mg to about 14 mg, about 8 mg to about 13 mg, about 8 mg to about 12 mg, about 8 mg to about 11 mg, about 8 mg to about 10 mg, about 8 mg to about 9 mg, about 9 mg to about 15 mg, about 9 mg to about 14 mg, about 9 mg to about 13 mg, about 9 mg to about 12 mg, about 9 mg to about 11 mg, or about 9 mg to about 10 mg of the SERM, or an equivalent amount of a pharmaceutically acceptable salt thereof.

In some aspects, the composition can comprise about 10 mg to about 50 mg of the SERM, or an equivalent amount of a pharmaceutically acceptable salt thereof. In some aspects, the composition can comprise about 10 mg to about 40 mg, about 10 mg to about 30 mg, about 10 mg to about 27.5 mg, about 10 mg to about 25 mg, about 10 mg to about 22.5 mg, about 10 mg to about 20 mg, about 10 mg to about 17.5 mg, about 10 mg to about 15 mg, about 11 mg to about 14 mg, or about 12 mg to about 13 mg of the SERM, or an equivalent amount of a pharmaceutically acceptable salt thereof.

In some aspects, the composition can comprise about 20 mg to about 50 mg of the SERM, or an equivalent amount of a pharmaceutically acceptable salt thereof. In some aspects, the composition can comprise about 20 mg to about 40 mg, about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, or about 20 mg to about 21 mg of the SERM, or an equivalent amount of a pharmaceutically acceptable salt thereof.

In some aspects, the composition can comprise about 22.5 mg to about 50 mg of the SERM, or an equivalent amount of a pharmaceutically acceptable salt thereof. In some aspects, the composition can comprise about 22.5 mg to about 45 mg, about 22.5 mg to about 40 mg, about 22.5 mg to about 35 mg, about 22.5 mg to about 30 mg, about 22.5 mg to about 29 mg, about 22.5 mg to about 28 mg, about 22.5 mg to about 27.5 mg, about 22.5 mg to about 27 mg, about 22.5 mg to about 26.5 mg, about 22.5 mg to about 26 mg, about 22.5 mg to about 25.5 mg, about 22.5 mg to about 25 mg, about 22.5 mg to about 24.5 mg, about 22.5 mg to about 24 mg, about 22.5 mg to about 23.5 mg, about 22.5 to about 23 mg, 23 mg about 27.5 mg, about 23 mg to about 27 mg, about 23 mg to about 26.5 mg, about 23 mg to about 26 mg, about 23 mg to about 25.5 mg, about 23 mg to about 25 mg, about 23 mg to about 23 mg, about 23 mg to about 24 mg, about 23 mg to about 23.5 mg, about 24 mg to about 27.5 mg, about 24 mg to about 27 mg, about 24 mg to about 26.5 mg, about 24 mg to about 26 mg, about 24 mg to about 25.5 mg, about 24 mg to about 25 mg, or about 24 mg to about 24.5 mg of the SERM, or an equivalent amount of a pharmaceutically acceptable salt thereof.

In some aspects, the composition can comprise about 1 mg, about 1.5 mg, about 2 mg, about 2.5 mg, about 3 mg, about 3.125 mg, about 3.5 mg, about 4 mg, about 4.5 mg, about 5 mg, about 5.5 mg, about 6 mg, about 6.25 mg, about 6.5 mg, about 7 mg, about 7.5 mg, about 8 mg, about 8.5 mg, about 9 mg, about 9.5 mg, about 10 mg, about 12.5 mg, about 15 mg, about 20 mg, about 25 mg, about 30 mg, about 35 mg, about 40 mg, about 45 mg, about 50 mg of the SERM, or an equivalent amount of a pharmaceutically acceptable salt thereof.

In some aspects, the composition can comprise about 1 mg to about 80 mg of enclomiphene, or an equivalent amount of a pharmaceutically acceptable salt thereof. In some aspects, the composition can comprise about 1 mg to about 70 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of enclomiphene, or an equivalent amount of a pharmaceutically acceptable salt thereof.

In some aspects, the composition can comprise about 1.5 mg to about 50 mg of enclomiphene, or an equivalent amount of a pharmaceutically acceptable salt thereof. In some aspects, the composition can comprise about 1.5 mg to about 40 mg, about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of enclomiphene, or an equivalent amount of a pharmaceutically acceptable salt thereof.

In some aspects, the composition can comprise about 2 mg to about 50 mg of enclomiphene, or an equivalent amount of a pharmaceutically acceptable salt thereof. In some aspects, the composition can comprise about 2 mg to about 40 mg, about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of enclomiphene, or an equivalent amount of a pharmaceutically acceptable salt thereof.

In some aspects, the composition can comprise about 2.5 mg to about 50 mg of enclomiphene, or an equivalent amount of a pharmaceutically acceptable salt thereof. In some aspects, the composition can comprise about 2.5 mg to about 40 mg, about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of enclomiphene, or an equivalent amount of a pharmaceutically acceptable salt thereof.

In some aspects, the composition can comprise about 3 mg to about 50 mg of enclomiphene, or an equivalent amount of a pharmaceutically acceptable salt thereof. In some aspects, the composition can comprise about 3 mg to about 40 mg, about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of enclomiphene, or an equivalent amount of a pharmaceutically acceptable salt thereof.

In some aspects, the composition can comprise about 4 mg to about 50 mg of enclomiphene, or an equivalent amount of a pharmaceutically acceptable salt thereof. In some aspects, the composition can comprise about 4 mg to about 40 mg, about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of enclomiphene, or an equivalent amount of a pharmaceutically acceptable salt thereof.

In some aspects, the composition can comprise about 5 mg to about 50 mg of enclomiphene, or an equivalent amount of a pharmaceutically acceptable salt thereof. In some aspects, the composition can comprise about 5 mg to about 40 mg, about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, about 5 mg to about 5.5, about 5.5 mg to about 7.5 mg, about 5.5 mg to about 7 mg, about 5.5 to about 6.5 mg, about 5.5 to about 6 mg, about 6 mg to about 8 mg, about 6 mg to about 7.5 mg, about 6 mg to about 7 mg, or about 6 mg to about 6.5 mg of enclomiphene, or an equivalent amount of a pharmaceutically acceptable salt thereof.

In some aspects, the composition can comprise about 8 mg to about 50 mg of enclomiphene, or an equivalent amount of a pharmaceutically acceptable salt thereof. In some aspects, the composition can comprise about 8 mg to about 40 mg, about 8 mg to about 30 mg, about 8 mg to about 25 mg, about 8 mg to about 20 mg, about 8 mg to about 15 mg, about 8 mg to about 14 mg, about 8 mg to about 13 mg, about 8 mg to about 12 mg, about 8 mg to about 11 mg, about 8 mg to about 10 mg, about 8 mg to about 9 mg, about 9 mg to about 15 mg, about 9 mg to about 14 mg, about 9 mg to about 13 mg, about 9 mg to about 12 mg, about 9 mg to about 11 mg, or about 9 mg to about 10 mg of enclomiphene, or an equivalent amount of a pharmaceutically acceptable salt thereof.

In some aspects, the composition can comprise about 10 mg to about 50 mg of enclomiphene, or an equivalent amount of a pharmaceutically acceptable salt thereof. In some aspects, the composition can comprise about 10 mg to about 40 mg, about 10 mg to about 30 mg, about 10 mg to about 27.5 mg, about 10 mg to about 25 mg, about 10 mg to about 22.5 mg, about 10 mg to about 20 mg, about 10 mg to about 17.5 mg, about 10 mg to about 15 mg, about 11 mg to about 14 mg, or about 12 mg to about 13 mg of enclomiphene, or an equivalent amount of a pharmaceutically acceptable salt thereof.

In some aspects, the composition can comprise about 20 mg to about 50 mg of enclomiphene, or an equivalent amount of a pharmaceutically acceptable salt thereof. In some aspects, the composition can comprise about 20 mg to about 40 mg, about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, or about 20 mg to about 21 mg of enclomiphene, or an equivalent amount of a pharmaceutically acceptable salt thereof.

In some aspects, the composition can comprise about 22.5 mg to about 50 mg of enclomiphene, or an equivalent amount of a pharmaceutically acceptable salt thereof. In some aspects, the composition can comprise about 22.5 mg to about 45 mg, about 22.5 mg to about 40 mg, about 22.5 mg to about 35 mg, about 22.5 mg to about 30 mg, about 22.5 mg to about 29 mg, about 22.5 mg to about 28 mg, about 22.5 mg to about 27.5 mg, about 22.5 mg to about 27 mg, about 22.5 mg to about 26.5 mg, about 22.5 mg to about 26 mg, about 22.5 mg to about 25.5 mg, about 22.5 mg to about 25 mg, about 22.5 mg to about 24.5 mg, about 22.5 mg to about 24 mg, about 22.5 mg to about 23.5 mg, about 22.5 to about 23 mg, 23 mg about 27.5 mg, about 23 mg to about 27 mg, about 23 mg to about 26.5 mg, about 23 mg to about 26 mg, about 23 mg to about 25.5 mg, about 23 mg to about 25 mg, about 23 mg to about 23 mg, about 23 mg to about 24 mg, about 23 mg to about 23.5 mg, about 24 mg to about 27.5 mg, about 24 mg to about 27 mg, about 24 mg to about 26.5 mg, about 24 mg to about 26 mg, about 24 mg to about 25.5 mg, about 24 mg to about 25 mg, or about 24 mg to about 24.5 mg of enclomiphene, or an equivalent amount of a pharmaceutically acceptable salt thereof.

In some aspects, the composition can comprise about 1 mg, about 1.5 mg, about 2 mg, about 2.5 mg, about 3 mg, about 3.125 mg, about 3.5 mg, about 4 mg, about 4.5 mg, about 5 mg, about 5.5 mg, about 6 mg, about 6.25 mg, about 6.5 mg, about 7 mg, about 7.5 mg, about 8 mg, about 8.5 mg, about 9 mg, about 9.5 mg, about 10 mg, about 12.5 mg, about 15 mg, about 20 mg, about 25 mg, about 30 mg, about 35 mg, about 40 mg, about 45 mg, about 50 mg of enclomiphene, or an equivalent amount of a pharmaceutically acceptable salt thereof.

In some aspects, the composition can comprise about 1 mg to about 120 mg of toremifene, or an equivalent amount of a pharmaceutically acceptable salt thereof. In some aspects, the composition can comprise about 1 mg to about 110 mg, about 1 mg to about 100 mg, about 1 mg to about 90 mg, about 1 mg to about 80 mg, about 1 mg to about 70 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of toremifene, or an equivalent amount of a pharmaceutically acceptable salt thereof.

In some aspects, the composition can comprise about 2 mg to about 120 mg of toremifene, or an equivalent amount of a pharmaceutically acceptable salt thereof. In some aspects, the composition can comprise about 2 mg to about 110 mg, about 2 mg to about 100 mg, about 2 mg to about 90 mg, about 2 mg to about 80 mg, about 2 mg to about 70 mg, about 2 mg to about 60 mg, about 2 mg to about 50 mg, about 2 mg to about 40 mg, about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of toremifene, or an equivalent amount of a pharmaceutically acceptable salt thereof.

In some aspects, the composition can comprise about 5 mg to about 120 mg of toremifene, or an equivalent amount of a pharmaceutically acceptable salt thereof. In some aspects, the composition can comprise about 5 mg to about 110 mg, about 5 mg to about 100 mg, about 5 mg to about 90 mg, about 5 mg to about 80 mg, about 5 mg to about 70 mg, about 5 mg to about 60 mg, about 5 mg to about 50 mg, about 5 mg to about 40 mg, about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, about 5 mg to about 5.5, about 5.5 mg to about 7.5 mg, about 5.5 mg to about 7 mg, about 5.5 to about 6.5 mg, about 5.5 to about 6 mg, about 6 mg to about 8 mg, about 6 mg to about 7.5 mg, about 6 mg to about 7 mg, or about 6 mg to about 6.5 mg of toremifene, or an equivalent amount of a pharmaceutically acceptable salt thereof.

In some aspects, the composition can comprise about 10 mg to about 120 mg of toremifene, or an equivalent amount of a pharmaceutically acceptable salt thereof. In some aspects, the composition can comprise about 10 mg to about 110 mg, about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, about 10 mg to about 27.5 mg, about 10 mg to about 25 mg, about 10 mg to about 22.5 mg, about 10 mg to about 20 mg, about 10 mg to about 17.5 mg, about 10 mg to about 15 mg, about 11 mg to about 14 mg, or about 12 mg to about 13 mg of toremifene, or an equivalent amount of a pharmaceutically acceptable salt thereof.

In some aspects, the composition can comprise about 20 mg to about 120 mg of toremifene, or an equivalent amount of a pharmaceutically acceptable salt thereof. In some aspects, the composition can comprise about 20 mg to about 110 mg, about 20 mg to about 100 mg, about 20 mg to about 90 mg, about 20 mg to about 80 mg, about 20 mg to about 70 mg, about 20 mg to about 60 mg, about 20 mg to about 50 mg, about 20 mg to about 40 mg, about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, or about 20 mg to about 21 mg of toremifene, or an equivalent amount of a pharmaceutically acceptable salt thereof.

In some aspects, the composition can comprise about 40 mg to about 120 mg of toremifene, or an equivalent amount of a pharmaceutically acceptable salt thereof. In some aspects, the composition can comprise about 40 mg to about 110 mg, about 40 mg to about 100 mg, about 40 mg to about 90 mg, about 40 mg to about 80 mg, about 40 mg to about 70 mg, about 40 mg to about 60 mg, about 50 mg to about 120 mg, about 50 mg to about 100 mg, about 50 mg to about 90 mg, about 50 mg to about 80 mg, about 50 mg to about 70 mg, or about 60 mg of toremifene, or an equivalent amount of a pharmaceutically acceptable salt thereof.

In some aspects, the composition can comprise about 1 mg, about 1.5 mg, about 2 mg, about 2.5 mg, about 3 mg, about 3.125 mg, about 3.5 mg, about 4 mg, about 4.5 mg, about 5 mg, about 5.5 mg, about 6 mg, about 6.25 mg, about 6.5 mg, about 7 mg, about 7.5 mg, about 8 mg, about 8.5 mg, about 9 mg, about 9.5 mg, about 10 mg, about 12.5 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 110 mg, about 120 mg of toremifene, or an equivalent amount of a pharmaceutically acceptable salt thereof.

In some aspects, the neurosteroid can be selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof. In some aspects, the neurosteroid can be pregnenolone.

In some aspects, the composition can comprise about 1 mg to about 100 mg of the neurosteroid. In some aspects, the composition can comprise about 1 mg to about 80 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of the neurosteroid.

In some aspects, the composition can comprise about 1.5 mg to about 40 mg of the neurosteroid. In some aspects, the composition can comprise about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of the neurosteroid.

In some aspects, the composition can comprise about 2 mg to about 40 mg of the neurosteroid. In some aspects, the composition can comprise about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of the neurosteroid.

In some aspects, the composition can comprise about 2.5 mg to about 40 mg of the neurosteroid. In some aspects, the composition can comprise about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of the neurosteroid.

In some aspects, the composition can comprise about 3 mg to about 40 mg of the neurosteroid. In some aspects, the composition can comprise about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of the neurosteroid.

In some aspects, the composition can comprise about 4 mg to about 40 mg of the neurosteroid. In some aspects, the composition can comprise about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of the neurosteroid.

In some aspects, the composition can comprise about 4.5 mg to about 40 mg of the neurosteroid. In some aspects, the composition can comprise about 4.5 mg to about 30 mg, about 4.5 mg to about 25 mg, about 4.5 mg to about 20 mg, about 4.5 mg to about 17.5 mg, about 4.5 mg to about 15 mg, about 4.5 mg to about 12.5 mg, about 4.5 mg to about 10 mg, about 4.5 mg to about 9 mg, about 4.5 mg to about 8 mg, about 4.5 mg to about 7.5 mg, about 4.5 mg to about 7 mg, about 4.5 mg to about 6.5 mg, about 4.5 mg to about 6 mg, about 4.5 mg to about 5.5 mg, or about 4.5 mg to about 5 mg of the neurosteroid.

In some aspects, the composition can comprise about 5 mg to about 40 mg of the neurosteroid. In some aspects, the composition can comprise about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, or about 5 mg to about 5.5 of the neurosteroid.

In some aspects, the composition can comprise about 8 mg to about 40 mg of the neurosteroid. In some aspects, the composition can comprise about 8 mg to about 30 mg, about 8 mg to about 25 mg, about 8 mg to about 20 mg, about 8 mg to about 17.5 mg, about 8 mg to about 15 mg, about 8 mg to about 12.5 mg, about 8 mg to about 11.5 mg, about 8 mg to about 11 mg, about 8 mg to about 10.5 mg, about 8 mg to about 10 mg, about 8 mg to about 9.5 mg, about 8 mg to about 9 mg, about 9 mg to about 15 mg, about 9 mg to about 12.5 mg, about 9 mg to about 11.5 mg, about 9 mg to about 11 mg, about 9 mg to about 10.5 mg, about 9 mg to about 10 mg, or about 9 mg to about 9.5 mg of the neurosteroid.

In some aspects, the composition can comprise about 10 mg to about 40 mg of the neurosteroid. In some aspects, the composition can comprise about 10 mg to about 30 mg, about 10 mg to about 25 mg, about 10 mg to about 20 mg, about 10 mg to about 17.5 mg, about 10 mg to about 15 mg, about 10 mg to about 12.5 mg, about 10 mg to about 11.5 mg, about 10 mg to about 11 mg, or about 10 mg to about 10.5 mg of the neurosteroid.

In some aspects, the composition can comprise about 12 mg to about 40 mg of the neurosteroid. In some aspects, the composition can comprise about 12 mg to about 30 mg, about 12 mg to about 25 mg, about 12 mg to about 20 mg, about 12 mg to about 17 mg, about 12 mg to about 15 mg, about 12 mg to about 14.5 mg, about 12 mg to about 14 mg, about 12 mg to about 13.5 mg, or about 12 mg to about 13 mg of the neurosteroid.

In some aspects, the composition can comprise about 14 mg to about 40 mg of the neurosteroid. In some aspects, the composition can comprise about 14 mg to about 30 mg, about 14 mg to about 25 mg, about 14 mg to about 20 mg, about 14 mg to about 17.5 mg, about 14 mg to about 16 mg, about 14 mg to about 15.5 mg, about 14 mg to about 15 mg, or about 14 mg to about 14.5 mg of the neurosteroid.

In some aspects, the composition can comprise about 15 mg to about 40 mg of the neurosteroid. In some aspects, the composition can comprise about 15 mg to about 30 mg, about 15 mg to about 27.5 mg, about 15 mg to about 25 mg, about 15 mg to about 22.5 mg, about 15 mg to about 20 mg, about 15 mg to about 17.5 mg, about 15 mg to about 16.5 mg, about 15 mg to about 16 mg, or about 15 mg to about 15.5 mg of the neurosteroid.

In some aspects, the composition can comprise about 17.5 mg to about 40 mg of the neurosteroid. In some aspects, the composition can comprise about 17.5 mg to about 30 mg, about 17.5 mg to about 27.5 mg, about 17.5 mg to about 25 mg, about 17.5 mg to about 22.5 mg, about 17.5 mg to about 20 mg, about 17.5 mg to about 18 mg of the neurosteroid.

In some aspects, the composition can comprise about 20 mg to about 40 mg of the neurosteroid. In some aspects, the composition can comprise about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, about 20 mg to about 21 mg, or about 20 mg to about 20.5 mg of the neurosteroid.

In some aspects, the composition can comprise about 25 mg to about 40 mg of the neurosteroid. In some aspects, the composition can comprise about 25 mg to about 35 mg, about 25 mg to about 30 mg, about 25 mg to about 29 mg, about 25 mg to about 28 mg, about 25 mg to about 27 mg, about 25 mg to about 26.5 mg, about 25 mg to about 26 mg, or about 25 mg to about 25.5 mg of the neurosteroid.

In some aspects, the composition can comprise about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 12.5 mg, about 15 mg, about 17.5 mg, about 20 mg, about 25 mg, about 30 mg, about 35 mg, about 40 mg of the neurosteroid.

In some aspects, the composition can comprise about 1 mg to about 60 mg of pregnenolone. In some aspects, the composition can comprise about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of pregnenolone.

In some aspects, the composition can comprise about 1.5 mg to about 40 mg of pregnenolone. In some aspects, the composition can comprise about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of pregnenolone.

In some aspects, the composition can comprise about 2 mg to about 40 mg of pregnenolone. In some aspects, the composition can comprise about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of pregnenolone.

In some aspects, the composition can comprise about 2.5 mg to about 40 mg of pregnenolone. In some aspects, the composition can comprise about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of pregnenolone.

In some aspects, the composition can comprise about 3 mg to about 40 mg of pregnenolone. In some aspects, the composition can comprise about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of pregnenolone.

In some aspects, the composition can comprise about 4 mg to about 40 mg of pregnenolone. In some aspects, the composition can comprise about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of pregnenolone.

In some aspects, the composition can comprise about 4.5 mg to about 40 mg of pregnenolone. In some aspects, the composition can comprise about 4.5 mg to about 30 mg, about 4.5 mg to about 25 mg, about 4.5 mg to about 20 mg, about 4.5 mg to about 17.5 mg, about 4.5 mg to about 15 mg, about 4.5 mg to about 12.5 mg, about 4.5 mg to about 10 mg, about 4.5 mg to about 9 mg, about 4.5 mg to about 8 mg, about 4.5 mg to about 7.5 mg, about 4.5 mg to about 7 mg, about 4.5 mg to about 6.5 mg, about 4.5 mg to about 6 mg, about 4.5 mg to about 5.5 mg, or about 4.5 mg to about 5 mg of pregnenolone.

In some aspects, the composition can comprise about 5 mg to about 40 mg of pregnenolone. In some aspects, the composition can comprise about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, or about 5 mg to about 5.5 of pregnenolone.

In some aspects, the composition can comprise about 8 mg to about 40 mg of pregnenolone. In some aspects, the composition can comprise about 8 mg to about 30 mg, about 8 mg to about 25 mg, about 8 mg to about 20 mg, about 8 mg to about 17.5 mg, about 8 mg to about 15 mg, about 8 mg to about 12.5 mg, about 8 mg to about 11.5 mg, about 8 mg to about 11 mg, about 8 mg to about 10.5 mg, about 8 mg to about 10 mg, about 8 mg to about 9.5 mg, about 8 mg to about 9 mg, about 9 mg to about 15 mg, about 9 mg to about 12.5 mg, about 9 mg to about 11.5 mg, about 9 mg to about 11 mg, about 9 mg to about 10.5 mg, about 9 mg to about 10 mg, or about 9 mg to about 9.5 mg of pregnenolone.

In some aspects, the composition can comprise about 10 mg to about 40 mg of pregnenolone. In some aspects, the composition can comprise about 10 mg to about 30 mg, about 10 mg to about 25 mg, about 10 mg to about 20 mg, about 10 mg to about 17.5 mg, about 10 mg to about 15 mg, about 10 mg to about 12.5 mg, about 10 mg to about 11.5 mg, about 10 mg to about 11 mg, or about 10 mg to about 10.5 mg of pregnenolone.

In some aspects, the composition can comprise about 12 mg to about 40 mg of pregnenolone. In some aspects, the composition can comprise about 12 mg to about 30 mg, about 12 mg to about 25 mg, about 12 mg to about 20 mg, about 12 mg to about 17 mg, about 12 mg to about 15 mg, about 12 mg to about 14.5 mg, about 12 mg to about 14 mg, about 12 mg to about 13.5 mg, or about 12 mg to about 13 mg of pregnenolone.

In some aspects, the composition can comprise about 14 mg to about 40 mg of pregnenolone. In some aspects, the composition can comprise about 14 mg to about 30 mg, about 14 mg to about 25 mg, about 14 mg to about 20 mg, about 14 mg to about 17.5 mg, about 14 mg to about 16 mg, about 14 mg to about 15.5 mg, about 14 mg to about 15 mg, or about 14 mg to about 14.5 mg of pregnenolone.

In some aspects, the composition can comprise about 15 mg to about 40 mg of pregnenolone. In some aspects, the composition can comprise about 15 mg to about 30 mg, about 15 mg to about 27.5 mg, about 15 mg to about 25 mg, about 15 mg to about 22.5 mg, about 15 mg to about 20 mg, about 15 mg to about 17.5 mg, about 15 mg to about 16.5 mg, about 15 mg to about 16 mg, or about 15 mg to about 15.5 mg of pregnenolone.

In some aspects, the composition can comprise about 17.5 mg to about 40 mg of pregnenolone. In some aspects, the composition can comprise about 17.5 mg to about 30 mg, about 17.5 mg to about 27.5 mg, about 17.5 mg to about 25 mg, about 17.5 mg to about 22.5 mg, about 17.5 mg to about 20 mg, about 17.5 mg to about 18 mg of pregnenolone.

In some aspects, the composition can comprise about 20 mg to about 40 mg of pregnenolone. In some aspects, the composition can comprise about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, about 20 mg to about 21 mg, or about 20 mg to about 20.5 mg of pregnenolone.

In some aspects, the composition can comprise about 25 mg to about 40 mg of pregnenolone. In some aspects, the composition can comprise about 25 mg to about 35 mg, about 25 mg to about 30 mg, about 25 mg to about 29 mg, about 25 mg to about 28 mg, about 25 mg to about 27 mg, about 25 mg to about 26.5 mg, about 25 mg to about 26 mg, or about 25 mg to about 25.5 mg of pregnenolone.

In some aspects, the composition can comprise about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 12.5 mg, about 15 mg, about 17.5 mg, about 20 mg, about 25 mg, about 30 mg, about 35 mg, about 40 mg of pregnenolone.

In some aspects, the composition can comprise about 1.5 mg of the SERM, or an equivalent amount of a pharmaceutically acceptable salt thereof, and about 5 mg of the neurosteroid. In some aspects, the composition can comprise about 2 mg of the SERM, or an equivalent amount of a pharmaceutically acceptable salt thereof, and about 5 mg of the neurosteroid; about 3 mg of the SERM, or an equivalent amount of a pharmaceutically acceptable salt thereof, and about 2.5 mg of the neurosteroid; about 3 mg of the SERM, or an equivalent amount of a pharmaceutically acceptable salt thereof, and about 5 mg of the neurosteroid; about 4 mg of the SERM, or an equivalent amount of a pharmaceutically acceptable salt thereof, and about 5 mg of the neurosteroid; about 6.25 mg of the SERM, or an equivalent amount of a pharmaceutically acceptable salt thereof, and about 5 mg of the neurosteroid; about 12.5 mg of the SERM, or an equivalent amount of a pharmaceutically acceptable salt thereof, and about 10 mg of the neurosteroid; about 25 mg of the SERM, or an equivalent amount of a pharmaceutically acceptable salt thereof, and about 20 mg of the neurosteroid; or about 50 mg of the SERM, or an equivalent amount of a pharmaceutically acceptable salt thereof, and about 40 mg of the neurosteroid.

In some aspects, the composition can comprise about 1.5 mg of enclomiphene, or an equivalent amount of a pharmaceutically acceptable salt thereof, and about 5 mg of pregnenolone. In some aspects, the composition can comprise about 2 mg of enclomiphene, or an equivalent amount of a pharmaceutically acceptable salt thereof, and about 5 mg of pregnenolone; about 3.125 mg of enclomiphene, or an equivalent amount of a pharmaceutically acceptable salt thereof, and about 2.5 mg of pregnenolone; about 3.125 mg of enclomiphene, or an equivalent amount of a pharmaceutically acceptable salt thereof, and about 5 mg of pregnenolone; about 4 mg of enclomiphene, or an equivalent amount of a pharmaceutically acceptable salt thereof, and about 5 mg of pregnenolone; about 6.25 mg of enclomiphene, or an equivalent amount of a pharmaceutically acceptable salt thereof, and about 5 mg of pregnenolone; about 12.5 mg of enclomiphene, or an equivalent amount of a pharmaceutically acceptable salt thereof, and about 10 mg of pregnenolone; about 25 mg of enclomiphene, or an equivalent amount of a pharmaceutically acceptable salt thereof, and about 20 mg of pregnenolone; or about 50 mg of enclomiphene, or an equivalent amount of a pharmaceutically acceptable salt thereof, and about 40 mg of pregnenolone.

In some aspects, the pharmaceutical composition can comprise a filler. In some aspects, the filler can be selected from the group consisting of cellulose and cellulose derivatives, microcrystalline cellulose, hydroxypropyl cellulose, lactose, calcium carbonate, calcium bicarbonate, calcium phosphate, dibasic calcium phosphate, calcium sulfate, calcium silicate, cellulose powders, dextrose, dextrates, dextrans, starches, pregelatinized starches, sucrose, xylitol, lactitol, sorbitol, sodium bicarbonate, sodium chloride, polyethylene glycol, and combinations thereof. In some aspects, the filler can be cellulose.

In some aspects, the filler can be present in amounts of about 10% to about 90% by weight of the composition. In some aspects, the filler can be present in amounts of about 10% to about 80%, about 10% to about 70%, about 10% to about 60%, about 10% to about 50%, about 10% to about 40%, about 10% to about 30%, or about 10% to about 20% by weight of the composition.

In some aspects, the filler can be present in amounts of about 20% to about 90% by weight of the composition. In some aspects, the filler can be present in amounts of about 20% to about 80%, about 20% to about 70%, about 20% to about 60%, about 20% to about 50%, about 20% to about 40%, or about 20% to about 30% by weight of the composition.

In some aspects, the filler can be present in amounts of about 30% to about 90% by weight of the composition. In some aspects, the filler can be present in amounts of about 30% to about 80%, about 30% to about 70%, about 30% to about 60%, about 30% to about 50%, or about 30% to about 40% by weight of the composition.

In some aspects, the filler can be present in amounts of about 40% to about 90% by weight of the composition. In some aspects, the filler can be present in amounts of about 40% to about 80%, about 40% to about 70%, about 40% to about 60%, or about 40% to about 50% by weight of the composition.

In some aspects, the filler can be present in amounts of about 50% to about 90% by weight of the composition. In some aspects, the filler can be present in amounts of about 50% to about 80%, about 50% to about 70%, or about 50% to about 60% by weight of the composition.

In some aspects, the filler can be present in amounts of about 60% to about 90% by weight of the composition. In some aspects, the filler can be present in amounts of about 60% to about 80%, or about 60% to about 70% by weight of the composition.

In some aspects, the filler can be present in amounts of about 70% to about 90% by weight of the composition. In some aspects, the filler can be present in amounts of about 70% to about 80% by weight of the composition. In some aspects, the filler can be present in amounts of about 80% to about 90% by weight of the composition.

In some aspects, the pharmaceutical composition can further comprise a sweetener. In some aspects, the sweetener can be a non-nutritive sweetener. In some aspects, the non-nutritive sweetener can be selected from the group consisting of acesulfame-K, aspartame, advantame, cyclamate, neotame, alitame, saccharin, sucralose, steviol glycosides (including, but not limited to, stevioside, steviolbioside, rebaudioside A, rebaudioside B, rebaudioside C, rebaudioside D, rebaudioside E, rebaudioside H, rebaudioside I, rebaudioside N, rebaudioside K, rebaudioside J, rebaudioside O, rebaudioside M, dulcoside A, rubusoside, iso-steviol glycosides such as iso-rebaudioside A, and mixtures thereof), Lo Han Guo powder, neohesperidin dihydrochalcone, trilobatin, glycyrrhizin, phyllodulcin, hernandulcin, osladin, polypodoside A, baiyunoside, pterocaryoside, thaumatin, monellin, monatin, and mabinlins I and II, and combinations thereof. In some aspects, the non-nutritive sweetener can be a mixture of steviol glycosides.

In some aspects, the non-nutritive sweetener can be present in amounts of about 0.01% to about 80% by weight of the composition. In some aspects, the non-nutritive sweetener can be present in amounts of about 0.01% to about 70%, about 0.01% to about 60%, about 0.01% to about 50%, about 0.01% to about 40%, about 0.01% to about 30%, about 0.01% to about 20%, about 0.01% to about 10%, about 0.01% to about 1%, or about 0.01% to about 0.1% by weight of the composition.

In some aspects, the non-nutritive sweetener can be present in amounts of about 0.1% to about 80% by weight of the composition. In some aspects, the non-nutritive sweetener can be present in amounts of about 0.1% to about 70%, about 0.1% to about 60%, about 0.1% to about 50%, about 0.1% to about 40%, about 0.1% to about 30%, about 0.1% to about 20%, about 0.1% to about 10%, or about 0.1% to about 1% by weight of the composition.

In some aspects, the non-nutritive sweetener can be present in amounts of about 1% to about 80% by weight of the composition. In some aspects, the non-nutritive sweetener can be present in amounts of about 1% to about 70%, about 1% to about 60%, about 1% to about 50%, about 1% to about 40%, about 1% to about 30%, about 1% to about 20%, about 10% to about 10%, or about 10% to about 5% by weight of the composition.

In some aspects, the non-nutritive sweetener can be present in amounts of about 5% to about 80% by weight of the composition. In some aspects, the non-nutritive sweetener can be present in amounts of about 5% to about 70%, about 5% to about 60%, about 5% to about 50%, about 5% to about 40%, about 5% to about 30%, about 5% to about 20%, about 5% to about 15%, or about 5% to about 10% by weight of the composition.

In some aspects, the non-nutritive sweetener can be present in amounts of about 10% to about 80% by weight of the composition. In some aspects, the non-nutritive sweetener can be present in amounts of about 10% to about 70%, about 10% to about 60%, about 10% to about 50%, about 10% to about 40%, about 10% to about 30%, about 10% to about 20%, or about 10% to about 15% by weight of the composition.

In some aspects, the non-nutritive sweetener can be present in amounts of about 20% to about 80% by weight of the composition. In some aspects, the non-nutritive sweetener can be present in amounts of about 20% to about 70%, about 20% to about 60%, about 20% to about 50%, about 20% to about 40%, or about 20% to about 30% by weight of the composition.

In some aspects, the non-nutritive sweetener can be present in amounts of about 40% to about 80% by weight of the composition. In some aspects, the non-nutritive sweetener can be present in amounts of about 40% to about 70%, about 40% to about 60%, or about 40% to about 50% by weight of the composition.

In some aspects, the non-nutritive sweetener can be present in amounts of about 60% to about 80% by weight of the composition. In some aspects, the non-nutritive sweetener can be present in amounts of about 60% to about 70% by weight of the composition.

In some aspects, the pharmaceutical composition can further comprise a flavoring agent. In some aspects, the flavoring agent can be selected from the group consisting of lemon flavor, grape flavor, lime flavor, orange flavor, mango flavor, passion fruit flavor, raspberry flavor, blueberry flavor, pineapple flavor, mint flavor, peppermint flavor, and combinations thereof. In some aspects, the flavoring agent can be an orange flavor. In some aspects, the flavoring agent can be a mint or peppermint flavor.

In some aspects, the flavoring agent can be present in amounts of about 0.10% to about 25% by weight of the composition. In some aspects, the flavoring agent can be present in amounts of about 0.1% to about 20%, about 0.1% to about 15%, about 0.1% to about 10%, about 0.1% to about 5%, or about 0.1% to about 1% by weight of the composition.

In some aspects, the flavoring agent can be present in amounts of about 1% to about 25% by weight of the composition. In some aspects, the flavoring agent can be present in amounts of about 1% to about 20%, about 1% to about 15%, about 1% to about 10%, or about 1% to about 5% by weight of the composition.

In some aspects, the flavoring agent can be present in amounts of about 5% to about 25% by weight of the composition. In some aspects, the flavoring agent can be present in amounts of about 5% to about 20%, about 5% to about 15%, or about 5% to about 10% by weight of the composition.

In some aspects, the flavoring agent can be present in amounts of about 10% to about 25% by weight of the composition. In some aspects, the flavoring agent can be present in amounts of about 10% to about 20%, or about 10% to about 15% by weight of the composition.

In some aspects, the flavoring agent can be present in amounts of about 15% to about 25% by weight of the composition. In some aspects, the flavoring agent can be present in amounts of about 15% to about 20% by weight of the composition. In some aspects, the flavoring agent can be present in amounts of about 20% to about 25% by weight of the composition.

In some aspects, the pharmaceutical composition can further comprise a lubricant. In some aspects, the lubricant can be selected from the group consisting of stearic acid, calcium hydroxide, talc, corn starch, sodium stearyl fumerate, stearic acid, sodium oleate, sodium stearate, sodium benzoate, sodium acetate, sodium chloride, magnesium stearate, zinc stearate, waxes, and combinations thereof. In some aspects, the lubricant can be magnesium stearate.

In some aspects, the lubricant can be present in amounts of about 0.010% to about 10% by weight of the composition. In some aspects, the lubricant can be present in amounts of about 0.01% to about 9%, about 0.01% to about 8%, about 0.01% to about 7%, about 0.010% to about 6%, about 0.010% to about 5%, about 0.010% to about 4%, about 0.01% to about 3%, about 0.01% to about 2%, about 0.01% to about 10%, about 0.01% to about 0.9%, about 0.01% to about 0.8%, about 0.01% to about 0.7%, about 0.01% to about 0.6%, about 0.01% to about 0.5%, about 0.01% to about 0.4%, about 0.01% to about 0.3%, about 0.01% to about 0.2%, or about 0.01% to about 0.1% by weight of the composition.

In some aspects, the lubricant can be present in amounts of about 0.1% to about 10% by weight of the composition. In some aspects, the lubricant can be present in amounts of about 0.1% to about 9%, about 0.1% to about 8%, about 0.10% to about 7%, about 0.10% to about 6%, about 0.10% to about 5%, about 0.10% to about 4%, about 0.1% to about 3%, about 0.10% to about 2%, about 0.1% to about 1%, about 0.10% to about 0.9%, about 0.1% to about 0.8%, about 0.1% to about 0.7%, about 0.1% to about 0.6%, about 0.1% to about 0.5%, about 0.1% to about 0.4%, about 0.1% to about 0.3%, about 0.1% to about 0.2% by weight of the composition.

In some aspects, the lubricant can be present in amounts of about 0.5% to about 10% by weight of the composition. In some aspects, the lubricant can be present in amounts of about 0.5% to about 9%, about 0.5% to about 8%, about 0.5% to about 7%, about 0.50% to about 6%, about 0.50% to about 50%, about 0.50% to about 4%, about 0.50% to about 3%, about 0.5% to about 2%, about 0.5% to about 1%, about 0.5% to about 0.9%, about 0.5% to about 0.8%, about 0.5% to about 0.7%, or about 0.5% to about 0.6% by weight of the composition.

In some aspects, the lubricant can be present in amounts of about 1% to about 10% by weight of the composition. In some aspects, the lubricant can be present in amounts of about 1% to about 9%, about 1% to about 8%, about 1% to about 7%, about 1% to about 6%, about 1% to about 5%, about 1% to about 4%, about 1% to about 3%, about 1% to about 2%, or about 1% to about 2% by weight of the composition.

In some aspects, the lubricant can be present in amounts of about 5% to about 10%, about 5% to about 9%, about 5% to about 8%, about 5% to about 7%, or about 5% to about 6% by weight of the composition.

In some aspects, the pharmaceutical composition can be in the form of a sublingual tablet. In some aspects, the pharmaceutical composition can be in the form of a buccal tablet.

In some aspects, the pharmaceutical composition can further comprise a 5α-reductase inhibitor, a compound that can inhibit the action of 5α-reductase, the enzyme that converts testosterone into dihydrotestosterone. In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects, the 5α-reductase inhibitor can be dutasteride. In some aspects, the 5α-reductase inhibitor can be finasteride.

In some aspects, the composition can comprise about 0.1 mg to about 1,000 mg of the 5α-reductase inhibitor. In some aspects, the composition can comprise about 0.1 mg to about 500 mg, about 0.1 mg to about 100 mg, about 0.1 mg to about 50 mg, or about 0.1 mg to about 10 mg of the 5α-reductase inhibitor. In some aspects, the composition can comprise about 0.1 mg to about 5 mg or about 0.1 mg to about 2.5 mg of the 5α-reductase inhibitor. In some aspects, the composition can comprise about 0.1 mg to about 2 mg, about 0.1 mg to about 1.5 mg, about 0.1 mg to about 1 mg, about 0.2 mg to about 1 mg, about 0.3 mg to about 1 mg, about 0.4 mg to about 1 mg, or about 0.5 mg to about 1 mg of the 5α-reductase inhibitor.

In some aspects, the composition can comprise about 0.1 mg to about 1 mg, about 0.1 mg to about 0.9 mg, about 0.2 mg to about 0.8 mg, about 0.3 mg to about 0.7 mg, about 0.4 mg to about 0.6 mg, or about 0.5 mg of the 5α-reductase inhibitor. In some aspects, the composition can comprise about 0.5 mg to about 1.5 mg, about 0.6 mg to about 1.4 mg, about 0.7 mg to about 1.3 mg, about 0.8 mg to about 1.2 mg, about 0.9 mg to about 1.1 mg, or about 1 mg of the 5α-reductase inhibitor. In some aspects, the composition can comprise about 0.01 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, or about 2.5 mg of the 5α-reductase inhibitor.

In some aspects, the 5α-reductase inhibitor can be dutasteride and the composition can comprise about 0.1 mg to about 5 mg, about 0.1 mg to about 4 mg, about 0.1 mg to about 3 mg, about 0.1 mg to about 2.5 mg, about 0.1 mg to about 2 mg, about 0.1 mg to about 1.5 mg, about 0.1 mg to about 1 mg, about 0.1 mg to about 0.9 mg, about 0.2 mg to about 0.8 mg, about 0.3 mg to about 0.7 mg, about 0.4 mg to about 0.6 mg, or about 0.5 mg of dutasteride. In some aspects, the 5α-reductase inhibitor can be finasteride and the composition can comprise about 0.5 mg to about 5 mg, about 0.5 mg to about 4 mg, about 0.5 mg to about 3 mg, about 0.5 mg to about 2.5 mg, about 0.5 mg to about 2 mg, about, about 0.5 mg to about 1.5 mg, about 0.6 mg to about 1.4 mg, about 0.7 mg to about 1.3 mg, about 0.8 mg to about 1.2 mg, about 0.9 mg to about 1.1 mg, or about 1 mg of finasteride.

In some aspects, the pharmaceutical composition can further comprise an aromatase inhibitor, a compound that inhibits the action of aromatase, the enzyme that converts androgens into estrogens by aromatization. In some aspects, the aromatase inhibitor can be selected from the group consisting of atamestane, exemestane, and formestane, and non-steroids, such as aminoglutethimide, roglethimide, pyridoglutethimide, trilostane, testolactone, vorozole, fadrozole, anastrozole, letrozole, and combinations thereof. In some aspects, the aromatase inhibitor can be anastrozole. In some aspects, the aromatase inhibitor can be exemestane.

In some aspects, the composition can comprise about 0.1 mg to about 50 mg of the aromatase inhibitor. In some aspects, the composition can comprise about 0.1 mg to about 40 mg, about 0.1 mg to about 30 mg, about 0.1 mg to about 25 mg, about 0.1 mg to about 20 mg, about 0.1 mg to about 15 mg, about 0.1 mg to about 12.5 mg, about 0.1 mg to about 10 mg, about 0.1 mg to about 5 mg, about 0.1 mg to about 2.5 mg, about 0.1 mg to about 1 mg, about 0.1 mg to about 0.9 mg, about 0.1 mg to about 0.8 mg, about 0.1 mg to about 0.7 mg, about 0.1 mg to about 0.6 mg, or about 0.1 mg to about 0.5 mg of the aromatase inhibitor.

In some aspects, the composition can comprise about 0.1 mg to about 0.5 mg, 0.1 mg to about 0.4 mg, about 0.1 to about 0.3 mg, about 0.2 mg to about 0.4 mg, about 0.2 mg to about 0.3 mg, or about 0.25 mg of the aromatase inhibitor. In some aspects, the composition can comprise about 0.2 mg to about 0.8 mg, 0.2 mg to about 0.6 mg, about 0.2 mg to about 0.5 mg, about 0.3 mg to about 0.7 mg, or about 0.4 mg to about 0.6 mg, or about 0.5 mg of the aromatase inhibitor. In some aspects, the composition can comprise about 0.25 mg to about 0.5 mg of the aromatase inhibitor.

In some aspects, the composition can comprise about 5 mg to about 30 mg, about 10 mg to about 30 mg, about 10 mg to about 25 mg, about 10 mg to about 20 mg, about 10 mg to about 15 mg, about 15 mg to about 30 mg, about 20 mg to about 30 mg of the aromatase inhibitor. In some aspects, the composition can comprise about 10 mg to about 15 mg, about 11 mg to about 14 mg, about 12 to about 13 mg, or about 12.5 mg of the aromatase inhibitor. In some aspects, the composition can comprise about 20 mg to about 30 mg, about 21 mg to about 29 mg, about 22 mg to about 28 mg, about 23 mg to about 27 mg, about 24 mg to about 26 mg, or about 25 mg of the aromatase inhibitor.

In some aspects, the composition can comprise about 0.1 mg, about 0.25 mg, about 0.5 mg, about 0.6 mg, about 0.7 mg, about 0.8 mg, about 0.9 mg, about 1 mg, about 1.5 mg, about 2 mg, about 2.5 mg, about 5 mg, about 7.5 mg, about 10 mg, about 12.5 mg, about 15 mg, about 20 mg, about 25 mg, about 30 mg of the aromatase inhibitor.

In some aspects, the composition can comprise about 0.1 mg to about 1 mg, about 0.1 mg to about 0.5 mg, 0.1 mg to about 0.4 mg, about 0.1 to about 0.3 mg, about 0.2 mg to about 0.4 mg, about 0.2 mg to about 0.3 mg, or about 0.25 mg of anastrozole. In some aspects, the composition can comprise about 0.2 mg to about 0.8 mg, 0.2 mg to about 0.6 mg, about 0.2 mg to about 0.5 mg, about 0.3 mg to about 0.7 mg, or about 0.4 mg to about 0.6 mg, or about 0.5 mg of anastrozole. In some aspects, the composition can comprise about 0.25 mg to about 0.5 mg of anastrozole.

In some aspects, the composition can comprise about 5 mg to about 30 mg, about 10 mg to about 30 mg, about 10 mg to about 25 mg, about 10 mg to about 20 mg, about 10 mg to about 15 mg, about 15 mg to about 30 mg, about 20 mg to about 30 mg of exemestane. In some aspects, the composition can comprise about 10 mg to about 15 mg, about 11 mg to about 14 mg, about 12 to about 13 mg, or about 12.5 mg of exemestane. In some aspects, the composition can comprise about 20 mg to about 30 mg, about 21 mg to about 29 mg, about 22 mg to about 28 mg, about 23 mg to about 27 mg, about 24 mg to about 26 mg, or about 25 mg of exemestane.

In some aspects, the pharmaceutical composition can further comprise ketoconazole.

In some aspects, a pharmaceutical composition can comprise about 1 mg to about 50 mg of a selective estrogen receptor modulator and about 100 mg to about 800 mg of testosterone, wherein the composition is suitable for oral administration, sublingual administration, or a combination thereof.

In some aspects, the selective estrogen receptor modulator can be selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof. In some aspects, the selective estrogen receptor modulator can be enclomiphene or a pharmaceutically acceptable salt thereof. In some aspects, the pharmaceutically acceptable salt of enclomiphene can be enclomiphene citrate.

In some aspects, the composition can comprise about 3 mg, about 3.125 mg, about 6.25 mg, about 12.5 mg, about 25 mg, or about 50 mg of the selective estrogen receptor modulator.

In some aspects, the composition can comprise about 200 mg, about 400 mg, about 600 mg, or about 800 mg of testosterone.

In some aspects, the composition can further comprise a neurosteroid. In some aspects, the neurosteroid can be selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof. In some aspects, the neurosteroid can be pregnenolone.

In some aspects, the composition can further comprise about 5 mg to about 40 mg of pregnenolone. In some aspects, the composition can comprise about 5 mg, about 10 mg, about 20 mg, or about 40 mg of pregnenolone.

In some aspects, the composition can further comprise a pharmaceutically acceptable excipient. In some aspects, the pharmaceutically acceptable excipient can comprise at least one of the excipients disclosed herein in the amounts and ranges also disclosed herein.

The present disclosure provides a pharmaceutical composition comprising a therapeutically effective amount of a SERM and a pharmaceutically acceptable excipient. In some aspects, the pharmaceutical composition further comprises a therapeutically effective amount of a steroid hormone. In some aspects, the steroid hormone is selected from the group consisting of a neurosteroid, dehydroepiandrosterone (DHEA), estrogen, dihydrotestosterone (DHT), and combinations thereof. In some aspects, the steroid hormone is a neurosteroid. In some aspects, the pharmaceutical composition can be suitable for topical administration, including a lotion, emulsion, cream, gel, ointment, foam, liquid, paste or other topically administrable form. In some aspects, the pharmaceutical composition can be suitable for transdermal administration, including a transdermal patch, transdermal lotion, transdermal cream, transdermal gel, transdermal ointment, transdermal foam, transdermal liquid, transdermal paste or other transdermally administrable form.

In some aspects of the topical or transdermal composition, the SERM can be selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof.

In some aspects of the topical or transdermal composition, the SERM can be enclomiphene or a pharmaceutically acceptable salt or solvate thereof. In some aspects, the pharmaceutically acceptable salt of enclomiphene can be enclomiphene citrate.

In some aspects of the topical or transdermal composition, the SERM can be clomiphene or a pharmaceutically acceptable salt or solvate thereof. In some aspects, the pharmaceutically acceptable salt of clomiphene can be clomiphene citrate.

In some aspects of the topical or transdermal composition, the SERM can be toremifene or a pharmaceutically acceptable salt or solvate thereof. In some aspects, the pharmaceutically acceptable salt of toremifene can be toremifene citrate.

In some aspects of the topical or transdermal composition, the composition can comprise about 5 mg to about 600 mg of the SERM. In some aspects of the topical or transdermal composition, the composition can comprise about 5 mg to about 500 mg, about 5 mg to about 400 mg, or about 5 mg to about 300 mg of the SERM, or an equivalent amount of a pharmaceutically acceptable salt thereof.

In some aspects of the topical or transdermal composition, the composition can comprise about 5 mg to about 250 mg of the SERM, or an equivalent amount of a pharmaceutically acceptable salt thereof. In some aspects, the composition can comprise about 5 mg to about 240 mg, about 5 mg to about 230 mg, about 5 mg to about 225 mg, about 5 mg to about 220 mg, about 5 mg to about 210 mg, about 5 mg to about 200 mg, about 5 mg to about 190 mg, about 5 mg to about 180 mg, about 5 mg to about 175 mg, about 5 mg to about 170 mg, about 5 mg to about 160 mg, about 5 mg to about 150 mg, about 5 mg to about 140 mg, about 5 mg to about 130 mg, about 5 mg to about 125 mg, about 5 mg to about 120 mg, about 5 mg to about 110 mg, about 5 mg to about 100 mg, about 5 mg to about 90 mg, about 5 mg to about 80 mg, about mg to about 70 mg, about 5 mg to about 60 mg, about 5 mg to about 50 mg, about 5 mg to about 40 mg, about 5 mg to about 30 mg, about 5 mg to about 25 mg, about 5 mg to about 20 mg, about 5 mg to about 17.5 mg, about 5 mg to about 15 mg, about 5 mg to about 15 mg, about 11 mg to about 14 mg, or about 12 mg to about 13 mg of the SERM, or an equivalent amount of a pharmaceutically acceptable salt thereof.

In some aspects of the topical or transdermal composition, the composition can comprise about 10 mg to about 250 mg of the SERM, or an equivalent amount of a pharmaceutically acceptable salt thereof. In some aspects, the composition can comprise about 10 mg to about 240 mg, about 10 mg to about 230 mg, about 10 mg to about 225 mg, about 10 mg to about 220 mg, about 10 mg to about 210 mg, about 10 mg to about 200 mg, about 10 mg to about 190 mg, about 10 mg to about 180 mg, about 10 mg to about 175 mg, about 10 mg to about 170 mg, about 10 mg to about 160 mg, about 10 mg to about 150 mg, about 10 mg to about 140 mg, about 10 mg to about 130 mg, about 10 mg to about 125 mg, about 10 mg to about 120 mg, about 10 mg to about 110 mg, about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, about 10 mg to about 25 mg, about 10 mg to about 20 mg, about 10 mg to about 17.5 mg, about 10 mg to about 15 mg, about 10 mg to about 15 mg, about 11 mg to about 14 mg, or about 12 mg to about 13 mg of the SERM, or an equivalent amount of a pharmaceutically acceptable salt thereof.

In some aspects of the topical or transdermal composition, the composition can comprise about 20 mg to about 250 mg of the SERM, or an equivalent amount of a pharmaceutically acceptable salt thereof. In some aspects, the composition can comprise about 20 mg to about 240 mg, about 20 mg to about 230 mg, about 20 mg to about 225 mg, about 20 mg to about 220 mg, about 20 mg to about 210 mg, about 20 mg to about 200 mg, about 20 mg to about 190 mg, about 20 mg to about 180 mg, about 20 mg to about 175 mg, about 20 mg to about 170 mg, about 20 mg to about 160 mg, about 20 mg to about 150 mg, about 20 mg to about 140 mg, about 20 mg to about 130 mg, about 20 mg to about 125 mg, about 20 mg to about 120 mg, about 20 mg to about 110 mg, about 20 mg to about 100 mg, about 20 mg to about 90 mg, about 20 mg to about 80 mg, about 20 mg to about 70 mg, about 20 mg to about 60 mg, about 20 mg to about 50 mg, about 20 mg to about 40 mg, about 20 mg to about 30 mg, or about 20 mg to about 25 mg of the SERM, or an equivalent amount of a pharmaceutically acceptable salt thereof.

In some aspects of the topical or transdermal composition, the composition can comprise about 40 mg to about 250 mg of the SERM, or an equivalent amount of a pharmaceutically acceptable salt thereof. In some aspects, the composition can comprise about 40 mg to about 240 mg, about 40 mg to about 230 mg, about 40 mg to about 225 mg, about 40 mg to about 220 mg, about 40 mg to about 210 mg, about 40 mg to about 200 mg, about 40 mg to about 190 mg, about 40 mg to about 180 mg, about 40 mg to about 175 mg, about 40 mg to about 170 mg, about 40 mg to about 160 mg, about 40 mg to about 150 mg, about 40 mg to about 140 mg, about 40 mg to about 130 mg, about 40 mg to about 125 mg, about 40 mg to about 120 mg, about 40 mg to about 110 mg, about 40 mg to about 100 mg, about 40 mg to about 90 mg, about 40 mg to about 80 mg, about 40 mg to about 70 mg, about 40 mg to about 60 mg, or about 40 mg to about 50 mg of the SERM, or an equivalent amount of a pharmaceutically acceptable salt thereof.

In some aspects of the topical or transdermal composition, the composition can comprise about 50 mg to about 250 mg of the SERM, or an equivalent amount of a pharmaceutically acceptable salt thereof. In some aspects, the composition can comprise about 50 mg to about 240 mg, about 50 mg to about 230 mg, about 50 mg to about 225 mg, about 50 mg to about 220 mg, about 50 mg to about 210 mg, about 50 mg to about 200 mg, about 50 mg to about 190 mg, about 50 mg to about 180 mg, about 50 mg to about 175 mg, about 50 mg to about 170 mg, about 50 mg to about 160 mg, about 50 mg to about 150 mg, about 50 mg to about 140 mg, about 50 mg to about 130 mg, about 50 mg to about 125 mg, about 50 mg to about 120 mg, about 50 mg to about 110 mg, about 50 mg to about 100 mg, about 50 mg to about 90 mg, about 50 mg to about 80 mg, about 50 mg to about 70 mg, or about 50 mg to about 60 mg of the SERM, or an equivalent amount of a pharmaceutically acceptable salt thereof.

In some aspects of the topical or transdermal composition, the composition can comprise about 60 mg to about 250 mg of the SERM, or an equivalent amount of a pharmaceutically acceptable salt thereof. In some aspects, the composition can comprise about 60 mg to about 240 mg, about 60 mg to about 230 mg, about 60 mg to about 225 mg, about 60 mg to about 220 mg, about 60 mg to about 210 mg, about 60 mg to about 200 mg, about 60 mg to about 190 mg, about 60 mg to about 180 mg, about 60 mg to about 175 mg, about 60 mg to about 170 mg, about 60 mg to about 160 mg, about 60 mg to about 150 mg, about 60 mg to about 140 mg, about 60 mg to about 130 mg, about 60 mg to about 125 mg, about 60 mg to about 120 mg, about 60 mg to about 110 mg, about 60 mg to about 100 mg, about 60 mg to about 90 mg, about 60 mg to about 80 mg, or about 60 mg to about 70 mg of the SERM, or an equivalent amount of a pharmaceutically acceptable salt thereof.

In some aspects of the topical or transdermal composition, the composition can comprise about 80 mg to about 250 mg of the SERM, or an equivalent amount of a pharmaceutically acceptable salt thereof. In some aspects, the composition can comprise about 80 mg to about 240 mg, about 80 mg to about 230 mg, about 80 mg to about 225 mg, about 80 mg to about 220 mg, about 80 mg to about 210 mg, about 80 mg to about 200 mg, about 80 mg to about 190 mg, about 80 mg to about 180 mg, about 80 mg to about 175 mg, about 80 mg to about 170 mg, about 80 mg to about 160 mg, about 80 mg to about 150 mg, about 80 mg to about 140 mg, about 80 mg to about 130 mg, about 80 mg to about 125 mg, about 80 mg to about 120 mg, about 80 mg to about 110 mg, about 80 mg to about 100 mg, or about 80 mg to about 90 mg of the SERM, or an equivalent amount of a pharmaceutically acceptable salt thereof.

In some aspects of the topical or transdermal composition, the composition can comprise about 100 mg to about 250 mg of the SERM, or an equivalent amount of a pharmaceutically acceptable salt thereof. In some aspects, the composition can comprise about 100 mg to about 240 mg, about 100 mg to about 230 mg, about 100 mg to about 225 mg, about 100 mg to about 220 mg, about 100 mg to about 210 mg, about 100 mg to about 200 mg, about 100 mg to about 190 mg, about 100 mg to about 180 mg, about 100 mg to about 175 mg, about 100 mg to about 170 mg, about 100 mg to about 160 mg, about 100 mg to about 150 mg, about 100 mg to about 140 mg, about 100 mg to about 130 mg, about 100 mg to about 125 mg, about 100 mg to 120 mg, or about 100 mg to about 110 mg of the SERM, or an equivalent amount of a pharmaceutically acceptable salt thereof.

In some aspects of the topical or transdermal composition, the composition can comprise about 120 mg to about 250 mg, about 150 mg to about 250 mg, or about 200 mg to about 250 mg of the SERM, or an equivalent amount of a pharmaceutically acceptable salt thereof.

In some aspects of the topical or transdermal composition, the composition can comprise about 5 mg, about 6.25 mg, about 10 mg, about 12.5 mg, about 20 mg, about 25 mg, about 40 mg, about 50 mg, about 60 mg, about 75 mg, about 80 mg, about 100 mg, about 120 mg, about 125 mg, about 150 mg, about 175 mg, about 200 mg, about 225 mg, about 250 mg of the SERM or an equivalent amount of a pharmaceutically acceptable salt thereof.

In some aspects of the topical or transdermal composition, the composition can comprise about 5 mg to about 150 mg of enclomiphene, or an equivalent amount of a pharmaceutically acceptable salt thereof. In some aspects, the composition can comprise about 5 mg to about 140 mg, about 5 mg to about 130 mg, about 5 mg to about 125 mg, about 5 mg to about 120 mg, about 5 mg to about 110 mg, about 5 mg to about 100 mg, about 5 mg to about 90 mg, about 5 mg to about 80 mg, about 5 mg to about 70 mg, about 5 mg to about 60 mg, about 5 mg to about 50 mg, about 5 mg to about 40 mg, about 5 mg to about 30 mg, about 5 mg to about 25 mg, about 5 mg to about 20 mg, about 5 mg to about 17.5 mg, about 5 mg to about 15 mg, or about 11 mg to about 14 mg, or about 12 mg to about 13 mg of enclomiphene, or an equivalent amount of a pharmaceutically acceptable salt thereof.

In some aspects of the topical or transdermal composition, the composition can comprise about 10 mg to about 150 mg of enclomiphene, or an equivalent amount of a pharmaceutically acceptable salt thereof. In some aspects, the composition can comprise about 10 mg to about 140 mg, about 10 mg to about 130 mg, about 10 mg to about 125 mg, about 10 mg to about 120 mg, about 10 mg to about 110 mg, about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, about 10 mg to about 25 mg, about 10 mg to about 20 mg, about 10 mg to about 17.5 mg, about 10 mg to about 15 mg, or about 11 mg to about 14 mg, or about 12 mg to about 13 mg of enclomiphene, or an equivalent amount of a pharmaceutically acceptable salt thereof.

In some aspects of the topical or transdermal composition, the composition can comprise about 20 mg to about 150 mg of enclomiphene, or an equivalent amount of a pharmaceutically acceptable salt thereof. In some aspects, the composition can comprise about 20 mg to about 140 mg, about 20 mg to about 130 mg, about 20 mg to about 125 mg, about 20 mg to about 120 mg, about 20 mg to about 110 mg, about 20 mg to about 100 mg, about 20 mg to about 90 mg, about 20 mg to about 80 mg, about 20 mg to about 70 mg, about 20 mg to about 60 mg, about 20 mg to about 50 mg, about 20 mg to about 40 mg, about 20 mg to about 30 mg, or about 20 mg to about 25 mg of enclomiphene, or an equivalent amount of a pharmaceutically acceptable salt thereof.

In some aspects of the topical or transdermal composition, the composition can comprise about 30 mg to about 150 mg of enclomiphene, or an equivalent amount of a pharmaceutically acceptable salt thereof. In some aspects, the composition can comprise about 30 mg to about 140 mg, about 30 mg to about 130 mg, about 30 mg to about 125 mg, about 30 mg to about 120 mg, about 30 mg to about 110 mg, about 30 mg to about 100 mg, about 30 mg to about 90 mg, about 30 mg to about 80 mg, about 30 mg to about 70 mg, about 30 mg to about 60 mg, about 30 mg to about 50 mg, or about 30 mg to about 40 mg of enclomiphene, or an equivalent amount of a pharmaceutically acceptable salt thereof.

In some aspects of the topical or transdermal composition, the composition can comprise about 40 mg to about 150 mg of enclomiphene, or an equivalent amount of a pharmaceutically acceptable salt thereof. In some aspects, the composition can comprise about 40 mg to about 140 mg, about 40 mg to about 130 mg, about 40 mg to about 125 mg, about 40 mg to about 120 mg, about 40 mg to about 110 mg, about 40 mg to about 100 mg, about 40 mg to about 90 mg, about 40 mg to about 80 mg, about 40 mg to about 70 mg, about 40 mg to about 60 mg, or about 40 mg to about 50 mg of enclomiphene, or an equivalent amount of a pharmaceutically acceptable salt thereof.

In some aspects of the topical or transdermal composition, the composition can comprise about 50 mg to about 150 mg of enclomiphene, or an equivalent amount of a pharmaceutically acceptable salt thereof. In some aspects, the composition can comprise about 50 mg to about 140 mg, about 50 mg to about 130 mg, about 50 mg to about 125 mg, about 50 mg to about 120 mg, about 50 mg to about 110 mg, about 50 mg to about 100 mg, about 50 mg to about 90 mg, about 50 mg to about 80 mg, about 50 mg to about 70 mg, or about 50 mg to about 60 mg of enclomiphene, or an equivalent amount of a pharmaceutically acceptable salt thereof.

In some aspects of the topical or transdermal composition, the composition can comprise about 5 mg, about 6.25 mg, about 10 mg, about 12.5 mg, about 20 mg, about 25 mg, about 40 mg, about 50 mg, about 60 mg, about 75 mg, about 80 mg, about 100 mg, about 120 mg, about 125 mg, or about 150 mg of enclomiphene, or an equivalent amount of a pharmaceutically acceptable salt thereof.

In some aspects of the topical or transdermal composition, the composition can comprise about 5 mg to about 150 mg of clomiphene, or an equivalent amount of a pharmaceutically acceptable salt thereof. In some aspects, the composition can comprise about 5 mg to about 140 mg, about 5 mg to about 130 mg, about 5 mg to about 125 mg, about 5 mg to about 120 mg, about 5 mg to about 110 mg, about 5 mg to about 100 mg, about 5 mg to about 90 mg, about 5 mg to about 80 mg, about 5 mg to about 70 mg, about 5 mg to about 60 mg, about 5 mg to about 50 mg, about 5 mg to about 40 mg, about 5 mg to about 30 mg, about 5 mg to about 25 mg, about 5 mg to about 20 mg, about 5 mg to about 17.5 mg, about 5 mg to about 15 mg, or about 11 mg to about 14 mg, or about 12 mg to about 13 mg of clomiphene, or an equivalent amount of a pharmaceutically acceptable salt thereof.

In some aspects of the topical or transdermal composition, the composition can comprise about 10 mg to about 150 mg of clomiphene, or an equivalent amount of a pharmaceutically acceptable salt thereof. In some aspects, the composition can comprise about 10 mg to about 140 mg, about 10 mg to about 130 mg, about 10 mg to about 125 mg, about 10 mg to about 120 mg, about 10 mg to about 110 mg, about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, about 10 mg to about 25 mg, about 10 mg to about 20 mg, about 10 mg to about 17.5 mg, about 10 mg to about 15 mg, or about 11 mg to about 14 mg, or about 12 mg to about 13 mg of clomiphene, or an equivalent amount of a pharmaceutically acceptable salt thereof.

In some aspects of the topical or transdermal composition, the composition can comprise about 20 mg to about 150 mg of clomiphene, or an equivalent amount of a pharmaceutically acceptable salt thereof. In some aspects, the composition can comprise about 20 mg to about 140 mg, about 20 mg to about 130 mg, about 20 mg to about 125 mg, about 20 mg to about 120 mg, about 20 mg to about 110 mg, about 20 mg to about 100 mg, about 20 mg to about 90 mg, about 20 mg to about 80 mg, about 20 mg to about 70 mg, about 20 mg to about 60 mg, about 20 mg to about 50 mg, about 20 mg to about 40 mg, about 20 mg to about 30 mg, or about 20 mg to about 25 mg of clomiphene, or an equivalent amount of a pharmaceutically acceptable salt thereof.

In some aspects of the topical or transdermal composition, the composition can comprise about 30 mg to about 150 mg of clomiphene, or an equivalent amount of a pharmaceutically acceptable salt thereof. In some aspects, the composition can comprise about 30 mg to about 140 mg, about 30 mg to about 130 mg, about 30 mg to about 125 mg, about 30 mg to about 120 mg, about 30 mg to about 110 mg, about 30 mg to about 100 mg, about 30 mg to about 90 mg, about 30 mg to about 80 mg, about 30 mg to about 70 mg, about 30 mg to about 60 mg, about 30 mg to about 50 mg, or about 30 mg to about 40 mg of clomiphene, or an equivalent amount of a pharmaceutically acceptable salt thereof.

In some aspects of the topical or transdermal composition, the composition can comprise about 40 mg to about 150 mg of clomiphene, or an equivalent amount of a pharmaceutically acceptable salt thereof. In some aspects, the composition can comprise about 40 mg to about 140 mg, about 40 mg to about 130 mg, about 40 mg to about 125 mg, about 40 mg to about 120 mg, about 40 mg to about 110 mg, about 40 mg to about 100 mg, about 40 mg to about 90 mg, about 40 mg to about 80 mg, about 40 mg to about 70 mg, about 40 mg to about 60 mg, or about 40 mg to about 50 mg of clomiphene, or an equivalent amount of a pharmaceutically acceptable salt thereof.

In some aspects of the topical or transdermal composition, the composition can comprise about 50 mg to about 150 mg of clomiphene, or an equivalent amount of a pharmaceutically acceptable salt thereof. In some aspects, the composition can comprise about 50 mg to about 140 mg, about 50 mg to about 130 mg, about 50 mg to about 125 mg, about 50 mg to about 120 mg, about 50 mg to about 110 mg, about 50 mg to about 100 mg, about 50 mg to about 90 mg, about 50 mg to about 80 mg, about 50 mg to about 70 mg, or about 50 mg to about 60 mg of clomiphene, or an equivalent amount of a pharmaceutically acceptable salt thereof.

In some aspects of the topical or transdermal composition, the composition can comprise about 5 mg, about 6.25 mg, about 10 mg, about 12.5 mg, about 20 mg, about 25 mg, about 40 mg, about 50 mg, about 60 mg, about 75 mg, about 80 mg, about 100 mg, about 120 mg, about 125 mg, or about 150 mg of clomiphene, or an equivalent amount of a pharmaceutically acceptable salt thereof.

In some aspects of the topical or transdermal composition, the composition can comprise about 5 mg to about 250 mg of toremifene, or an equivalent amount of a pharmaceutically acceptable salt thereof. In some aspects, the composition can comprise about 5 mg to about 240 mg, about 5 mg to about 230 mg, about 5 mg to about 220 mg, about 5 mg to about 210 mg, about 5 mg to about 200 mg, about 5 mg to about 190 mg, about 5 mg to about 180 mg, about 5 mg to about 170 mg, about 5 mg to about 160 mg, about 5 mg to about 150 mg, about 5 mg to about 140 mg, about 5 mg to about 130 mg, about 5 mg to about 120 mg, about 5 mg to about 110 mg, about 5 mg to about 100 mg, about 5 mg to about 90 mg, about 5 mg to about 80 mg, about 5 mg to about 70 mg, about 5 mg to about 60 mg, about 5 mg to about 50 mg, about 5 mg to about 40 mg, about 5 mg to about 30 mg, about 5 mg to about 27.5 mg, about 5 mg to about 25 mg, or about 5 mg to about 22.5 mg of toremifene, or an equivalent amount of a pharmaceutically acceptable salt thereof.

In some aspects of the topical or transdermal composition, the composition can comprise about 10 mg to about 250 mg of toremifene, or an equivalent amount of a pharmaceutically acceptable salt thereof. In some aspects, the composition can comprise about 10 mg to about 240 mg, about 10 mg to about 230 mg, about 10 mg to about 220 mg, about 10 mg to about 210 mg, about 10 mg to about 200 mg, about 10 mg to about 190 mg, about 10 mg to about 180 mg, about 10 mg to about 170 mg, about 10 mg to about 160 mg, about 10 mg to about 150 mg, about 10 mg to about 140 mg, about 10 mg to about 130 mg, about 10 mg to about 120 mg, about 10 mg to about 110 mg, about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, about 10 mg to about 27.5 mg, about 10 mg to about 25 mg, or about 10 mg to about 22.5 mg of toremifene, or an equivalent amount of a pharmaceutically acceptable salt thereof.

In some aspects of the topical or transdermal composition, the composition can comprise about 20 mg to about 250 mg of toremifene, or an equivalent amount of a pharmaceutically acceptable salt thereof. In some aspects, the composition can comprise about 20 mg to about 240 mg, about 20 mg to about 230 mg, about 20 mg to about 220 mg, about 20 mg to about 210 mg, about 20 mg to about 200 mg, about 20 mg to about 190 mg, about 20 mg to about 180 mg, about 20 mg to about 170 mg, about 20 mg to about 160 mg, about 20 mg to about 150 mg, about 20 mg to about 140 mg, about 20 mg to about 130 mg, about 20 mg to about 120 mg, about 20 mg to about 110 mg, about 20 mg to about 100 mg, about 20 mg to about 90 mg, about 20 mg to about 80 mg, about 20 mg to about 70 mg, about 20 mg to about 60 mg, about 20 mg to about 50 mg, about 20 mg to about 40 mg, about 20 mg to about 30 mg, about 20 mg to about 27.5 mg, about 20 mg to about 25 mg, or about 20 mg to about 22.5 mg of toremifene, or an equivalent amount of a pharmaceutically acceptable salt thereof.

In some aspects of the topical or transdermal composition, the composition can comprise about 30 mg to about 250 mg of toremifene, or an equivalent amount of a pharmaceutically acceptable salt thereof. In some aspects, the composition can comprise about 30 mg to about 240 mg, about 30 mg to about 230 mg, about 30 mg to about 220 mg, about 30 mg to about 210 mg, about 30 mg to about 200 mg, about 30 mg to about 190 mg, about 30 mg to about 180 mg, about 30 mg to about 170 mg, about 30 mg to about 160 mg, about 30 mg to about 150 mg, about 30 mg to about 140 mg, about 30 mg to about 130 mg, about 30 mg to about 120 mg, about 30 mg to about 110 mg, about 30 mg to about 100 mg, about 30 mg to about 90 mg, about 30 mg to about 80 mg, about 30 mg to about 70 mg, about 30 mg to about 60 mg, about 30 mg to about 50 mg, or about 30 mg to about 40 mg of toremifene, or an equivalent amount of a pharmaceutically acceptable salt thereof.

In some aspects of the topical or transdermal composition, the composition can comprise about 50 mg to about 250 mg of toremifene, or an equivalent amount of a pharmaceutically acceptable salt thereof. In some aspects, the composition can comprise about 50 mg to about 240 mg, about 50 mg to about 230 mg, about 50 mg to about 220 mg, about 50 mg to about 210 mg, about 50 mg to about 200 mg, about 50 mg to about 190 mg, about 50 mg to about 180 mg, about 50 mg to about 170 mg, about 50 mg to about 160 mg, about 50 mg to about 150 mg, about 50 mg to about 140 mg, about 50 mg to about 130 mg, about 50 mg to about 120 mg, about 50 mg to about 110 mg, about 50 mg to about 100 mg, about 50 mg to about 90 mg, about 50 mg to about 80 mg, about 50 mg to about 70 mg, or about 50 mg to about 60 mg of toremifene, or an equivalent amount of a pharmaceutically acceptable salt thereof.

In some aspects of the topical or transdermal composition, the composition can comprise about 60 mg to about 250 mg of toremifene, or an equivalent amount of a pharmaceutically acceptable salt thereof. In some aspects, the composition can comprise about 60 mg to about 240 mg, about 60 mg to about 230 mg, about 60 mg to about 220 mg, about 60 mg to about 210 mg, about 60 mg to about 200 mg, about 60 mg to about 190 mg, about 60 mg to about 180 mg, about 60 mg to about 170 mg, about 60 mg to about 160 mg, about 60 mg to about 150 mg, about 60 mg to about 140 mg, about 60 mg to about 130 mg, about 60 mg to about 120 mg, about 60 mg to about 110 mg, about 60 mg to about 100 mg, about 60 mg to about 90 mg, about 60 mg to about 80 mg, or about 60 mg to about 70 mg of toremifene, or an equivalent amount of a pharmaceutically acceptable salt thereof.

In some aspects of the topical or transdermal composition, the composition can comprise about 80 mg to about 250 mg of toremifene, or an equivalent amount of a pharmaceutically acceptable salt thereof. In some aspects, the composition can comprise about 80 mg to about 240 mg, about 80 mg to about 230 mg, about 80 mg to about 220 mg, about 80 mg to about 210 mg, about 80 mg to about 200 mg, about 80 mg to about 190 mg, about 80 mg to about 180 mg, about 80 mg to about 170 mg, about 80 mg to about 160 mg, about 80 mg to about 150 mg, about 80 mg to about 140 mg, about 80 mg to about 130 mg, about 80 mg to about 120 mg, about 80 mg to about 110 mg, about 80 mg to about 100 mg, or about 80 mg to about 90 mg of toremifene, or an equivalent amount of a pharmaceutically acceptable salt thereof.

In some aspects of the topical or transdermal composition, the composition can comprise about 100 mg to about 250 mg of toremifene, or an equivalent amount of a pharmaceutically acceptable salt thereof. In some aspects, the composition can comprise about 100 mg to about 240 mg, about 100 mg to about 230 mg, about 100 mg to about 220 mg, about 100 mg to about 210 mg, about 100 mg to about 200 mg, about 100 mg to about 190 mg, about 100 mg to about 180 mg, about 100 mg to about 170 mg, about 100 mg to about 160 mg, about 100 mg to about 150 mg, about 100 mg to about 140 mg, about 100 mg to about 130 mg, or about 100 mg to about 125 mg of toremifene, or an equivalent amount of a pharmaceutically acceptable salt thereof.

In some aspects of the topical or transdermal composition, the composition can comprise about 10 mg, about 12.5 mg, about 20 mg, about 25 mg, about 40 mg, about 50 mg, about 60 mg, about 75 mg, about 80 mg, about 100 mg, about 120 mg, about 125 mg, or about 150 mg of toremifene, or an equivalent amount of a pharmaceutically acceptable salt thereof.

In some aspects of the topical or transdermal composition, the neurosteroid can be selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof. In some aspects, the neurosteroid can be pregnenolone.

In some aspects of the topical or transdermal composition, the composition can comprise about 1 mg to about 200 mg of the neurosteroid. In some aspects, the composition can comprise about 1 mg to about 150 mg, about 1 mg to about 100 mg, about 1 mg to about 80 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 10 mg to about 200 mg, about 20 mg to about 200 mg, or about 40 mg to about 200 mg of the neurosteroid.

In some aspects of the topical or transdermal composition, the composition can comprise about 1 mg to about 200 mg of pregnenolone. In some aspects, the composition can comprise about 1 mg to about 150 mg, about 1 mg to about 100 mg, about 1 mg to about 80 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 10 mg to about 200 mg, about 20 mg to about 200 mg, or about 40 mg to about 200 mg of pregnenolone.

In some aspects of the topical or transdermal composition, the composition can comprise about 6.25 mg of the SERM, or an equivalent amount of a pharmaceutically acceptable salt thereof, and about 2.5 mg of the neurosteroid. In some aspects, the composition can comprise about 12.5 mg of the SERM, or an equivalent amount of a pharmaceutically acceptable salt thereof, and about 5 mg of the neurosteroid; about 12.5 mg of the SERM, or an equivalent amount of a pharmaceutically acceptable salt thereof, and about 10 mg of the neurosteroid; about 25 mg of the SERM, or an equivalent amount of a pharmaceutically acceptable salt thereof, and about 20 mg of the neurosteroid; or about 50 mg of the SERM, or an equivalent amount of a pharmaceutically acceptable salt thereof, and about 40 mg of the neurosteroid.

In some aspects, the composition can comprise about 6.25 mg of enclomiphene, or an equivalent amount of a pharmaceutically acceptable salt thereof, and about 2.5 mg of pregnenolone. In some aspects, the composition can comprise about 12.5 mg of enclomiphene, or an equivalent amount of a pharmaceutically acceptable salt thereof, and about 5 mg of pregnenolone; about 12.5 mg of enclomiphene, or an equivalent amount of a pharmaceutically acceptable salt thereof, and about 10 mg of pregnenolone; about 25 mg of enclomiphene, or an equivalent amount of a pharmaceutically acceptable salt thereof, and about 20 mg of pregnenolone; or about 50 mg of enclomiphene, or an equivalent amount of a pharmaceutically acceptable salt thereof, and about 40 mg of pregnenolone.

In some aspects of the topical or transdermal composition, any pharmaceutically acceptable excipient known in the art can be used to prepare the composition. Examples of excipients that can be included in the composition include, but are not limited to, carriers, stabilizers, preservatives, antioxidants, moisturizers, emollients, buffering agents, solubilizing agents, other penetration agents, skin protectants, surfactants, and propellants. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topical or transdermal administration. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable buffering agents include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants include, but are not limited to, vitamin E oil, allatoin, dimethicone, glycerin, petrolatum, and zinc oxide.

In some aspects, the at least one pharmaceutically acceptable excipient comprises dimethicone, lecithin, titanium dioxide, and sodium hyaluronate.

In some aspects, the at least one pharmaceutically acceptable excipient comprises cyclopentasiloxane and ethoxy diglycol.

In some aspects of the topical or transdermal composition, the pharmaceutical composition can be in the form of a topical lotion. In some aspects of the topical or transdermal composition, the pharmaceutical composition can be in the form of a topical emulsion. In some aspects of the topical or transdermal composition, the pharmaceutical composition can be in the form of a topical cream. In some aspects of the topical or transdermal composition, the pharmaceutical composition can be in the form of a topical gel. In some aspects of the topical or transdermal composition, the pharmaceutical composition can be in the form of a topical ointment. In some aspects of the topical or transdermal composition, the pharmaceutical composition can be in the form of a topical foam. In some aspects of the topical or transdermal composition, the pharmaceutical composition can be in the form of a topical liquid. In some aspects of the topical or transdermal composition, the pharmaceutical composition can be in the form of a topical paste. In some aspects of the topical or transdermal composition, the pharmaceutical composition can be in the form of a topical spray.

In some aspects of the topical or transdermal composition, the pharmaceutical composition can be in the form of a transdermal patch. In some aspects of the topical or transdermal composition, the pharmaceutical composition can be in the form of a transdermal gel. In some aspects of the topical or transdermal composition, the pharmaceutical composition can be in the form of a transdermal lotion. In some aspects of the topical or transdermal composition, the pharmaceutical composition can be in the form of a transdermal cream. In some aspects of the topical or transdermal composition, the pharmaceutical composition can be in the form of a transdermal ointment. In some aspects of the topical or transdermal composition, the pharmaceutical composition can be in the form of a transdermal foam. In some aspects of the topical or transdermal composition, the pharmaceutical composition can be in the form of a transdermal liquid. In some aspects of the topical or transdermal composition, the pharmaceutical composition can be in the form of a transdermal paste.

In some aspects of the topical or transdermal composition, the pharmaceutical composition can further comprise a 5α-reductase inhibitor, a compound that can inhibit the action of 5α-reductase, the enzyme that converts testosterone into dihydrotestosterone. In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects, the 5α-reductase inhibitor can be dutasteride. In some aspects, the 5α-reductase inhibitor can be finasteride.

In some aspects of the topical or transdermal composition, the composition can comprise about 0.1 mg to about 1,000 mg of the 5α-reductase inhibitor. In some aspects, the composition can comprise about 0.1 mg to about 500 mg, about 0.1 mg to about 100 mg, about 0.1 mg to about 50 mg, or about 0.1 mg to about 10 mg of the 5α-reductase inhibitor. In some aspects, the composition can comprise about 0.1 mg to about 5 mg or about 0.1 mg to about 2.5 mg of the 5α-reductase inhibitor. In some aspects, the composition can comprise about 0.1 mg to about 2 mg, about 0.1 mg to about 1.5 mg, about 0.1 mg to about 1 mg, about 0.2 mg to about 1 mg, about 0.3 mg to about 1 mg, about 0.4 mg to about 1 mg, or about 0.5 mg to about 1 mg of the 5α-reductase inhibitor.

In some aspects of the topical or transdermal composition, the composition can comprise about 0.1 mg to about 1 mg, about 0.1 mg to about 0.9 mg, about 0.2 mg to about 0.8 mg, about 0.3 mg to about 0.7 mg, about 0.4 mg to about 0.6 mg, or about 0.5 mg of the 5α-reductase inhibitor. In some aspects, the composition can comprise about 0.5 mg to about 1.5 mg, about 0.6 mg to about 1.4 mg, about 0.7 mg to about 1.3 mg, about 0.8 mg to about 1.2 mg, about 0.9 mg to about 1.1 mg, or about 1 mg of the 5α-reductase inhibitor. In some aspects, the composition can comprise about 0.01 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, or about 2.5 mg of the 5α-reductase inhibitor.

In some aspects of the topical or transdermal composition, the 5α-reductase inhibitor can be dutasteride and the composition can comprise about 0.1 mg to about 5 mg, about 0.1 mg to about 4 mg, about 0.1 mg to about 3 mg, about 0.1 mg to about 2.5 mg, about 0.1 mg to about 2 mg, about 0.1 mg to about 1.5 mg, about 0.1 mg to about 1 mg, about 0.1 mg to about 0.9 mg, about 0.2 mg to about 0.8 mg, about 0.3 mg to about 0.7 mg, about 0.4 mg to about 0.6 mg, or about 0.5 mg of dutasteride. In some aspects, the 5α-reductase inhibitor can be finasteride and the composition can comprise about 0.5 mg to about 5 mg, about 0.5 mg to about 4 mg, about 0.5 mg to about 3 mg, about 0.5 mg to about 2.5 mg, about 0.5 mg to about 2 mg, about, about 0.5 mg to about 1.5 mg, about 0.6 mg to about 1.4 mg, about 0.7 mg to about 1.3 mg, about 0.8 mg to about 1.2 mg, about 0.9 mg to about 1.1 mg, or about 1 mg of finasteride.

In some aspects of the topical or transdermal composition, the pharmaceutical composition can further comprise an aromatase inhibitor, a compound that inhibits the action of aromatase, the enzyme that converts androgens into estrogens by aromatization. In some aspects, the aromatase inhibitor can be selected from the group consisting of atamestane, exemestane, and formestane, and non-steroids, such as aminoglutethimide, roglethimide, pyridoglutethimide, trilostane, testolactone, vorozole, fadrozole, anastrozole, letrozole, and combinations thereof. In some aspects, the aromatase inhibitor can be anastrozole. In some aspects, the aromatase inhibitor can be exemestane.

In some aspects of the topical or transdermal composition, the composition can comprise about 0.1 mg to about 50 mg of the aromatase inhibitor. In some aspects, the composition can comprise about 0.1 mg to about 40 mg, about 0.1 mg to about 30 mg, about 0.1 mg to about 25 mg, about 0.1 mg to about 20 mg, about 0.1 mg to about 15 mg, about 0.1 mg to about 12.5 mg, about 0.1 mg to about 10 mg, about 0.1 mg to about 5 mg, about 0.1 mg to about 2.5 mg, about 0.1 mg to about 1 mg, about 0.1 mg to about 0.9 mg, about 0.1 mg to about 0.8 mg, about 0.1 mg to about 0.7 mg, about 0.1 mg to about 0.6 mg, or about 0.1 mg to about 0.5 mg of the aromatase inhibitor.

In some aspects of the topical or transdermal composition, the composition can comprise about 0.1 mg to about 0.5 mg, 0.1 mg to about 0.4 mg, about 0.1 to about 0.3 mg, about 0.2 mg to about 0.4 mg, about 0.2 mg to about 0.3 mg, or about 0.25 mg of the aromatase inhibitor. In some aspects, the composition can comprise about 0.2 mg to about 0.8 mg, 0.2 mg to about 0.6 mg, about 0.2 mg to about 0.5 mg, about 0.3 mg to about 0.7 mg, or about 0.4 mg to about 0.6 mg, or about 0.5 mg of the aromatase inhibitor. In some aspects, the composition can comprise about 0.25 mg to about 0.5 mg of the aromatase inhibitor.

In some aspects of the topical or transdermal composition, the composition can comprise about 5 mg to about 30 mg, about 10 mg to about 30 mg, about 10 mg to about 25 mg, about 10 mg to about 20 mg, about 10 mg to about 15 mg, about 15 mg to about 30 mg, about 20 mg to about 30 mg of the aromatase inhibitor. In some aspects, the composition can comprise about 10 mg to about 15 mg, about 11 mg to about 14 mg, about 12 to about 13 mg, or about 12.5 mg of the aromatase inhibitor. In some aspects, the composition can comprise about 20 mg to about 30 mg, about 21 mg to about 29 mg, about 22 mg to about 28 mg, about 23 mg to about 27 mg, about 24 mg to about 26 mg, or about 25 mg of the aromatase inhibitor.

In some aspects of the topical or transdermal composition, the composition can comprise about 0.1 mg, about 0.25 mg, about 0.5 mg, about 0.6 mg, about 0.7 mg, about 0.8 mg, about 0.9 mg, about 1 mg, about 1.5 mg, about 2 mg, about 2.5 mg, about 5 mg, about 7.5 mg, about 10 mg, about 12.5 mg, about 15 mg, about 20 mg, about 25 mg, about 30 mg of the aromatase inhibitor.

In some aspects of the topical or transdermal composition, the composition can comprise about 0.1 mg to about 1 mg, about 0.1 mg to about 0.5 mg, 0.1 mg to about 0.4 mg, about 0.1 to about 0.3 mg, about 0.2 mg to about 0.4 mg, about 0.2 mg to about 0.3 mg, or about 0.25 mg of anastrozole. In some aspects, the composition can comprise about 0.2 mg to about 0.8 mg, 0.2 mg to about 0.6 mg, about 0.2 mg to about 0.5 mg, about 0.3 mg to about 0.7 mg, or about 0.4 mg to about 0.6 mg, or about 0.5 mg of anastrozole. In some aspects, the composition can comprise about 0.25 mg to about 0.5 mg of anastrozole.

In some aspects of the topical or transdermal composition, the composition can comprise about 5 mg to about 30 mg, about 10 mg to about 30 mg, about 10 mg to about 25 mg, about 10 mg to about 20 mg, about 10 mg to about 15 mg, about 15 mg to about 30 mg, about 20 mg to about 30 mg of exemestane. In some aspects, the composition can comprise about 10 mg to about 15 mg, about 11 mg to about 14 mg, about 12 to about 13 mg, or about 12.5 mg of exemestane. In some aspects, the composition can comprise about 20 mg to about 30 mg, about 21 mg to about 29 mg, about 22 mg to about 28 mg, about 23 mg to about 27 mg, about 24 mg to about 26 mg, or about 25 mg of exemestane.

In some aspects of the topical or transdermal composition, the pharmaceutical composition can further comprise ketoconazole.

In some aspects of the topical or transdermal composition, the pharmaceutical composition can comprise about 50 mg to about 1,500 mg of testosterone.

In some aspects of the topical or transdermal composition, the composition can comprise about 50 mg, about 100 mg, about 200 mg, about 400 mg, about 600 mg, about 800 mg, about 1,000 mg, about 1,200 mg, or about 1,500 mg of testosterone.

Pharmaceutical Combinations

The present disclosure is also directed to a pharmaceutical combination comprising a first composition comprising a therapeutically effective amount of a selective estrogen receptor modulator (SERM), and a second composition comprising testosterone in a form suitable for oral administration. In some aspects, the first composition and the second composition can be administered simultaneously, concurrently, or sequentially.

In some aspects, the first composition comprising the therapeutically effective amount of the SERM can be in a form suitable for oral administration. In some aspects, the first composition can be an oral tablet or capsule. In some aspects, the first composition can be in a form suitable for sublingual administration. In some aspects, the first composition can be a sublingual tablet.

In some aspects, the second composition can be in the form of an oral tablet or capsule. In some aspects, the oral tablet or capsule can comprise a lipid bilayer. In some aspects, the oral tablet or capsule can be suitable for lymphatic absorption. In certain aspects, the first and second compositions are not in a troche dosage form. In some aspects, the second composition can be in oral form, buccal form, topical cream form, topical gel form, intranasal form, or transdermal patch form.

In some aspects, the first composition can be the pharmaceutical composition, described above, comprising therapeutically effective amounts of the SERM and the steroid hormone. In some aspects, the steroid hormone is selected from the group consisting of a neurosteroid, DHEA, estrogen, DHT, and combinations thereof. In some aspects, the steroid hormone is a neurosteroid.

In other aspects, the combination can comprise a first composition comprising a therapeutically effective amount of a selective estrogen receptor modulator (SERM), a second composition comprising testosterone in a form suitable for oral administration, and a third composition comprising a therapeutically effective amount of the neurosteroid. In some aspects of this combination, the third composition comprising the therapeutically effective amount of the neurosteroid can be in a form suitable for sublingual administration. In some aspects, the third composition comprising the therapeutically effective amount of the neurosteroid in a form suitable for sublingual administration can be a tablet. In some aspects, the third composition can comprise the neurosteroid in the amounts described above related to the pharmaceutical composition. In some aspects, the neurosteroid can be pregnenolone. In some aspects, the third composition can comprise pregnenolone in the amounts described above related to the pharmaceutical composition. In certain aspects of the combination comprising the three compositions, the first, second, and third compositions, can be administered simultaneously, concurrently, or sequentially.

In some aspects, the first composition can comprise about 1 mg to about 80 mg of the SERM, or an equivalent amount of a pharmaceutically acceptable salt thereof. In some aspects, the first composition can comprise about 1 mg to about 70 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of the SERM, or an equivalent amount of a pharmaceutically acceptable salt thereof.

In some aspects, the first composition can comprise about 1.5 mg to about 50 mg of the SERM, or an equivalent amount of a pharmaceutically acceptable salt thereof. In some aspects, the first composition can comprise about 1.5 mg to about 40 mg, about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of the SERM, or an equivalent amount of a pharmaceutically acceptable salt thereof.

In some aspects, the first composition can comprise about 2 mg to about 50 mg of the SERM, or an equivalent amount of a pharmaceutically acceptable salt thereof. In some aspects, the first composition can comprise about 2 mg to about 40 mg, about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of the SERM, or an equivalent amount of a pharmaceutically acceptable salt thereof.

In some aspects, the first composition can comprise about 2.5 mg to about 50 mg of the SERM, or an equivalent amount of a pharmaceutically acceptable salt thereof. In some aspects, the first composition can comprise about 2.5 mg to about 40 mg, about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of the SERM, or an equivalent amount of a pharmaceutically acceptable salt thereof.

In some aspects, the first composition can comprise about 3 mg to about 50 mg of the SERM, or an equivalent amount of a pharmaceutically acceptable salt thereof. In some aspects, the first composition can comprise about 3 mg to about 40 mg, about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of the SERM, or an equivalent amount of a pharmaceutically acceptable salt thereof.

In some aspects, the first composition can comprise about 4 mg to about 50 mg of the SERM, or an equivalent amount of a pharmaceutically acceptable salt thereof. In some aspects, the first composition can comprise about 4 mg to about 40 mg, about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of the SERM, or an equivalent amount of a pharmaceutically acceptable salt thereof.

In some aspects, the first composition can comprise about 5 mg to about 50 mg of the SERM, or an equivalent amount of a pharmaceutically acceptable salt thereof. In some aspects, the first composition can comprise about 5 mg to about 40 mg, about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, about 5 mg to about 5.5, about 5.5 mg to about 7.5 mg, about 5.5 mg to about 7 mg, about 5.5 to about 6.5 mg, about 5.5 to about 6 mg, about 6 mg to about 8 mg, about 6 mg to about 7.5 mg, about 6 mg to about 7 mg, or about 6 mg to about 6.5 mg of the SERM, or an equivalent amount of a pharmaceutically acceptable salt thereof.

In some aspects, the first composition can comprise about 8 mg to about 50 mg of the SERM, or an equivalent amount of a pharmaceutically acceptable salt thereof. In some aspects, the first composition can comprise about 8 mg to about 40 mg, about 8 mg to about 30 mg, about 8 mg to about 25 mg, about 8 mg to about 20 mg, about 8 mg to about 15 mg, about 8 mg to about 14 mg, about 8 mg to about 13 mg, about 8 mg to about 12 mg, about 8 mg to about 11 mg, about 8 mg to about 10 mg, about 8 mg to about 9 mg, about 9 mg to about 15 mg, about 9 mg to about 14 mg, about 9 mg to about 13 mg, about 9 mg to about 12 mg, about 9 mg to about 11 mg, or about 9 mg to About 10 mg of the SERM, or an equivalent amount of a pharmaceutically acceptable salt thereof.

In some aspects, the first composition can comprise about 10 mg to about 50 mg of the SERM, or an equivalent amount of a pharmaceutically acceptable salt thereof. In some aspects, the first composition can comprise about 10 mg to about 40 mg, about 10 mg to about 30 mg, about 10 mg to about 27.5 mg, about 10 mg to about 25 mg, about 10 mg to about 22.5 mg, about 10 mg to about 20 mg, about 10 mg to about 17.5 mg, about 10 mg to about 15 mg, about 11 mg to about 14 mg, or about 12 mg to about 13 mg of the SERM, or an equivalent amount of a pharmaceutically acceptable salt thereof.

In some aspects, the first composition can comprise about 20 mg to about 50 mg of the SERM, or an equivalent amount of a pharmaceutically acceptable salt thereof. In some aspects, the first composition can comprise about 20 mg to about 40 mg, about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, or about 20 mg to about 21 mg of the SERM, or an equivalent amount of a pharmaceutically acceptable salt thereof.

In some aspects, the first composition can comprise about 22.5 mg to about 50 mg of the SERM, or an equivalent amount of a pharmaceutically acceptable salt thereof. In some aspects, the first composition can comprise about 22.5 mg to about 45 mg, about 22.5 mg to about 40 mg, about 22.5 mg to about 35 mg, about 22.5 mg to about 30 mg, about 22.5 mg to about 29 mg, about 22.5 mg to about 28 mg, about 22.5 mg to about 27.5 mg, about 22.5 mg to about 27 mg, about 22.5 mg to about 26.5 mg, about 22.5 mg to about 26 mg, about 22.5 mg to about 25.5 mg, about 22.5 mg to about 25 mg, about 22.5 mg to about 24.5 mg, about 22.5 mg to about 24 mg, about 22.5 mg to about 23.5 mg, about 22.5 to about 23 mg, 23 mg about 27.5 mg, about 23 mg to about 27 mg, about 23 mg to about 26.5 mg, about 23 mg to about 26 mg, about 23 mg to about 25.5 mg, about 23 mg to about 25 mg, about 23 mg to about 23 mg, about 23 mg to about 24 mg, about 23 mg to about 23.5 mg, about 24 mg to about 27.5 mg, about 24 mg to about 27 mg, about 24 mg to about 26.5 mg, about 24 mg to about 26 mg, about 24 mg to about 25.5 mg, about 24 mg to about 25 mg, or about 24 mg to about 24.5 mg of the SERM, or an equivalent amount of a pharmaceutically acceptable salt thereof.

In some aspects, the first composition can comprise about 1 mg, about 1.5 mg, about 2 mg, about 2.5 mg, about 3 mg, about 3.125 mg, about 3.5 mg, about 4 mg, about 4.5 mg, about 5 mg, about 5.5 mg, about 6 mg, about 6.25 mg, about 6.5 mg, about 7 mg, about 7.5 mg, about 8 mg, about 8.5 mg, about 9 mg, about 9.5 mg, about 10 mg, about 12.5 mg, about 15 mg, about 20 mg, about 25 mg, about 30 mg, about 35 mg, about 40 mg, about 45 mg, about 50 mg of the SERM, or an equivalent amount of a pharmaceutically acceptable salt thereof.

In some aspects, the first composition can comprise about 1 mg to about 80 mg of enclomiphene, or an equivalent amount of a pharmaceutically acceptable salt thereof. In some aspects, the first composition can comprise about 1 mg to about 70 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of enclomiphene, or an equivalent amount of a pharmaceutically acceptable salt thereof.

In some aspects, the first composition can comprise about 1.5 mg to about 50 mg of enclomiphene, or an equivalent amount of a pharmaceutically acceptable salt thereof. In some aspects, the first composition can comprise about 1.5 mg to about 40 mg, about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of enclomiphene, or an equivalent amount of a pharmaceutically acceptable salt thereof.

In some aspects, the first composition can comprise about 2 mg to about 50 mg of enclomiphene, or an equivalent amount of a pharmaceutically acceptable salt thereof. In some aspects, the first composition can comprise about 2 mg to about 40 mg, about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of enclomiphene, or an equivalent amount of a pharmaceutically acceptable salt thereof.

In some aspects, the first composition can comprise about 2.5 mg to about 50 mg of enclomiphene, or an equivalent amount of a pharmaceutically acceptable salt thereof. In some aspects, the first composition can comprise about 2.5 mg to about 40 mg, about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of enclomiphene, or an equivalent amount of a pharmaceutically acceptable salt thereof.

In some aspects, the first composition can comprise about 3 mg to about 50 mg of enclomiphene, or an equivalent amount of a pharmaceutically acceptable salt thereof. In some aspects, the first composition can comprise about 3 mg to about 40 mg, about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of enclomiphene, or an equivalent amount of a pharmaceutically acceptable salt thereof.

In some aspects, the first composition can comprise about 4 mg to about 50 mg of enclomiphene, or an equivalent amount of a pharmaceutically acceptable salt thereof. In some aspects, the first composition can comprise about 4 mg to about 40 mg, about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of enclomiphene, or an equivalent amount of a pharmaceutically acceptable salt thereof.

In some aspects, the first composition can comprise about 5 mg to about 50 mg of enclomiphene, or an equivalent amount of a pharmaceutically acceptable salt thereof. In some aspects, the first composition can comprise about 5 mg to about 40 mg, about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, about 5 mg to about 5.5, about 5.5 mg to about 7.5 mg, about 5.5 mg to about 7 mg, about 5.5 to about 6.5 mg, about 5.5 to about 6 mg, about 6 mg to about 8 mg, about 6 mg to about 7.5 mg, about 6 mg to about 7 mg, or about 6 mg to about 6.5 mg of enclomiphene, or an equivalent amount of a pharmaceutically acceptable salt thereof.

In some aspects, the first composition can comprise about 8 mg to about 50 mg of enclomiphene, or an equivalent amount of a pharmaceutically acceptable salt thereof. In some aspects, the first composition can comprise about 8 mg to about 40 mg, about 8 mg to about 30 mg, about 8 mg to about 25 mg, about 8 mg to about 20 mg, about 8 mg to about 15 mg, about 8 mg to about 14 mg, about 8 mg to about 13 mg, about 8 mg to about 12 mg, about 8 mg to about 11 mg, about 8 mg to about 10 mg, about 8 mg to about 9 mg, about 9 mg to about 15 mg, about 9 mg to about 14 mg, about 9 mg to about 13 mg, about 9 mg to about 12 mg, about 9 mg to about 11 mg, or about 9 mg to about 10 mg of enclomiphene, or an equivalent amount of a pharmaceutically acceptable salt thereof.

In some aspects, the first composition can comprise about 10 mg to about 50 mg of enclomiphene, or an equivalent amount of a pharmaceutically acceptable salt thereof. In some aspects, the first composition can comprise about 10 mg to about 40 mg, about 10 mg to about 30 mg, about 10 mg to about 27.5 mg, about 10 mg to about 25 mg, about 10 mg to about 22.5 mg, about 10 mg to about 20 mg, about 10 mg to about 17.5 mg, about 10 mg to about 15 mg, about 11 mg to about 14 mg, or about 12 mg to about 13 mg of enclomiphene, or an equivalent amount of a pharmaceutically acceptable salt thereof.

In some aspects, the first composition can comprise about 20 mg to about 50 mg of enclomiphene, or an equivalent amount of a pharmaceutically acceptable salt thereof. In some aspects, the first composition can comprise about 20 mg to about 40 mg, about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, or about 20 mg to about 21 mg of enclomiphene, or an equivalent amount of a pharmaceutically acceptable salt thereof.

In some aspects, the first composition can comprise about 22.5 mg to about 50 mg of enclomiphene, or an equivalent amount of a pharmaceutically acceptable salt thereof. In some aspects, the first composition can comprise about 22.5 mg to about 45 mg, about 22.5 mg to about 40 mg, about 22.5 mg to about 35 mg, about 22.5 mg to about 30 mg, about 22.5 mg to about 29 mg, about 22.5 mg to about 28 mg, about 22.5 mg to about 27.5 mg, about 22.5 mg to about 27 mg, about 22.5 mg to about 26.5 mg, about 22.5 mg to about 26 mg, about 22.5 mg to about 25.5 mg, about 22.5 mg to about 25 mg, about 22.5 mg to about 24.5 mg, about 22.5 mg to about 24 mg, about 22.5 mg to about 23.5 mg, about 22.5 to about 23 mg, 23 mg about 27.5 mg, about 23 mg to about 27 mg, about 23 mg to about 26.5 mg, about 23 mg to about 26 mg, about 23 mg to about 25.5 mg, about 23 mg to about 25 mg, about 23 mg to about 23 mg, about 23 mg to about 24 mg, about 23 mg to about 23.5 mg, about 24 mg to about 27.5 mg, about 24 mg to about 27 mg, about 24 mg to about 26.5 mg, about 24 mg to about 26 mg, about 24 mg to about 25.5 mg, about 24 mg to about 25 mg, or about 24 mg to about 24.5 mg of enclomiphene, or an equivalent amount of a pharmaceutically acceptable salt thereof.

In some aspects, the first composition can comprise about 1 mg, about 1.5 mg, about 2 mg, about 2.5 mg, about 3 mg, about 3.125 mg, about 3.5 mg, about 4 mg, about 4.5 mg, about 5 mg, about 5.5 mg, about 6 mg, about 6.25 mg, about 6.5 mg, about 7 mg, about 7.5 mg, about 8 mg, about 8.5 mg, about 9 mg, about 9.5 mg, about 10 mg, about 12.5 mg, about 15 mg, about 20 mg, about 25 mg, about 30 mg, about 35 mg, about 40 mg, about 45 mg, about 50 mg of enclomiphene, or an equivalent amount of a pharmaceutically acceptable salt thereof.

In some aspects, the first composition can comprise about 1 mg to about 120 mg of toremifene, or an equivalent amount of a pharmaceutically acceptable salt thereof. In some aspects, the first composition can comprise about 1 mg to about 110 mg, about 1 mg to about 100 mg, about 1 mg to about 90 mg, about 1 mg to about 80 mg, about 1 mg to about 70 mg, about 1 mg to about 60 mg, about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of toremifene, or an equivalent amount of a pharmaceutically acceptable salt thereof.

In some aspects, the first composition can comprise about 2 mg to about 120 mg of toremifene, or an equivalent amount of a pharmaceutically acceptable salt thereof. In some aspects, the first composition can comprise about 2 mg to about 110 mg, about 2 mg to about 100 mg, about 2 mg to about 90 mg, about 2 mg to about 80 mg, about 2 mg to about 70 mg, about 2 mg to about 60 mg, about 2 mg to about 50 mg, about 2 mg to about 40 mg, about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of toremifene, or an equivalent amount of a pharmaceutically acceptable salt thereof.

In some aspects, the first composition can comprise about 5 mg to about 120 mg of toremifene, or an equivalent amount of a pharmaceutically acceptable salt thereof. In some aspects, the first composition can comprise about 5 mg to about 110 mg, about 5 mg to about 100 mg, about 5 mg to about 90 mg, about 5 mg to about 80 mg, about 5 mg to about 70 mg, about 5 mg to about 60 mg, about 5 mg to about 50 mg, about 5 mg to about 40 mg, about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, about 5 mg to about 5.5, about 5.5 mg to about 7.5 mg, about 5.5 mg to about 7 mg, about 5.5 to about 6.5 mg, about 5.5 to about 6 mg, about 6 mg to about 8 mg, about 6 mg to about 7.5 mg, about 6 mg to about 7 mg, or about 6 mg to about 6.5 mg of toremifene, or an equivalent amount of a pharmaceutically acceptable salt thereof.

In some aspects, the first composition can comprise about 10 mg to about 120 mg of toremifene, or an equivalent amount of a pharmaceutically acceptable salt thereof. In some aspects, the first composition can comprise about 10 mg to about 110 mg, about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, about 10 mg to about 27.5 mg, about 10 mg to about 25 mg, about 10 mg to about 22.5 mg, about 10 mg to about 20 mg, about 10 mg to about 17.5 mg, about 10 mg to about 15 mg, about 11 mg to about 14 mg, or about 12 mg to about 13 mg of toremifene, or an equivalent amount of a pharmaceutically acceptable salt thereof.

In some aspects, the first composition can comprise about 20 mg to about 120 mg of toremifene, or an equivalent amount of a pharmaceutically acceptable salt thereof. In some aspects, the first composition can comprise about 20 mg to about 110 mg, about 20 mg to about 100 mg, about 20 mg to about 90 mg, about 20 mg to about 80 mg, about 20 mg to about 70 mg, about 20 mg to about 60 mg, about 20 mg to about 50 mg, about 20 mg to about 40 mg, about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, or about 20 mg to about 21 mg of toremifene, or an equivalent amount of a pharmaceutically acceptable salt thereof.

In some aspects, the composition can comprise about 40 mg to about 120 mg of toremifene, or an equivalent amount of a pharmaceutically acceptable salt thereof. In some aspects, the composition can comprise about 40 mg to about 110 mg, about 40 mg to about 100 mg, about 40 mg to about 90 mg, about 40 mg to about 80 mg, about 40 mg to about 70 mg, about 40 mg to about 60 mg, about 50 mg to about 120 mg, about 50 mg to about 100 mg, about 50 mg to about 90 mg, about 50 mg to about 80 mg, about 50 mg to about 70 mg, or about 60 mg of toremifene, or an equivalent amount of a pharmaceutically acceptable salt thereof.

In some aspects, the first composition can comprise about 1 mg, about 1.5 mg, about 2 mg, about 2.5 mg, about 3 mg, about 3.125 mg, about 3.5 mg, about 4 mg, about 4.5 mg, about 5 mg, about 5.5 mg, about 6 mg, about 6.25 mg, about 6.5 mg, about 7 mg, about 7.5 mg, about 8 mg, about 8.5 mg, about 9 mg, about 9.5 mg, about 10 mg, about 12.5 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 110 mg, about 120 mg of toremifene, or an equivalent amount of a pharmaceutically acceptable salt thereof.

In some aspects, the first composition can further comprise about 1 mg to about 60 mg of the neurosteroid. In some aspects, the first composition can further comprise about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of the neurosteroid.

In some aspects, the first composition can further comprise about 1.5 mg to about 40 mg of the neurosteroid. In some aspects, the first composition can further comprise about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of the neurosteroid.

In some aspects, the first composition can further comprise about 2 mg to about 40 mg of the neurosteroid. In some aspects, the first composition can further comprise about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of the neurosteroid.

In some aspects, the first composition can further comprise about 2.5 mg to about 40 mg of the neurosteroid. In some aspects, the first composition can further comprise about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of the neurosteroid.

In some aspects, the first composition can further comprise about 3 mg to about 40 mg of the neurosteroid. In some aspects, the first composition can further comprise about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of the neurosteroid.

In some aspects, the first composition can further comprise about 4 mg to about 40 mg of the neurosteroid. In some aspects, the first composition can further comprise about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of the neurosteroid.

In some aspects, the first composition can further comprise about 4.5 mg to about 40 mg of the neurosteroid. In some aspects, the first composition can further comprise about 4.5 mg to about 30 mg, about 4.5 mg to about 25 mg, about 4.5 mg to about 20 mg, about 4.5 mg to about 17.5 mg, about 4.5 mg to about 15 mg, about 4.5 mg to about 12.5 mg, about 4.5 mg to about 10 mg, about 4.5 mg to about 9 mg, about 4.5 mg to about 8 mg, about 4.5 mg to about 7.5 mg, about 4.5 mg to about 7 mg, about 4.5 mg to about 6.5 mg, about 4.5 mg to about 6 mg, about 4.5 mg to about 5.5 mg, or about 4.5 mg to about 5 mg of the neurosteroid.

In some aspects, the first composition can further comprise about 5 mg to about 40 mg of the neurosteroid. In some aspects, the first composition can further comprise about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, or about 5 mg to about 5.5 of the neurosteroid.

In some aspects, the first composition can further comprise about 8 mg to about 40 mg of the neurosteroid. In some aspects, the first composition can further comprise about 8 mg to about 30 mg, about 8 mg to about 25 mg, about 8 mg to about 20 mg, about 8 mg to about 17.5 mg, about 8 mg to about 15 mg, about 8 mg to about 12.5 mg, about 8 mg to about 11.5 mg, about 8 mg to about 11 mg, about 8 mg to about 10.5 mg, about 8 mg to about 10 mg, about 8 mg to about 9.5 mg, about 8 mg to about 9 mg, about 9 mg to about 15 mg, about 9 mg to about 12.5 mg, about 9 mg to about 11.5 mg, about 9 mg to about 11 mg, about 9 mg to about 10.5 mg, about 9 mg to about 10 mg, or about 9 mg to about 9.5 mg of the neurosteroid.

In some aspects, the first composition can further comprise about 10 mg to about 40 mg of the neurosteroid. In some aspects, the first composition can further comprise about 10 mg to about 30 mg, about 10 mg to about 25 mg, about 10 mg to about 20 mg, about 10 mg to about 17.5 mg, about 10 mg to about 15 mg, about 10 mg to about 12.5 mg, about 10 mg to about 11.5 mg, about 10 mg to about 11 mg, or about 10 mg to about 10.5 mg of the neurosteroid.

In some aspects, the first composition can further comprise about 12 mg to about 40 mg of the neurosteroid. In some aspects, the first composition can further comprise about 12 mg to about 30 mg, about 12 mg to about 25 mg, about 12 mg to about 20 mg, about 12 mg to about 17 mg, about 12 mg to about 15 mg, about 12 mg to about 14.5 mg, about 12 mg to about 14 mg, about 12 mg to about 13.5 mg, or about 12 mg to about 13 mg of the neurosteroid.

In some aspects, the first composition can further comprise about 14 mg to about 40 mg of the neurosteroid. In some aspects, the first composition can further comprise about 14 mg to about 30 mg, about 14 mg to about 25 mg, about 14 mg to about 20 mg, about 14 mg to about 17.5 mg, about 14 mg to about 16 mg, about 14 mg to about 15.5 mg, about 14 mg to about 15 mg, or about 14 mg to about 14.5 mg of the neurosteroid.

In some aspects, the first composition can further comprise about 15 mg to about 40 mg of the neurosteroid. In some aspects, the first composition can further comprise about 15 mg to about 30 mg, about 15 mg to about 27.5 mg, about 15 mg to about 25 mg, about 15 mg to about 22.5 mg, about 15 mg to about 20 mg, about 15 mg to about 17.5 mg, about 15 mg to about 16.5 mg, about 15 mg to about 16 mg, or about 15 mg to about 15.5 mg of the neurosteroid.

In some aspects, the first composition can further comprise about 17.5 mg to about 40 mg of the neurosteroid. In some aspects, the first composition can further comprise about 17.5 mg to about 30 mg, about 17.5 mg to about 27.5 mg, about 17.5 mg to about 25 mg, about 17.5 mg to about 22.5 mg, about 17.5 mg to about 20 mg, about 17.5 mg to about 18 mg of the neurosteroid.

In some aspects, the first composition can further comprise about 20 mg to about 40 mg of the neurosteroid. In some aspects, the first composition can further comprise about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, about 20 mg to about 21 mg, or about 20 mg to about 20.5 mg of the neurosteroid.

In some aspects, the first composition can further comprise about 25 mg to about 40 mg of the neurosteroid. In some aspects, the first composition can further comprise about 25 mg to about 35 mg, about 25 mg to about 30 mg, about 25 mg to about 29 mg, about 25 mg to about 28 mg, about 25 mg to about 27 mg, about 25 mg to about 26.5 mg, about 25 mg to about 26 mg, or about 25 mg to about 25.5 mg of the neurosteroid.

In some aspects, the first composition can further comprise about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 12.5 mg, about 15 mg, about 17.5 mg, about 20 mg, about 25 mg, about 30 mg, about 35 mg, about 40 mg of the neurosteroid.

In some aspects, the first composition can further comprise about 1 mg to about 60 mg of pregnenolone. In some aspects, the first composition can further comprise about 1 mg to about 50 mg, about 1 mg to about 40 mg, about 1 mg to about 30 mg, about 1 mg to about 25 mg, about 1 mg to about 20 mg, about 1 mg to about 17.5 mg, about 1 mg to about 15 mg, about 1 mg to about 12.5 mg, about 1 mg to about 10 mg, about 1 mg to about 9 mg, about 1 mg to about 8 mg, about 1 mg to about 7.5 mg, about 1 mg to about 7 mg, about 1 mg to about 6.5 mg, about 1 mg to about 6 mg, about 1 mg to about 5.5 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, or about 1 mg to about 1.5 mg of pregnenolone.

In some aspects, the first composition can further comprise about 1.5 mg to about 40 mg of pregnenolone. In some aspects, the first composition can further comprise about 1.5 mg to about 30 mg, about 1.5 mg to about 25 mg, about 1.5 mg to about 20 mg, about 1.5 mg to about 17.5 mg, about 1.5 mg to about 15 mg, about 1.5 mg to about 12.5 mg, about 1.5 mg to about 10 mg, about 1.5 mg to about 9 mg, about 1.5 mg to about 8 mg, about 1.5 mg to about 7.5 mg, about 1.5 mg to about 7 mg, about 1.5 mg to about 6.5 mg, about 1.5 mg to about 6 mg, about 1.5 mg to about 5.5 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, or about 1.5 mg to about 2 mg of pregnenolone.

In some aspects, the first composition can further comprise about 2 mg to about 40 mg of pregnenolone. In some aspects, the first composition can further comprise about 2 mg to about 30 mg, about 2 mg to about 25 mg, about 2 mg to about 20 mg, about 2 mg to about 17.5 mg, about 2 mg to about 15 mg, about 2 mg to about 12.5 mg, about 2 mg to about 10 mg, about 2 mg to about 9 mg, about 2 mg to about 8 mg, about 2 mg to about 7.5 mg, about 2 mg to about 7 mg, about 2 mg to about 6.5 mg, about 2 mg to about 6 mg, about 2 mg to about 5.5 mg, about 2 mg to about 5 mg, about 2 mg to about 4.5 mg, about 2 mg to about 4 mg, about 2 mg to about 3.5 mg, about 2 mg to about 3 mg, or about 2 mg to about 2.5 mg of pregnenolone.

In some aspects, the first composition can further comprise about 2.5 mg to about 40 mg of pregnenolone. In some aspects, the first composition can further comprise about 2.5 mg to about 30 mg, about 2.5 mg to about 25 mg, about 2.5 mg to about 20 mg, about 2.5 mg to about 17.5 mg, about 2.5 mg to about 15 mg, about 2.5 mg to about 12.5 mg, about 2.5 mg to about 10 mg, about 2.5 mg to about 9 mg, about 2.5 mg to about 8 mg, about 2.5 mg to about 7.5 mg, about 2.5 mg to about 7 mg, about 2.5 mg to about 6.5 mg, about 2.5 mg to about 6 mg, about 2.5 mg to about 5.5 mg, about 2.5 mg to about 5 mg, about 2.5 mg to about 4.5 mg, about 2.5 mg to about 4 mg, about 2.5 mg to about 3.5 mg, or about 2.5 mg to about 3 mg of pregnenolone.

In some aspects, the first composition can further comprise about 3 mg to about 40 mg of pregnenolone. In some aspects, the first composition can further comprise about 3 mg to about 30 mg, about 3 mg to about 25 mg, about 3 mg to about 20 mg, about 3 mg to about 17.5 mg, about 3 mg to about 15 mg, about 3 mg to about 12.5 mg, about 3 mg to about 10 mg, about 3 mg to about 9 mg, about 3 mg to about 8 mg, about 3 mg to about 7.5 mg, about 3 mg to about 7 mg, about 3 mg to about 6.5 mg, about 3 mg to about 6 mg, about 3 mg to about 5.5 mg, about 3 mg to about 5 mg, about 3 mg to about 4.5 mg, about 3 mg to about 4 mg, or about 3 mg to about 3.5 mg of pregnenolone.

In some aspects, the first composition can further comprise about 4 mg to about 40 mg of pregnenolone. In some aspects, the first composition can further comprise about 4 mg to about 30 mg, about 4 mg to about 25 mg, about 4 mg to about 20 mg, about 4 mg to about 17.5 mg, about 4 mg to about 15 mg, about 4 mg to about 12.5 mg, about 4 mg to about 10 mg, about 4 mg to about 9 mg, about 4 mg to about 8 mg, about 4 mg to about 7.5 mg, about 4 mg to about 7 mg, about 4 mg to about 6.5 mg, about 4 mg to about 6 mg, about 4 mg to about 5.5 mg, about 4 mg to about 5 mg, or about 4 mg to about 4.5 mg of pregnenolone.

In some aspects, the first composition can further comprise about 4.5 mg to about 40 mg of pregnenolone. In some aspects, the first composition can further comprise about 4.5 mg to about 30 mg, about 4.5 mg to about 25 mg, about 4.5 mg to about 20 mg, about 4.5 mg to about 17.5 mg, about 4.5 mg to about 15 mg, about 4.5 mg to about 12.5 mg, about 4.5 mg to about 10 mg, about 4.5 mg to about 9 mg, about 4.5 mg to about 8 mg, about 4.5 mg to about 7.5 mg, about 4.5 mg to about 7 mg, about 4.5 mg to about 6.5 mg, about 4.5 mg to about 6 mg, about 4.5 mg to about 5.5 mg, or about 4.5 mg to about 5 mg of pregnenolone.

In some aspects, the first composition can further comprise about 5 mg to about 40 mg of pregnenolone. In some aspects, the first composition can further comprise about 5 mg to about 30 mg, about 5 mg to about 25 mg, about 5 mg to about 20 mg, about 5 mg to about 17.5 mg, about 5 mg to about 15 mg, about 5 mg to about 12.5 mg, about 5 mg to about 10 mg, about 5 mg to about 9 mg, about 5 mg to about 8 mg, about 5 mg to about 7.5 mg, about 5 mg to about 7 mg, about 5 mg to about 6.5 mg, about 5 mg to about 6 mg, or about 5 mg to about 5.5 of pregnenolone.

In some aspects, the first composition can further comprise about 8 mg to about 40 mg of pregnenolone. In some aspects, the first composition can further comprise about 8 mg to about 30 mg, about 8 mg to about 25 mg, about 8 mg to about 20 mg, about 8 mg to about 17.5 mg, about 8 mg to about 15 mg, about 8 mg to about 12.5 mg, about 8 mg to about 11.5 mg, about 8 mg to about 11 mg, about 8 mg to about 10.5 mg, about 8 mg to about 10 mg, about 8 mg to about 9.5 mg, about 8 mg to about 9 mg, about 9 mg to about 15 mg, about 9 mg to about 12.5 mg, about 9 mg to about 11.5 mg, about 9 mg to about 11 mg, about 9 mg to about 10.5 mg, about 9 mg to about 10 mg, or about 9 mg to about 9.5 mg of pregnenolone.

In some aspects, the first composition can further comprise about 10 mg to about 40 mg of pregnenolone. In some aspects, the first composition can further comprise about 10 mg to about 30 mg, about 10 mg to about 25 mg, about 10 mg to about 20 mg, about 10 mg to about 17.5 mg, about 10 mg to about 15 mg, about 10 mg to about 12.5 mg, about 10 mg to about 11.5 mg, about 10 mg to about 11 mg, or about 10 mg to about 10.5 mg of pregnenolone.

In some aspects, the first composition can further comprise about 12 mg to about 40 mg of pregnenolone. In some aspects, the first composition can further comprise about 12 mg to about 30 mg, about 12 mg to about 25 mg, about 12 mg to about 20 mg, about 12 mg to about 17 mg, about 12 mg to about 15 mg, about 12 mg to about 14.5 mg, about 12 mg to about 14 mg, about 12 mg to about 13.5 mg, or about 12 mg to about 13 mg of pregnenolone.

In some aspects, the first composition can further comprise about 14 mg to about 40 mg of pregnenolone. In some aspects, the first composition can further comprise about 14 mg to about 30 mg, about 14 mg to about 25 mg, about 14 mg to about 20 mg, about 14 mg to about 17.5 mg, about 14 mg to about 16 mg, about 14 mg to about 15.5 mg, about 14 mg to about 15 mg, or about 14 mg to about 14.5 mg of pregnenolone.

In some aspects, the first composition can further comprise about 15 mg to about 40 mg of pregnenolone. In some aspects, the first composition can further comprise about 15 mg to about 30 mg, about 15 mg to about 27.5 mg, about 15 mg to about 25 mg, about 15 mg to about 22.5 mg, about 15 mg to about 20 mg, about 15 mg to about 17.5 mg, about 15 mg to about 16.5 mg, about 15 mg to about 16 mg, or about 15 mg to about 15.5 mg of pregnenolone.

In some aspects, the first composition can further comprise about 17.5 mg to about 40 mg of pregnenolone. In some aspects, the first composition can further comprise about 17.5 mg to about 30 mg, about 17.5 mg to about 27.5 mg, about 17.5 mg to about 25 mg, about 17.5 mg to about 22.5 mg, about 17.5 mg to about 20 mg, about 17.5 mg to about 18 mg of pregnenolone.

In some aspects, the first composition can further comprise about 20 mg to about 40 mg of pregnenolone. In some aspects, the first composition can further comprise about 20 mg to about 30 mg, about 20 mg to about 29 mg, about 20 mg to about 28 mg, about 20 mg to about 27 mg, about 20 mg to about 26.5 mg, about 20 mg to about 26 mg, about 20 mg to about 25.5 mg, about 20 mg to about 25 mg, about 20 mg to about 24.5 mg, about 20 mg to about 24 mg, about 20 mg to about 23.5 mg, about 20 mg to about 23 mg, about 20 mg to about 22.5 mg, about 20 mg to about 22 mg, about 20 mg to about 21.5 mg, about 20 mg to about 21 mg, or about 20 mg to about 20.5 mg of pregnenolone.

In some aspects, the first composition can further comprise about 25 mg to about 40 mg of pregnenolone. In some aspects, the first composition can further comprise about 25 mg to about 35 mg, about 25 mg to about 30 mg, about 25 mg to about 29 mg, about 25 mg to about 28 mg, about 25 mg to about 27 mg, about 25 mg to about 26.5 mg, about 25 mg to about 26 mg, or about 25 mg to about 25.5 mg of pregnenolone.

In some aspects, the first composition can further comprise about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 12.5 mg, about 15 mg, about 17.5 mg, about 20 mg, about 25 mg, about 30 mg, about 35 mg, about 40 mg of pregnenolone.

In some aspects, the first composition can further comprise about 1.5 mg of the SERM, or an equivalent amount of a pharmaceutically acceptable salt thereof, and about 5 mg of the neurosteroid. In some aspects, the first composition can further comprise about 2 mg of the SERM, or an equivalent amount of a pharmaceutically acceptable salt thereof, and about 5 mg of the neurosteroid; about 3.125 mg of the SERM, or an equivalent amount of a pharmaceutically acceptable salt thereof, and about 2.5 mg of the neurosteroid; about 3.125 mg of the SERM, or an equivalent amount of a pharmaceutically acceptable salt thereof, and about 5 mg of the neurosteroid; about 4 mg of the SERM, or an equivalent amount of a pharmaceutically acceptable salt thereof, and about 5 mg of the neurosteroid; about 6.25 mg of the SERM, or an equivalent amount of a pharmaceutically acceptable salt thereof, and about 5 mg of the neurosteroid; about 12.5 mg of the SERM, or an equivalent amount of a pharmaceutically acceptable salt thereof, and about 10 mg of the neurosteroid; about 25 mg of the SERM, or an equivalent amount of a pharmaceutically acceptable salt thereof, and about 20 mg of the neurosteroid; or about 50 mg of the SERM, or an equivalent amount of a pharmaceutically acceptable salt thereof, and about 40 mg of the neurosteroid.

In some aspects, the first composition can further comprise about 1.5 mg of enclomiphene, or an equivalent amount of a pharmaceutically acceptable salt thereof, and about 5 mg of pregnenolone. In some aspects, the first composition can further comprise about 2 mg of enclomiphene, or an equivalent amount of a pharmaceutically acceptable salt thereof, and about 5 mg of pregnenolone; about 3.125 mg of enclomiphene, or an equivalent amount of a pharmaceutically acceptable salt thereof, and about 2.5 mg of pregnenolone; about 3.125 mg of enclomiphene, or an equivalent amount of a pharmaceutically acceptable salt thereof, and about 5 mg of pregnenolone; about 4 mg of enclomiphene, or an equivalent amount of a pharmaceutically acceptable salt thereof, and about 5 mg of pregnenolone; about 6.25 mg of enclomiphene, or an equivalent amount of a pharmaceutically acceptable salt thereof, and about 5 mg of pregnenolone; about 12.5 mg of enclomiphene, or an equivalent amount of a pharmaceutically acceptable salt thereof, and about 10 mg of pregnenolone; about 25 mg of enclomiphene, or an equivalent amount of a pharmaceutically acceptable salt thereof, and about 20 mg of pregnenolone; or about 50 mg of enclomiphene, or an equivalent amount of a pharmaceutically acceptable salt thereof, and about 40 mg of pregnenolone.

In some aspects, the first composition can also include the excipients in the amounts and ranges disclosed above in the disclosure related to the pharmaceutical composition.

In some aspects, the second composition of the pharmaceutical combination can comprise about 100 mg to about 1,500 mg of testosterone. In some aspects, the second composition of the pharmaceutical combination can comprise about 100 mg to about 1200 mg, about 100 mg to about 1,100 mg, about 100 mg to about 1,000 mg, about 100 mg to about 900 mg, about 100 mg to about 800 mg, about 100 mg to about 700 mg, about 100 mg to about 600 mg, about 100 mg to about 500 mg, about 100 mg to about 400 mg, about 100 mg to about 300 mg, or about 150 mg to about 250 mg of testosterone.

In some aspects, the second composition can comprise about 200 mg to about 1,200 mg of testosterone. In some aspects, the second composition can comprise about 200 mg to about 1,100 mg, about 200 mg to about 1,000 mg, about 200 mg to about 900 mg, about 200 mg to about 800 mg, about 200 mg to about 700 mg, about 200 mg to about 600 mg, about 200 mg to about 500 mg, about 200 mg to about 400 mg, or about 200 mg to about 300 mg of testosterone.

In some aspects, the second composition can comprise about 400 mg to about 1,200 mg of testosterone. In some aspects, the second composition can comprise about 400 mg to about 1,100 mg, about 400 mg to about 1,000 mg, about 400 mg to about 900 mg, about 400 mg to about 800 mg, about 400 mg to about 700 mg, 400 mg to about 600 mg, or about 400 mg to about 500 mg of testosterone.

In some aspects, the second composition can comprise about 600 mg to about 1,200 mg of testosterone. In some aspects, the second composition can comprise about 600 mg to about 1,100 mg, about 600 mg to about 1,000 mg, about 600 mg to about 900 mg, about 600 mg to about 800 mg, or about 600 mg to about 700 mg of testosterone.

In some aspects, the second composition can comprise about 800 mg to about 1,200 mg of testosterone. In some aspects, the second composition can comprise about 800 mg to about 1,100 mg, about 800 mg to about 1,000 mg, or about 800 mg to about 900 mg of testosterone.

In some aspects, the second composition can comprise about 1,000 mg to about 1,200 mg or about 1,000 mg to about 1,100 mg of testosterone.

In some aspects, the second composition can comprise about 100 mg, about 200 mg, about 300 mg, about 400 mg, about 500 mg, about 600 mg, about 700 mg, about 800 mg, about 900 mg, about 1,000 mg, about 1,100 mg, about 1,200 of testosterone.

In some aspects, the testosterone can be natural or native testosterone (also known as testosterone base or unmodified testosterone or unesterified testosterone) or an isomer or derivative thereof. In some aspects, the testosterone can be native testosterone. In some aspects, the testosterone is a testosterone ester.

Without wishing to be bound to any particular theory, it is believed that native testosterone or a short-acting testosterone ester is preferable to a long-acting testosterone, such as an intramuscular or subcutaneous injection of a testosterone ester, in a combination therapy with a SERM, e.g., enclomiphene or an equivalent amount of a pharmaceutically acceptable salt thereof, because long-acting testosterone esters create artificially sustained levels of free testosterone resulting in reduced LH and FSH secretion that the estrogen receptor antagonist activity by a SERM cannot overcome. For example, testosterone enanthate or cypionate combined with enclomiphene would not increase LH or FSH levels to within normal levels and/or cause reduction in testicular function, size, and volume, reduced fertility, and increased risk of dependence. In contrast, native testosterone has a shorter half-life and thus the estrogen receptor antagonist activity by a SERM can stimulate LH and FSH secretion despite the use of exogenous testosterone, thereby counteracting the negative feedback inhibition of testosterone therapy and enhancing total testosterone levels by preserving endogenous testosterone production.

In some aspects, the second composition can comprise an oil. In some aspects, the oil can be selected from the group consisting of canola oil, cottonseed oil, hydrogenated cottonseed oil, peanut oil, corn oil, olive oil, soybean oil, hydrogenated soybean oil, sunflower oil, safflower oil, coconut oil, palm oil, hydrogenated palm oil, linseed oil, tung oil, castor oil, rapeseed oil, sesame oil, and combinations thereof. In some aspects, the oil can be safflower oil.

In some aspects, the oil can be present in amounts of about 10% to about 80% by weight of the second composition. In some aspects, the oil can be present in amounts of about 10% to about 70%, about 10% to about 60%, about 10% to about 50%, about 10% to about 40%, about 10% to about 30%, or about 10% to about 20% by weight of the second composition.

In some aspects, the oil can be present in amounts of about 20% to about 80% by weight of the second composition. In some aspects, the oil can be present in amounts of about 20% to about 70%, about 20% to about 60%, about 20% to about 50%, about 20% to about 40%, or about 20% to about 30% by weight of the second composition.

In some aspects, the oil can be present in amounts of about 30% to about 80% by weight of the second composition. In some aspects, the oil can be present in amounts of about 30% to about 70%, about 30% to about 60%, about 30% to about 50%, or about 30% to about 40% by weight of the second composition.

In some aspects, the oil can be present in amounts of about 40% to about 80% by weight of the second composition. In some aspects, the oil can be present in amounts of about 40% to about 70%, about 40% to about 60%, or about 40% to about 50% by weight of the second composition.

In some aspects, the oil can be present in amounts of about 50% to about 80% by weight of the second composition. In some aspects, the oil can be present in amounts of about 50% to about 70%, or about 50% to about 60% by weight of the second composition.

In some aspects, the oil can be present in amounts of about 60% to about 80% by weight of the pharmaceutical combination. In some aspects, the oil can be present in amounts of about 60% to about 70% by weight of the second composition.

In some aspects, the oil can be present in amounts of about 70% to about 80% by weight of the second composition.

In some aspects, the second composition can comprise a filler. In some aspects, the filler can be selected from the group consisting of cellulose and cellulose derivatives, microcrystalline cellulose, hydroxypropyl cellulose, lactose, calcium carbonate, calcium bicarbonate, calcium phosphate, dibasic calcium phosphate, calcium sulfate, calcium silicate, cellulose powders, dextrose, dextrates, dextrans, starches, pregelatinized starches, sucrose, xylitol, lactitol, sorbitol, sodium bicarbonate, sodium chloride, polyethylene glycol, and combinations thereof. In some aspects, the filler can be cellulose.

In some aspects, the filler can be present in amounts of about 10% to about 90% by weight of the second composition. In some aspects, the filler can be present in amounts of about 10% to about 80%, about 10% to about 70%, about 10% to about 60%, about 10% to about 50%, about 10% to about 40%, about 10% to about 30%, or about 10% to about 20% by weight of the second composition.

In some aspects, the filler can be present in amounts of about 20% to about 90% by weight of the second composition. In some aspects, the filler can be present in amounts of about 20% to about 80%, about 20% to about 70%, about 20% to about 60%, about 20% to about 50%, about 20% to about 40%, or about 20% to about 30% by weight of the second composition.

In some aspects, the filler can be present in amounts of about 30% to about 90% by weight of the second composition. In some aspects, the filler can be present in amounts of about 30% to about 80%, about 30% to about 70%, about 30% to about 60%, about 30% to about 50%, or about 30% to about 40% by weight of the second composition.

In some aspects, the filler can be present in amounts of about 40% to about 90% by weight of the second composition. In some aspects, the filler can be present in amounts of about 40% to about 80%, about 40% to about 70%, about 40% to about 60%, or about 40% to about 50% by weight of the second composition.

In some aspects, the filler can be present in amounts of about 50% to about 90% by weight of the second composition. In some aspects, the filler can be present in amounts of about 50% to about 80%, about 50% to about 70%, or about 50% to about 60% by weight of the second composition.

In some aspects, the filler can be present in amounts of about 60% to about 90% by weight of the second composition. In some aspects, the filler can be present in amounts of about 60% to about 80%, or about 60% to about 70% by weight of the second composition.

In some aspects, the filler can be present in amounts of about 70% to about 90% by weight of the second composition. In some aspects, the filler can be present in amounts of about 70% to about 80% by weight of the second composition. In some aspects, the filler can be present in amounts of about 80% to about 90% by weight of the second composition.

In some aspects, the second composition can further comprise a lubricant. In some aspects, the lubricant can be selected from the group consisting of stearic acid, calcium hydroxide, talc, corn starch, sodium stearyl fumerate, stearic acid, sodium oleate, sodium stearate, sodium benzoate, sodium acetate, sodium chloride, magnesium stearate, zinc stearate, waxes, and combinations thereof. In some aspects, the lubricant can be magnesium stearate.

In some aspects, the lubricant can be present in amounts of about 0.01% to about 10% by weight of the second composition. In some aspects, the lubricant can be present in amounts of about 0.01% to about 9%, about 0.01% to about 8%, about 0.01% to about 7%, about 0.010% to about 6%, about 0.010% to about 5%, about 0.010% to about 4%, about 0.01% to about 3%, about 0.01% to about 2%, about 0.01% to about 1%, about 0.01% to about 0.9%, about 0.01% to about 0.8%, about 0.01% to about 0.7%, about 0.01% to about 0.6%, about 0.01% to about 0.5%, about 0.01% to about 0.4%, about 0.01% to about 0.3%, about 0.01% to about 0.2%, or about 0.01% to about 0.1% by weight of the second composition.

In some aspects, the lubricant can be present in amounts of about 0.1% to about 10% by weight of the second composition. In some aspects, the lubricant can be present in amounts of about 0.10% to about 9%, about 0.10% to about 8%, about 0.10% to about 7%, about 0.1% to about 6%, about 0.1% to about 5%, about 0.1% to about 4%, about 0.1% to about 3%, about 0.1% to about 2%, about 0.1% to about 10%, about 0.10% to about 0.9%, about 0.1% to about 0.8%, about 0.1% to about 0.7%, about 0.1% to about 0.6%, about 0.10% to about 0.5%, about 0.10% to about 0.4%, about 0.10% to about 0.3%, about 0.10% to about 0.2% by weight of the second composition.

In some aspects, the lubricant can be present in amounts of about 0.5% to about 10% by weight of the second composition. In some aspects, the lubricant can be present in amounts of about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 10%, about 0.5% to about 0.9%, about 0.5% to about 0.8%, about 0.5% to about 0.7%, or about 0.5% to about 0.6% by weight of the second composition.

In some aspects, the lubricant can be present in amounts of about 1% to about 10% by weight of the second composition. In some aspects, the lubricant can be present in amounts of about 1% to about 9%, about 1% to about 8%, about 1% to about 7%, about 1% to about 6%, about 10% to about 5%, about 10% to about 4%, about 10% to about 3%, about 1% to about 2%, or about 1% to about 2% by weight of the second composition.

In some aspects, the lubricant can be present in amounts of about 5% to about 10%, about 5% to about 9%, about 5% to about 8%, about 5% to about 7%, or about 5% to about 6% by weight of the second composition.

In some aspects, the first composition can comprise about 1.5 mg of the SERM, or an equivalent amount of a pharmaceutically acceptable salt thereof, and the second composition can comprise about 200 mg of testosterone. In some aspects, the first composition can comprise about 2 mg of the SERM, or an equivalent amount of a pharmaceutically acceptable salt thereof, and the second composition can comprise 200 mg of testosterone. In some aspects, the first composition can comprise about 3.125 mg of the SERM, or an equivalent amount of a pharmaceutically acceptable salt thereof, and the second composition can comprise about 200 mg of testosterone. In some aspects, the first composition can comprise about 4 mg of the SERM, or an equivalent amount of a pharmaceutically acceptable salt thereof, and the second composition can comprise about 200 mg of testosterone In some aspects, the first composition can comprise about 6.25 mg of the SERM, or an equivalent amount of a pharmaceutically acceptable salt thereof, and the second composition can comprise about 200 mg of testosterone In some aspects, the first composition can comprise about 12.5 mg of the SERM, or an equivalent amount of a pharmaceutically acceptable salt thereof, and the second composition can comprise about 200 mg of testosterone. In some aspects, the first composition can comprise about 25 mg of the SERM, or an equivalent amount of a pharmaceutically acceptable salt thereof, and the second composition can comprise about 200 mg of testosterone. In some aspects, the first composition can comprise about 50 mg of the SERM, or an equivalent amount of a pharmaceutically acceptable salt thereof, and the second composition can comprise about 200 mg of testosterone.

In some aspects, the first composition can comprise about 1.5 mg of enclomiphene, or an equivalent amount of a pharmaceutically acceptable salt thereof, and the second composition can comprise about 200 mg of testosterone. In some aspects, the first composition can comprise about 2 mg of enclomiphene, or an equivalent amount of a pharmaceutically acceptable salt thereof, and the second composition can comprise 200 mg of testosterone. In some aspects, the first composition can comprise about 3.125 mg of enclomiphene, or an equivalent amount of a pharmaceutically acceptable salt thereof, and the second composition can comprise about 200 mg of testosterone. In some aspects, the first composition can comprise about 4 mg of enclomiphene, or an equivalent amount of a pharmaceutically acceptable salt thereof, and the second composition can comprise about 200 mg of testosterone. In some aspects, the first composition can comprise about 6.25 mg of enclomiphene, or an equivalent amount of a pharmaceutically acceptable salt thereof, and the second composition can comprise about 200 mg of testosterone. In some aspects, the first composition can comprise about 12.5 mg of enclomiphene, or an equivalent amount of a pharmaceutically acceptable salt thereof, and about 200 mg of testosterone. In some aspects, the first composition can comprise about 25 mg of enclomiphene, or an equivalent amount of a pharmaceutically acceptable salt thereof, and the second composition can comprise about 200 mg of testosterone. In some aspects, the first composition can comprise about 50 mg of enclomiphene, or an equivalent amount of a pharmaceutically acceptable salt thereof, and the second composition can comprise about 200 mg of testosterone. In some aspects, the first composition can comprise about 1.5 mg of toremifene, or an equivalent amount of a pharmaceutically acceptable salt thereof, and the second composition can comprise about 200 mg of testosterone. In some aspects, the first composition of the pharmaceutical combination can comprise about 2 mg of toremifene, or an equivalent amount of a pharmaceutically acceptable salt thereof, and the second composition can comprise 200 mg of testosterone. In some aspects, the first composition can comprise about 3.125 mg of toremifene, or an equivalent amount of a pharmaceutically acceptable salt thereof, and the second composition can comprise about 200 mg of testosterone. In some aspects, the first composition can comprise about 4 mg of toremifene, or an equivalent amount of a pharmaceutically acceptable salt thereof, and the second composition can comprise about 200 mg of testosterone. In some aspects, the first composition can comprise about 6.25 mg of toremifene, or an equivalent amount of a pharmaceutically acceptable salt thereof, and the second composition can comprise about 200 mg of testosterone. In some aspects, the first composition can comprise about 12.5 mg of toremifene, or an equivalent amount of a pharmaceutically acceptable salt thereof, and about 200 mg of testosterone. In some aspects, the first composition can comprise about 25 mg of toremifene, or an equivalent amount of a pharmaceutically acceptable salt thereof, and the second composition can comprise about 200 mg of testosterone. In some aspects, the first composition can comprise about 50 mg of toremifene, or an equivalent amount of a pharmaceutically acceptable salt thereof, and the second composition can comprise about 200 mg of testosterone. In some aspects, the first composition can comprise about 60 mg of toremifene, or an equivalent amount of a pharmaceutically acceptable salt thereof, and the second composition can comprise about 200 mg of testosterone. In some aspects, the first composition can comprise about 70 mg of toremifene, or an equivalent amount of a pharmaceutically acceptable salt thereof, and the second composition can comprise about 200 mg of testosterone. In some aspects, the first composition can comprise about 80 mg of toremifene, or an equivalent amount of a pharmaceutically acceptable salt thereof, and the second composition can comprise about 200 mg of testosterone. In some aspects, the first composition can comprise about 90 mg of toremifene, or an equivalent amount of a pharmaceutically acceptable salt thereof, and the second composition can comprise about 200 mg of testosterone. In some aspects, the first composition can comprise about 100 mg of toremifene, or an equivalent amount of a pharmaceutically acceptable salt thereof, and the second composition can comprise about 200 mg of testosterone. In some aspects, the first composition can comprise about 110 mg of toremifene, or an equivalent amount of a pharmaceutically acceptable salt thereof, and the second composition can comprise about 200 mg of testosterone. In some aspects, the first composition can comprise about 120 mg of toremifene, or an equivalent amount of a pharmaceutically acceptable salt thereof, and the second composition can comprise about 200 mg of testosterone.

In some aspects, the first composition can comprise about 1.5 mg of the SERM, or an equivalent amount of a pharmaceutically acceptable salt thereof, and about 5 mg of the neurosteroid and the second composition can comprise about 200 mg of testosterone. In some aspects, the first composition can comprise about 2 mg of the SERM, or an equivalent amount of a pharmaceutically acceptable salt thereof, and about 5 mg of the neurosteroid and the second composition can comprise about 200 mg of testosterone. In some aspects, the first composition can comprise about 3.125 mg of the SERM, or an equivalent amount of a pharmaceutically acceptable salt thereof, and about 2.5 mg of the neurosteroid and the second composition can comprise about 200 mg of testosterone. In some aspects, the first composition can comprise about 3 mg of the SERM, or an equivalent amount of a pharmaceutically acceptable salt thereof, and about 5 mg of the neurosteroid and the second composition can comprise about 200 mg of testosterone. In some aspects, the first composition can comprise about 4 mg of the SERM, or an equivalent amount of a pharmaceutically acceptable salt thereof, and about 5 mg of the neurosteroid and the second composition can comprise about 200 mg of testosterone. In some aspects, the first composition can comprise about 6.25 mg of the SERM, or an equivalent amount of a pharmaceutically acceptable salt thereof, and about 5 mg of the neurosteroid and the second composition can comprise about 200 mg of testosterone. In some aspects, the first composition can comprise about 12.5 mg of the SERM, or an equivalent amount of a pharmaceutically acceptable salt thereof, and about 10 mg of the neurosteroid and the second composition can comprise about 200 mg of testosterone. In some aspects, the first composition can comprise about 25 mg of the SERM, or an equivalent amount of a pharmaceutically acceptable salt thereof, and about 20 mg of the neurosteroid and the second composition can comprise about 200 mg of testosterone. In some aspects, the first composition can comprise or about 50 mg of the SERM, or an equivalent amount of a pharmaceutically acceptable salt thereof, and about 40 mg of the neurosteroid and the second composition can comprise about 200 mg of testosterone.

In some aspects, the first composition can comprise about 1.5 mg of enclomiphene, or an equivalent amount of a pharmaceutically acceptable salt thereof, and about 5 mg of pregnenolone and the second composition can comprise about 200 mg of testosterone. In some aspects, the first composition can comprise about 2 mg of enclomiphene, or an equivalent amount of a pharmaceutically acceptable salt thereof, and about 5 mg of pregnenolone and the second composition can comprise about 200 mg of testosterone. In some aspects, the first composition can comprise about 3.125 mg of enclomiphene, or an equivalent amount of a pharmaceutically acceptable salt thereof, and about 2.5 mg of the neurosteroid and the second composition can comprise about 200 mg of testosterone. In some aspects, the first composition can comprise about 3 mg of enclomiphene, or an equivalent amount of a pharmaceutically acceptable salt thereof, and about 5 mg of the neurosteroid and the second composition can comprise about 200 mg of testosterone. In some aspects, the first composition can comprise about 4 mg of enclomiphene, or an equivalent amount of a pharmaceutically acceptable salt thereof, and about 5 mg of the neurosteroid and the second composition can comprise about 200 mg of testosterone. In some aspects, the first composition can comprise about 6.25 mg of enclomiphene, or an equivalent amount of a pharmaceutically acceptable salt thereof, and about 5 mg of the neurosteroid and the second composition can comprise about 200 mg of testosterone. In some aspects, the first composition can comprise about 12.5 mg of enclomiphene, or an equivalent amount of a pharmaceutically acceptable salt thereof, and about 10 mg of the neurosteroid and the second composition can comprise about 200 mg of testosterone. In some aspects, the first composition can comprise about 25 mg of enclomiphene, or an equivalent amount of a pharmaceutically acceptable salt thereof, and about 20 mg of the neurosteroid and the second composition can comprise about 200 mg of testosterone. In some aspects, the first composition can comprise or about 50 mg of enclomiphene, or an equivalent amount of a pharmaceutically acceptable salt thereof, and about 40 mg of the neurosteroid and the second composition can comprise about 200 mg of testosterone.

In some aspects, the first composition can comprise about 1.5 mg of toremifene, or an equivalent amount of a pharmaceutically acceptable salt thereof, and about 5 mg of pregnenolone and the second composition can comprise about 200 mg of testosterone. In some aspects, the first composition of the pharmaceutical combination can comprise about 2 mg of toremifene, or an equivalent amount of a pharmaceutically acceptable salt thereof, and about 5 mg of pregnenolone and the second composition can comprise about 200 mg of testosterone. In some aspects, the first composition can comprise about 3.125 mg of toremifene, or an equivalent amount of a pharmaceutically acceptable salt thereof, and about 2.5 mg of the neurosteroid and the second composition can comprise about 200 mg of testosterone. In some aspects, the first composition can comprise about 3 mg of toremifene, or an equivalent amount of a pharmaceutically acceptable salt thereof, and about 5 mg of the neurosteroid and the second composition can comprise about 200 mg of testosterone. In some aspects, the first composition can comprise about 4 mg of toremifene, or an equivalent amount of a pharmaceutically acceptable salt thereof, and about 5 mg of the neurosteroid and the second composition can comprise about 200 mg of testosterone. In some aspects, the first composition can comprise about 6.25 mg of toremifene, or an equivalent amount of a pharmaceutically acceptable salt thereof, and about 5 mg of the neurosteroid and the second composition can comprise about 200 mg of testosterone. In some aspects, the first composition can comprise about 12.5 mg of toremifene, or an equivalent amount of a pharmaceutically acceptable salt thereof, and about 10 mg of the neurosteroid and the second composition can comprise about 200 mg of testosterone. In some aspects, the first composition can comprise about 25 mg of toremifene, or an equivalent amount of a pharmaceutically acceptable salt thereof, and about 20 mg of the neurosteroid and the second composition can comprise about 200 mg of testosterone. In some aspects, the first composition can comprise or about 50 mg of toremifene, or an equivalent amount of a pharmaceutically acceptable salt thereof, and about 40 mg of the neurosteroid and the second composition can comprise about 200 mg of testosterone. In some aspects, the first composition can comprise or about 60 mg of toremifene, or an equivalent amount of a pharmaceutically acceptable salt thereof, and about 40 mg of the neurosteroid and the second composition can comprise about 200 mg of testosterone. In some aspects, the first composition can comprise or about 70 mg of toremifene, or an equivalent amount of a pharmaceutically acceptable salt thereof, and about 40 mg of the neurosteroid and the second composition can comprise about 200 mg of testosterone. In some aspects, the first composition can comprise or about 80 mg of toremifene, or an equivalent amount of a pharmaceutically acceptable salt thereof, and about 40 mg of the neurosteroid and the second composition can comprise about 200 mg of testosterone. In some aspects, the first composition can comprise or about 90 mg of toremifene, or an equivalent amount of a pharmaceutically acceptable salt thereof, and about 40 mg of the neurosteroid and the second composition can comprise about 200 mg of testosterone. In some aspects, the first composition can comprise or about 100 mg of toremifene, or an equivalent amount of a pharmaceutically acceptable salt thereof, and about 40 mg of the neurosteroid and the second composition can comprise about 200 mg of testosterone. In some aspects, the first composition can comprise or about 110 mg of toremifene, or an equivalent amount of a pharmaceutically acceptable salt thereof, and about 40 mg of the neurosteroid and the second composition can comprise about 200 mg of testosterone. In some aspects, the first composition can comprise or about 120 mg of toremifene, or an equivalent amount of a pharmaceutically acceptable salt thereof, and about 40 mg of the neurosteroid and the second composition can comprise about 200 mg of testosterone.

In some aspects, the pharmaceutical combination can further comprise a 5α-reductase inhibitor. In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects, the 5α-reductase inhibitor can be dutasteride. In some aspects, the 5α-reductase inhibitor can be finasteride.

In some aspects, the pharmaceutical combination can comprise about 0.1 mg to about 1,000 mg of the 5α-reductase inhibitor. In some aspects, the pharmaceutical combination can comprise about 0.1 mg to about 500 mg, about 0.1 mg to about 100 mg, about 0.1 mg to about 50 mg, about 0.1 mg to about 10 mg of the 5α-reductase inhibitor. In some aspects, the pharmaceutical combination can comprise about 0.1 mg to about 5 mg or about 0.1 mg to about 2.5 mg of the 5α-reductase inhibitor. In some aspects, the pharmaceutical combination can comprise about 0.1 mg to about 2 mg, about 0.1 mg to about 1.5 mg, about 0.1 mg to about 1 mg, about 0.2 mg to about 1 mg, about 0.3 mg to about 1 mg, about 0.4 mg to about 1 mg, or about 0.5 mg to about 1 mg of the 5α-reductase inhibitor.

In some aspects, the pharmaceutical combination can comprise about 0.1 mg to about 1 mg, about 0.1 mg to about 0.9 mg, about 0.2 mg to about 0.8 mg, about 0.3 mg to about 0.7 mg, about 0.4 mg to about 0.6 mg, or about 0.5 mg of the 5α-reductase inhibitor. In some aspects, the pharmaceutical combination can comprise about 0.5 mg to about 1.5 mg, about 0.6 mg to about 1.4 mg, about 0.7 mg to about 1.3 mg, about 0.8 mg to about 1.2 mg, about 0.9 mg to about 1.1 mg, or about 1 mg of the 5α-reductase inhibitor.

In some aspects, the pharmaceutical combination can further comprise about 0.01 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, or about 2.5 mg of the 5α-reductase inhibitor.

In some aspects, the 5α-reductase inhibitor can be dutasteride and the pharmaceutical combination can comprise about 0.1 mg to about 5 mg, about 0.1 mg to about 4 mg, about 0.1 mg to about 3 mg, about 0.1 mg to about 2.5 mg, about 0.1 mg to about 2 mg, about 0.1 mg to about 1.5 mg, about 0.1 mg to about 1 mg, about 0.1 mg to about 0.9 mg, about 0.2 mg to about 0.8 mg, about 0.3 mg to about 0.7 mg, about 0.4 mg to about 0.6 mg, or about 0.5 mg of dutasteride. In some aspects, the 5α-reductase inhibitor can be finasteride and the pharmaceutical combination can comprise about 0.5 mg to about 5 mg, about 0.5 mg to about 4 mg, about 0.5 mg to about 3 mg, about 0.5 mg to about 2.5 mg, about 0.5 mg to about 2 mg, about, about 0.5 mg to about 1.5 mg, about 0.6 mg to about 1.4 mg, about 0.7 mg to about 1.3 mg, about 0.8 mg to about 1.2 mg, about 0.9 mg to about 1.1 mg, or about 1 mg of finasteride.

In some aspects, the pharmaceutical combination can further comprise an aromatase inhibitor. In some aspects, the aromatase inhibitor can be selected from the group consisting of atamestane, exemestane, and formestane, and non-steroids, such as aminoglutethimide, roglethimide, pyridoglutethimide, trilostane, testolactone, vorozole, fadrozole, anastrozole, letrozole, and combinations thereof. In some aspects, the aromatase inhibitor can be anastrozole. In some aspects, the aromatase inhibitor can be exemestane.

In some aspects, the pharmaceutical combination can comprise about 0.1 mg to about 50 mg of the aromatase inhibitor. In some aspects, the pharmaceutical combination can comprise about 0.1 mg to about 40 mg, about 0.1 mg to about 30 mg, about 0.1 mg to about 25 mg, about 0.1 mg to about 20 mg, about 0.1 mg to about 15 mg, about 0.1 mg to about 12.5 mg, about 0.1 mg to about 10 mg, about 0.1 mg to about 9 mg, about 0.1 mg to about 2.5 mg, about 0.1 mg to about 1 mg, about 0.1 mg to about 0.9 mg, about 0.1 mg to about 0.8 mg, about 0.1 mg to about 0.7 mg, about 0.1 mg to about 0.6 mg, or about 0.1 mg to about 0.5 mg of the aromatase inhibitor.

In some aspects, the pharmaceutical combination can comprise about 0.1 mg to about 0.5 mg, 0.1 mg to about 0.4 mg, about 0.1 to about 0.3 mg, about 0.2 mg to about 0.4 mg, about 0.2 mg to about 0.3 mg, or about 0.25 mg of the aromatase inhibitor. In some aspects, the pharmaceutical combination can comprise about 0.2 mg to about 0.8 mg, 0.2 mg to about 0.6 mg, about 0.2 mg to about 0.5 mg, about 0.3 mg to about 0.7 mg, or about 0.4 mg to about 0.6 mg, or about 0.5 mg of the aromatase inhibitor. In some aspects, the pharmaceutical combination can comprise about 0.25 mg to about 0.5 mg of the aromatase inhibitor.

In some aspects, the pharmaceutical combination can comprise about 5 mg to about 30 mg, about 10 mg to about 30 mg, about 10 mg to about 25 mg, about 10 mg to about 20 mg, about 10 mg to about 15 mg, about 15 mg to about 30 mg, about 20 mg to about 30 mg of the aromatase inhibitor. In some aspects, the pharmaceutical combination can comprise about 10 mg to about 15 mg, about 11 mg to about 14 mg, about 12 to about 13 mg, or about 12.5 mg of the aromatase inhibitor. In some aspects, the pharmaceutical combination can comprise about 20 mg to about 30 mg, about 21 mg to about 29 mg, about 22 mg to about 28 mg, about 23 mg to about 27 mg, about 24 mg to about 26 mg, or about 25 mg of the aromatase inhibitor.

In some aspects, the pharmaceutical combination can comprise about 0.1 mg, about 0.25 mg, about 0.5 mg, about 0.6 mg, about 0.7 mg, about 0.8 mg, about 0.9 mg, about 1 mg, about 1.5 mg, about 2 mg, about 2.5 mg, about 5 mg, about 7.5 mg, about 10 mg, about 12.5 mg, about 15 mg, about 20 mg, about 25 mg, about 30 mg of the aromatase inhibitor.

In some aspects, the pharmaceutical combination can comprise about 0.1 mg to about 1 mg, about 0.1 mg to about 0.5 mg, 0.1 mg to about 0.4 mg, about 0.1 to about 0.3 mg, about 0.2 mg to about 0.4 mg, about 0.2 mg to about 0.3 mg, or about 0.25 mg of anastrozole. In some aspects, the pharmaceutical combination can comprise about 0.2 mg to about 0.8 mg, 0.2 mg to about 0.6 mg, about 0.2 mg to about 0.5 mg, about 0.3 mg to about 0.7 mg, or about 0.4 mg to about 0.6 mg, or about 0.5 mg of anastrozole. In some aspects, the pharmaceutical combination can comprise about 0.25 mg to about 0.5 mg of anastrozole.

In some aspects, the pharmaceutical combination can comprise about 5 mg to about 30 mg, about 10 mg to about 30 mg, about 10 mg to about 25 mg, about 10 mg to about 20 mg, about 10 mg to about 15 mg, about 15 mg to about 30 mg, about 20 mg to about 30 mg of exemestane. In some aspects, the pharmaceutical combination can comprise about 10 mg to about 15 mg, about 11 mg to about 14 mg, about 12 to about 13 mg, or about 12.5 mg of exemestane. In some aspects, the pharmaceutical combination can comprise about 20 mg to about 30 mg, about 21 mg to about 29 mg, about 22 mg to about 28 mg, about 23 mg to about 27 mg, about 24 mg to about 26 mg, or about 25 mg of exemestane.

In some aspects, the pharmaceutical combination can further comprise ketoconazole.

In some aspects, the pharmaceutical combination can comprise a first composition in a form suitable for sublingual administration comprising: about 1 mg to about 50 mg of enclomiphene citrate, cellulose, a non-nutritive sweetener, a flavoring agent, and magnesium stearate; and at least one second composition in a form suitable for oral administration and lymphatic absorption comprising: about 200 mg of native testosterone, safflower oil, cellulose, and magnesium stearate.

The present disclosure is also directed to a pharmaceutical combination comprising a first composition comprising a therapeutically effective amount of a selective estrogen receptor modulator (SERM) in a form suitable for oral administration, and a second composition comprising testosterone in a form suitable for topical or transdermal administration. In some aspects, the first composition and the second composition can be administered simultaneously, concurrently, or sequentially.

In some aspects, the first composition comprising the therapeutically effective amount of the SERM can be in a form suitable for oral administration. In some aspects, the first composition can be an oral tablet or capsule. In some aspects, the first composition can be in a form suitable for sublingual administration. In some aspects, the first composition can be a sublingual tablet.

In some aspects, the second composition can be in a form suitable for topical administration. In some aspects, the pharmaceutical composition can be suitable for topical administration, including a lotion, emulsion, cream, gel, ointment, foam, liquid, paste or other topically administrable form. In some aspects, the pharmaceutical composition can be suitable for transdermal administration, including a transdermal patch, transdermal lotion, transdermal cream, transdermal gel, transdermal ointment, transdermal foam, transdermal liquid, transdermal paste or other transdermally administrable form. In some aspects, the second composition can be suitable for transdermal administration, a transdermal patch, transdermal lotion, transdermal cream, transdermal gel, transdermal ointment, transdermal foam, transdermal liquid, transdermal paste or other transdermally administrable form.

In some aspects, the first composition can be the pharmaceutical composition, described above, comprising therapeutically effective amounts of the SERM and the steroid hormone. In some aspects, the steroid hormone is selected from the group consisting of a neurosteroid, DHEA, estrogen, DHT, and combinations thereof. In some aspects, the steroid hormone is a neurosteroid.

In other aspects, the combination can comprise a first composition comprising a therapeutically effective amount of a selective estrogen receptor modulator (SERM) in a form suitable for oral administration, a second composition comprising testosterone in a form suitable for topical or transdermal administration, and a third composition comprising a therapeutically effective amount of the neurosteroid. In some aspects of this combination, the third composition comprising the therapeutically effective amount of the neurosteroid can be in a form suitable for sublingual administration. In some aspects, the third composition comprising the therapeutically effective amount of the neurosteroid in a form suitable for sublingual administration can be a tablet. In some aspects, the third composition comprising the therapeutically effective amount of the neurosteroid can be in a form suitable for topical administration. In some aspects, the third composition comprising the therapeutically effective amount of the neurosteroid in a form suitable for topical administration can be a topical gel. In some aspects, the third composition comprising the therapeutically effective amount of the neurosteroid can be in a form suitable for transdermal administration. In some aspects, the third composition comprising the therapeutically effective amount of the neurosteroid in a form suitable for transdermal administration can be a transdermal patch. In some aspects, the third composition can comprise the neurosteroid in the amounts described above related to the pharmaceutical composition. In some aspects, the neurosteroid can be pregnenolone. In some aspects, the third composition can comprise pregnenolone in the amounts described above related to the pharmaceutical composition. In certain aspects of the combination comprising the three compositions, the first, second, and third compositions, can be administered simultaneously, concurrently, or sequentially.

In some aspects, the first composition can comprise the SERM, or an equivalent amount of a pharmaceutically acceptable salt thereof, in an amount or range previously disclosed herein. In some aspects, the first composition can comprise enclomiphene, or an equivalent amount of a pharmaceutically acceptable salt thereof, in an amount or range previously disclosed herein. In some aspects, the first composition can comprise clomiphene, or an equivalent amount of a pharmaceutically acceptable salt thereof, in an amount or range previously disclosed herein. In some aspects, the first composition can comprise toremifene, or an equivalent amount of a pharmaceutically acceptable salt thereof, in an amount or range as previously disclosed herein.

In some aspects, the first composition can further comprise a neurosteroid in an amount or range as previously disclosed herein. In some aspects, the first composition can further comprise pregnenolone in an amount or range as previously disclosed herein.

In some aspects, the first composition can further comprise about 5 mg of the SERM, or an equivalent of a pharmaceutically acceptable salt thereof, about 2.5 mg of the neurosteroid. In some aspects, the first composition can further comprise about 6.25 mg of the SERM, or an equivalent of a pharmaceutically acceptable salt thereof, about 2.5 mg of the neurosteroid; about 10 mg of the SERM, or an equivalent of a pharmaceutically acceptable salt thereof, about 5 mg of the neurosteroid; about 12.5 mg of the SERM, or an equivalent of a pharmaceutically acceptable salt thereof, and about 5 mg of the neurosteroid; about 12.5 mg of the SERM, or an equivalent amount of a pharmaceutically acceptable salt thereof, and about 10 mg of the neurosteroid; about 25 mg of the SERM, or an equivalent amount of a pharmaceutically acceptable salt thereof, and about 20 mg of the neurosteroid; or about 50 mg of the SERM, or an equivalent amount of a pharmaceutically acceptable salt thereof, and about 40 mg of the neurosteroid.

In some aspects, the first composition can further comprise about 5 mg of enclomiphene, or an equivalent amount of a pharmaceutically acceptable salt thereof, and about 2.5 mg of pregnenolone. In some aspects, the first composition can further comprise about 6.25 mg of enclomiphene, or an equivalent of a pharmaceutically acceptable salt thereof, about 2.5 mg of pregnenolone; about 10 mg of enclomiphene, or an equivalent of a pharmaceutically acceptable salt thereof, about 5 mg of the pregnenolone; about 12.5 mg of enclomiphene, or an equivalent amount of a pharmaceutically acceptable salt thereof, and about 5 mg of pregnenolone; about 12.5 mg of enclomiphene, or an equivalent amount of a pharmaceutically acceptable salt thereof, and about 10 mg of pregnenolone; about 25 mg of enclomiphene, or an equivalent amount of a pharmaceutically acceptable salt thereof, and about 20 mg of pregnenolone; or about 50 mg of enclomiphene, or an equivalent amount of a pharmaceutically acceptable salt thereof, and about 40 mg of pregnenolone.

In some aspects, the first composition can also include at least one pharmaceutically acceptable excipient in an amount or range as previously disclosed herein.

In some aspects, the second composition of the pharmaceutical combination can comprise testosterone in an amount or range as previously disclosed herein.

In some aspects, the second composition can also include at least one pharmaceutically acceptable excipient in an amount or range as previously disclosed herein.

It was surprisingly found, when topical or transdermal testosterone is administered to a subject, higher doses of a SERM is needed to counteract the topical or transdermal testosterone's stronger suppressive effect on the hypothalamic-pituitary-gonadal axis compared to when oral testosterone is administered to a subject. Topical or transdermal testosterone exhibits a stronger suppressive effective because it leads to a prolonged duration of elevated testosterone levels compared to oral testosterone. Without wishing to be bound to any particular theory, it is believed that topical or transdermal testosterone offers several advantages over oral testosterone including greater potency, longer duration of action, no requirement for dietary fat for absorption, and faster absorption.

In some aspects, the first composition can comprise about 5 mg of the SERM, or an equivalent amount of a pharmaceutically acceptable salt thereof, and the second composition can comprise about 50 mg of testosterone. In some aspects, the first composition can comprise about 5 mg of the SERM, or an equivalent amount of a pharmaceutically acceptable salt thereof, and the second composition can comprise about 100 mg of testosterone. In some aspects, the first composition can comprise about 5 mg of the SERM, or an equivalent amount of a pharmaceutically acceptable salt thereof, and the second composition can comprise about 200 mg of testosterone. In some aspects, the first composition can comprise about 6.25 mg of the SERM, or an equivalent amount of a pharmaceutically acceptable salt thereof, and the second composition can comprise about 50 mg of testosterone. In some aspects, the first composition can comprise about 6.25 mg of the SERM, or an equivalent amount of a pharmaceutically acceptable salt thereof, and the second composition can comprise about 100 mg of testosterone. In some aspects, the first composition can comprise about 6.25 mg of the SERM, or an equivalent amount of a pharmaceutically acceptable salt thereof, and the second composition can comprise about 200 mg of testosterone. In some aspects, the first composition can comprise about 10 mg of the SERM, or an equivalent amount of a pharmaceutically acceptable salt thereof, and the second composition can comprise about 50 mg of testosterone. In some aspects, the first composition can comprise about 10 mg of the SERM, or an equivalent amount of a pharmaceutically acceptable salt thereof, and the second composition can comprise about 100 mg of testosterone. In some aspects, the first composition can comprise about 10 mg of the SERM, or an equivalent amount of a pharmaceutically acceptable salt thereof, and the second composition can comprise about 200 mg of testosterone. In some aspects, the first composition can comprise about 12.5 mg of the SERM, or an equivalent amount of a pharmaceutically acceptable salt thereof, and the second composition can comprise about 50 mg of testosterone. In some aspects, the first composition can comprise about 12.5 mg of the SERM, or an equivalent amount of a pharmaceutically acceptable salt thereof, and about 100 mg of testosterone. In some aspects, the first composition can comprise about 12.5 mg of the SERM, or an equivalent amount of a pharmaceutically acceptable salt thereof, and about 200 mg of testosterone. In some aspects, the first composition can comprise about 20 mg of the SERM, or an equivalent amount of a pharmaceutically acceptable salt thereof, and the second composition can comprise about 50 mg of testosterone. In some aspects, the first composition can comprise about 20 mg of the SERM, or an equivalent amount of a pharmaceutically acceptable salt thereof, and about 100 mg of testosterone. In some aspects, the first composition can comprise about 20 mg of the SERM, or an equivalent amount of a pharmaceutically acceptable salt thereof, and about 200 mg of testosterone. In some aspects, the first composition can comprise about 25 mg of the SERM, or an equivalent amount of a pharmaceutically acceptable salt thereof, and the second composition can comprise about 50 mg of testosterone. In some aspects, the first composition can comprise about 25 mg of the SERM, or an equivalent amount of a pharmaceutically acceptable salt thereof, and the second composition can comprise about 100 mg of testosterone. In some aspects, the first composition can comprise about 25 mg of the SERM, or an equivalent amount of a pharmaceutically acceptable salt thereof, and about 200 mg of testosterone. In some aspects, the first composition can comprise about 40 mg of the SERM, or an equivalent amount of a pharmaceutically acceptable salt thereof, and the second composition can comprise about 50 mg of testosterone. In some aspects, the first composition can comprise about 40 mg of the SERM, or an equivalent amount of a pharmaceutically acceptable salt thereof, and about 100 mg of testosterone. In some aspects, the first composition can comprise about 40 mg of the SERM, or an equivalent amount of a pharmaceutically acceptable salt thereof, and about 200 mg of testosterone. In some aspects, the first composition can comprise about 50 mg of the SERM, or an equivalent amount of a pharmaceutically acceptable salt thereof, and the second composition can comprise about 50 mg of testosterone. In some aspects, the first composition can comprise about 50 mg of the SERM, or an equivalent amount of a pharmaceutically acceptable salt thereof, and the second composition can comprise about 100 mg of testosterone. In some aspects, the first composition can comprise about 50 mg of the SERM, or an equivalent amount of a pharmaceutically acceptable salt thereof, and the second composition can comprise about 200 mg of testosterone. In some aspects, the first composition can comprise about 60 mg of the SERM, or an equivalent amount of a pharmaceutically acceptable salt thereof, and the second composition can comprise about 50 mg of testosterone. In some aspects, the first composition can comprise about 60 mg of the SERM, or an equivalent amount of a pharmaceutically acceptable salt thereof, and the second composition can comprise about 100 mg of testosterone. In some aspects, the first composition can comprise about 60 mg of the SERM, or an equivalent amount of a pharmaceutically acceptable salt thereof, and the second composition can comprise about 200 mg of testosterone. In some aspects, the first composition can comprise about 80 mg of the SERM, or an equivalent amount of a pharmaceutically acceptable salt thereof, and the second composition can comprise about 50 mg of testosterone. In some aspects, the first composition can comprise about 80 mg of the SERM, or an equivalent amount of a pharmaceutically acceptable salt thereof, and the second composition can comprise about 100 mg of testosterone. In some aspects, the first composition can comprise about 80 mg of the SERM, or an equivalent amount of a pharmaceutically acceptable salt thereof, and the second composition can comprise about 200 mg of testosterone. In some aspects, the first composition can comprise about 100 mg of the SERM, or an equivalent amount of a pharmaceutically acceptable salt thereof, and the second composition can comprise about 50 mg of testosterone. In some aspects, the first composition can comprise about 100 mg of the SERM, or an equivalent amount of a pharmaceutically acceptable salt thereof, and the second composition can comprise about 100 mg of testosterone. In some aspects, the first composition can comprise about 100 mg of the SERM, or an equivalent amount of a pharmaceutically acceptable salt thereof, and the second composition can comprise about 200 mg of testosterone. In some aspects, the first composition can comprise about 120 mg of the SERM, or an equivalent amount of a pharmaceutically acceptable salt thereof, and the second composition can comprise about 50 mg of testosterone. In some aspects, the first composition can comprise about 120 mg of the SERM, or an equivalent amount of a pharmaceutically acceptable salt thereof, and the second composition can comprise about 100 mg of testosterone. In some aspects, the first composition can comprise about 120 mg of the SERM, or an equivalent amount of a pharmaceutically acceptable salt thereof, and the second composition can comprise about 200 mg of testosterone. In some aspects, the first composition can comprise about 150 mg of the SERM, or an equivalent amount of a pharmaceutically acceptable salt thereof, and the second composition can comprise about 50 mg of testosterone. In some aspects, the first composition can comprise about 150 mg of the SERM, or an equivalent amount of a pharmaceutically acceptable salt thereof, and the second composition can comprise about 100 mg of testosterone. In some aspects, the first composition can comprise about 150 mg of the SERM, or an equivalent amount of a pharmaceutically acceptable salt thereof, and the second composition can comprise about 200 mg of testosterone.

In some aspects, the first composition can comprise about 5 mg of enclomiphene, or an equivalent amount of a pharmaceutically acceptable salt thereof, and the second composition can comprise about 50 mg of testosterone. In some aspects, the first composition can comprise about 5 mg of enclomiphene, or an equivalent amount of a pharmaceutically acceptable salt thereof, and the second composition can comprise about 100 mg of testosterone. In some aspects, the first composition can comprise about 5 mg of enclomiphene, or an equivalent amount of a pharmaceutically acceptable salt thereof, and the second composition can comprise about 200 mg of testosterone. In some aspects, the first composition can comprise about 6.25 mg of enclomiphene, or an equivalent amount of a pharmaceutically acceptable salt thereof, and the second composition can comprise about 50 mg of testosterone. In some aspects, the first composition can comprise about 6.25 mg of enclomiphene, or an equivalent amount of a pharmaceutically acceptable salt thereof, and the second composition can comprise about 100 mg of testosterone. In some aspects, the first composition can comprise about 6.25 mg of enclomiphene, or an equivalent amount of a pharmaceutically acceptable salt thereof, and the second composition can comprise about 200 mg of testosterone. In some aspects, the first composition can comprise about 10 mg of enclomiphene, or an equivalent amount of a pharmaceutically acceptable salt thereof, and the second composition can comprise about 50 mg of testosterone. In some aspects, the first composition can comprise about 10 mg of enclomiphene, or an equivalent amount of a pharmaceutically acceptable salt thereof, and the second composition can comprise about 100 mg of testosterone. In some aspects, the first composition can comprise about 10 mg of enclomiphene, or an equivalent amount of a pharmaceutically acceptable salt thereof, and the second composition can comprise 200 mg of testosterone. In some aspects, the first composition can comprise about 12.5 mg of enclomiphene, or an equivalent amount of a pharmaceutically acceptable salt thereof, and the second composition can comprise about 50 mg of testosterone. In some aspects, the first composition can comprise about 12.5 mg of enclomiphene, or an equivalent amount of a pharmaceutically acceptable salt thereof, and about 100 mg of testosterone. In some aspects, the first composition can comprise about 12.5 mg of enclomiphene, or an equivalent amount of a pharmaceutically acceptable salt thereof, and about 200 mg of testosterone. In some aspects, the first composition can comprise about 25 mg of enclomiphene, or an equivalent amount of a pharmaceutically acceptable salt thereof, and the second composition can comprise about 50 mg of testosterone. In some aspects, the first composition can comprise about 25 mg of enclomiphene, or an equivalent amount of a pharmaceutically acceptable salt thereof, and the second composition can comprise about 100 mg of testosterone. In some aspects, the first composition can comprise about 25 mg of enclomiphene, or an equivalent amount of a pharmaceutically acceptable salt thereof, and about 200 mg of testosterone. In some aspects, the first composition can comprise about 50 mg of enclomiphene, or an equivalent amount of a pharmaceutically acceptable salt thereof, and the second composition can comprise about 50 mg of testosterone. In some aspects, the first composition can comprise about 50 mg of enclomiphene, or an equivalent amount of a pharmaceutically acceptable salt thereof, and the second composition can comprise about 100 mg of testosterone. In some aspects, the first composition can comprise about 50 mg of enclomiphene, or an equivalent amount of a pharmaceutically acceptable salt thereof, and the second composition can comprise about 200 mg of testosterone. In some aspects, the first composition can comprise about 100 mg of enclomiphene, or an equivalent amount of a pharmaceutically acceptable salt thereof, and the second composition can comprise about 50 mg of testosterone. In some aspects, the first composition can comprise about 100 mg of enclomiphene, or an equivalent amount of a pharmaceutically acceptable salt thereof, and the second composition can comprise about 100 mg of testosterone. In some aspects, the first composition can comprise about 100 mg of enclomiphene, or an equivalent amount of a pharmaceutically acceptable salt thereof, and the second composition can comprise about 200 mg of testosterone. In some aspects, the first composition can comprise about 150 mg of enclomiphene, or an equivalent amount of a pharmaceutically acceptable salt thereof, and the second composition can comprise about 50 mg of testosterone. In some aspects, the first composition can comprise about 150 mg of enclomiphene, or an equivalent amount of a pharmaceutically acceptable salt thereof, and the second composition can comprise about 100 mg of testosterone. In some aspects, the first composition can comprise about 150 mg of enclomiphene, or an equivalent amount of a pharmaceutically acceptable salt thereof, and the second composition can comprise about 200 mg of testosterone.

In some aspects, the first composition can comprise about 5 mg of clomiphene, or an equivalent amount of a pharmaceutically acceptable salt thereof, and the second composition can comprise about 50 mg of testosterone. In some aspects, the first composition can comprise about 5 mg of clomiphene, or an equivalent amount of a pharmaceutically acceptable salt thereof, and the second composition can comprise about 100 mg of testosterone. In some aspects, the first composition can comprise about 5 mg of clomiphene, or an equivalent amount of a pharmaceutically acceptable salt thereof, and the second composition can comprise about 200 mg of testosterone. In some aspects, the first composition can comprise about 6.25 mg of clomiphene, or an equivalent amount of a pharmaceutically acceptable salt thereof, and the second composition can comprise about 50 mg of testosterone. In some aspects, the first composition can comprise about 6.25 mg of clomiphene, or an equivalent amount of a pharmaceutically acceptable salt thereof, and the second composition can comprise about 100 mg of testosterone. In some aspects, the first composition can comprise about 6.25 mg of clomiphene, or an equivalent amount of a pharmaceutically acceptable salt thereof, and the second composition can comprise about 200 mg of testosterone. In some aspects, the first composition can comprise about 10 mg of clomiphene, or an equivalent amount of a pharmaceutically acceptable salt thereof, and the second composition can comprise about 50 mg of testosterone. In some aspects, the first composition can comprise about 10 mg of clomiphene, or an equivalent amount of a pharmaceutically acceptable salt thereof, and the second composition can comprise about 100 mg of testosterone. In some aspects, the first composition can comprise about 10 mg of clomiphene, or an equivalent amount of a pharmaceutically acceptable salt thereof, and the second composition can comprise 200 mg of testosterone. In some aspects, the first composition can comprise about 12.5 mg of clomiphene, or an equivalent amount of a pharmaceutically acceptable salt thereof, and the second composition can comprise about 50 mg of testosterone. In some aspects, the first composition can comprise about 12.5 mg of clomiphene, or an equivalent amount of a pharmaceutically acceptable salt thereof, and about 100 mg of testosterone. In some aspects, the first composition can comprise about 12.5 mg of clomiphene, or an equivalent amount of a pharmaceutically acceptable salt thereof, and about 200 mg of testosterone. In some aspects, the first composition can comprise about 25 mg of clomiphene, or an equivalent amount of a pharmaceutically acceptable salt thereof, and the second composition can comprise about 50 mg of testosterone. In some aspects, the first composition can comprise about 25 mg of clomiphene, or an equivalent amount of a pharmaceutically acceptable salt thereof, and the second composition can comprise about 100 mg of testosterone. In some aspects, the first composition can comprise about 25 mg of clomiphene, or an equivalent amount of a pharmaceutically acceptable salt thereof, and the second composition can comprise about 200 mg of testosterone. In some aspects, the first composition can comprise about 50 mg of clomiphene, or an equivalent amount of a pharmaceutically acceptable salt thereof, and the second composition can comprise about 50 mg of testosterone. In some aspects, the first composition can comprise about 50 mg of clomiphene, or an equivalent amount of a pharmaceutically acceptable salt thereof, and the second composition can comprise about 100 mg of testosterone. In some aspects, the first composition can comprise about 50 mg of clomiphene, or an equivalent amount of a pharmaceutically acceptable salt thereof, and the second composition can comprise about 200 mg of testosterone. In some aspects, the first composition can comprise about 100 mg of clomiphene, or an equivalent amount of a pharmaceutically acceptable salt thereof, and the second composition can comprise about 50 mg of testosterone. In some aspects, the first composition can comprise about 100 mg of clomiphene, or an equivalent amount of a pharmaceutically acceptable salt thereof, and the second composition can comprise about 100 mg of testosterone. In some aspects, the first composition can comprise about 100 mg of clomiphene, or an equivalent amount of a pharmaceutically acceptable salt thereof, and the second composition can comprise about 200 mg of testosterone. In some aspects, the first composition can comprise about 150 mg of clomiphene, or an equivalent amount of a pharmaceutically acceptable salt thereof, and the second composition can comprise about 50 mg of testosterone. In some aspects, the first composition can comprise about 150 mg of clomiphene, or an equivalent amount of a pharmaceutically acceptable salt thereof, and the second composition can comprise about 100 mg of testosterone. In some aspects, the first composition can comprise about 150 mg of clomiphene, or an equivalent amount of a pharmaceutically acceptable salt thereof, and the second composition can comprise about 200 mg of testosterone.

In some aspects, the first composition can comprise about 5 mg of toremifene, or an equivalent amount of a pharmaceutically acceptable salt thereof, and the second composition can comprise about 50 mg of testosterone. In some aspects, the first composition can comprise about 5 mg of toremifene, or an equivalent amount of a pharmaceutically acceptable salt thereof, and the second composition can comprise about 100 mg of testosterone. In some aspects, the first composition can comprise about 5 mg of toremifene, or an equivalent amount of a pharmaceutically acceptable salt thereof, and the second composition can comprise about 200 mg of testosterone. In some aspects, the first composition can comprise about 10 mg of toremifene, or an equivalent amount of a pharmaceutically acceptable salt thereof, and the second composition can comprise about 50 mg of testosterone. In some aspects, the first composition can comprise about 10 mg of toremifene, or an equivalent amount of a pharmaceutically acceptable salt thereof, and the second composition can comprise about 100 mg of testosterone. In some aspects, the first composition can comprise about 10 mg of toremifene, or an equivalent amount of a pharmaceutically acceptable salt thereof, and the second composition can comprise about 200 mg of testosterone. In some aspects, the first composition can comprise about 20 mg of toremifene, or an equivalent amount of a pharmaceutically acceptable salt thereof, and the second composition can comprise about 50 mg of testosterone. In some aspects, the first composition can comprise about 20 mg of toremifene, or an equivalent amount of a pharmaceutically acceptable salt thereof, and about 100 mg of testosterone. In some aspects, the first composition can comprise about 20 mg of toremifene, or an equivalent amount of a pharmaceutically acceptable salt thereof, and about 200 mg of testosterone. In some aspects, the first composition can comprise about 40 mg of toremifene, or an equivalent amount of a pharmaceutically acceptable salt thereof, and the second composition can comprise about 50 mg of testosterone. In some aspects, the first composition can comprise about 40 mg of toremifene, or an equivalent amount of a pharmaceutically acceptable salt thereof, and about 100 mg of testosterone. In some aspects, the first composition can comprise about 40 mg of toremifene, or an equivalent amount of a pharmaceutically acceptable salt thereof, and about 200 mg of testosterone. In some aspects, the first composition can comprise about 60 mg of toremifene, or an equivalent amount of a pharmaceutically acceptable salt thereof, and the second composition can comprise about 50 mg of testosterone. In some aspects, the first composition can comprise about 60 mg of toremifene, or an equivalent amount of a pharmaceutically acceptable salt thereof, and the second composition can comprise about 100 mg of testosterone. In some aspects, the first composition can comprise about 60 mg of toremifene, or an equivalent amount of a pharmaceutically acceptable salt thereof, and the second composition can comprise about 200 mg of testosterone. In some aspects, the first composition can comprise about 80 mg of toremifene, or an equivalent amount of a pharmaceutically acceptable salt thereof, and the second composition can comprise about 50 mg of testosterone. In some aspects, the first composition can comprise about 80 mg of toremifene, or an equivalent amount of a pharmaceutically acceptable salt thereof, and the second composition can comprise about 100 mg of testosterone. In some aspects, the first composition can comprise about 80 mg of toremifene, or an equivalent amount of a pharmaceutically acceptable salt thereof, and the second composition can comprise about 200 mg of testosterone. In some aspects, the first composition can comprise about 120 mg of toremifene, or an equivalent amount of a pharmaceutically acceptable salt thereof, and the second composition can comprise about 50 mg of testosterone. In some aspects, the first composition can comprise about 120 mg of toremifene, or an equivalent amount of a pharmaceutically acceptable salt thereof, and the second composition can comprise about 100 mg of testosterone. In some aspects, the first composition can comprise about 120 mg of toremifene, or an equivalent amount of a pharmaceutically acceptable salt thereof, and the second composition can comprise about 200 mg of testosterone.

In some aspects, the first composition can comprise about 5 mg of the SERM, or an equivalent amount of a pharmaceutically acceptable salt thereof, and about 2.5 mg of the neurosteroid and the second composition can comprise about 50 mg of testosterone. In some aspects, the first composition can comprise about 5 mg of the SERM, or an equivalent amount of a pharmaceutically acceptable salt thereof, and about 2.5 mg of the neurosteroid and the second composition can comprise about 100 mg of testosterone. In some aspects, the first composition can comprise about 5 mg of the SERM, or an equivalent amount of a pharmaceutically acceptable salt thereof, and about 2.5 mg of the neurosteroid and the second composition can comprise about 200 mg of testosterone. In some aspects, the first composition can comprise about 10 mg of the SERM, or an equivalent amount of a pharmaceutically acceptable salt thereof, and about 2.5 mg of the neurosteroid and the second composition can comprise about 50 mg of testosterone. In some aspects, the first composition can comprise about 10 mg of the SERM, or an equivalent amount of a pharmaceutically acceptable salt thereof, and about 2.5 mg of the neurosteroid and the second composition can comprise about 100 mg of testosterone. In some aspects, the first composition can comprise about 10 mg of the SERM, or an equivalent amount of a pharmaceutically acceptable salt thereof, and about 2.5 mg of the neurosteroid and the second composition can comprise about 200 mg of testosterone. In some aspects, the first composition can comprise about 12.5 mg of the SERM, or an equivalent amount of a pharmaceutically acceptable salt thereof, and about 5 mg of the neurosteroid and the second composition can comprise about 50 mg of testosterone. In some aspects, the first composition can comprise about 12.5 mg of the SERM, or an equivalent amount of a pharmaceutically acceptable salt thereof, and about 5 mg of the neurosteroid and the second composition can comprise about 100 mg of testosterone. In some aspects, the first composition can comprise about 12.5 mg of the SERM, or an equivalent amount of a pharmaceutically acceptable salt thereof, and about 5 mg of the neurosteroid and the second composition can comprise about 200 mg of testosterone. In some aspects, the first composition can comprise about 20 mg of the SERM, or an equivalent amount of a pharmaceutically acceptable salt thereof, and about 10 mg of the neurosteroid and the second composition can comprise about 50 mg of testosterone. In some aspects, the first composition can comprise about 20 mg of the SERM, or an equivalent amount of a pharmaceutically acceptable salt thereof, and about 10 mg of the neurosteroid and the second composition can comprise about 100 mg of testosterone. In some aspects, the first composition can comprise about 20 mg of the SERM, or an equivalent amount of a pharmaceutically acceptable salt thereof, and about 10 mg of the neurosteroid and the second composition can comprise about 200 mg of testosterone. In some aspects, the first composition can comprise about 25 mg of the SERM, or an equivalent amount of a pharmaceutically acceptable salt thereof, and about 20 mg of the neurosteroid and the second composition can comprise about 50 mg of testosterone. In some aspects, the first composition can comprise about 25 mg of the SERM, or an equivalent amount of a pharmaceutically acceptable salt thereof, and about 20 mg of the neurosteroid and the second composition can comprise about 100 mg of testosterone. In some aspects, the first composition can comprise about 25 mg of the SERM, or an equivalent amount of a pharmaceutically acceptable salt thereof, and about 20 mg of the neurosteroid and the second composition can comprise about 200 mg of testosterone. In some aspects, the first composition can comprise about 40 mg of the SERM, or an equivalent amount of a pharmaceutically acceptable salt thereof, and about 20 mg of the neurosteroid and the second composition can comprise about 50 mg of testosterone. In some aspects, the first composition can comprise about 40 mg of the SERM, or an equivalent amount of a pharmaceutically acceptable salt thereof, and about 20 mg of the neurosteroid and a second composition can comprise about 100 mg of testosterone. In some aspects, the first composition can comprise about 40 mg of the SERM, or an equivalent amount of a pharmaceutically acceptable salt thereof, and about 20 mg of the neurosteroid and a second composition can comprise about 200 mg of testosterone. In some aspects, the first composition can comprise about 50 mg of the SERM, or an equivalent amount of a pharmaceutically acceptable salt thereof, and about 20 mg of the neurosteroid and the second composition can comprise about 50 mg of testosterone. In some aspects, the first composition can comprise about 50 mg of the SERM, or an equivalent amount of a pharmaceutically acceptable salt thereof, and about 40 mg of the neurosteroid and a second composition can comprise about 100 mg of testosterone. In some aspects, the first composition can comprise about 50 mg of the SERM, or an equivalent amount of a pharmaceutically acceptable salt thereof, and about 40 mg of the neurosteroid and a second composition can comprise about 200 mg of testosterone. In some aspects, the first composition can comprise about 60 mg of the SERM, or an equivalent amount of a pharmaceutically acceptable salt thereof, and about 40 mg of the neurosteroid and the second composition can comprise about 50 mg of testosterone. In some aspects, the first composition can comprise about 60 mg of the SERM, or an equivalent amount of a pharmaceutically acceptable salt thereof, and about 40 mg of the neurosteroid and the second composition can comprise about 100 mg of testosterone. In some aspects, the first composition can comprise or about 60 mg of the SERM, or an equivalent amount of a pharmaceutically acceptable salt thereof, and about 40 mg of the neurosteroid and the second composition can comprise about 200 mg of testosterone. In some aspects, the first composition can comprise about 80 mg of the SERM, or an equivalent amount of a pharmaceutically acceptable salt thereof, and about 60 mg of the neurosteroid and the second composition can comprise about 50 mg of testosterone. In some aspects, the first composition can comprise about 80 mg of the SERM, or an equivalent amount of a pharmaceutically acceptable salt thereof, and about 60 mg of the neurosteroid and a second composition can comprise about 100 mg of testosterone. In some aspects, the first composition can comprise about 80 mg of the SERM, or an equivalent amount of a pharmaceutically acceptable salt thereof, and about 60 mg of the neurosteroid and a second composition can comprise about 200 mg of testosterone. In some aspects, the first composition can comprise about 100 mg of the SERM, or an equivalent amount of a pharmaceutically acceptable salt thereof, and about 60 mg of the neurosteroid and a second composition can comprise about 50 mg of testosterone. In some aspects, the first composition can comprise about 100 mg of the SERM, or an equivalent amount of a pharmaceutically acceptable salt thereof, and about 60 mg of the neurosteroid and a second composition can comprise about 100 mg of testosterone. In some aspects, the first composition can comprise about 100 mg of the SERM, or an equivalent amount of a pharmaceutically acceptable salt thereof, and about 60 mg of the neurosteroid and a second composition can comprise about 200 mg of testosterone. In some aspects, the first composition can comprise about 120 mg of the SERM, or an equivalent amount of a pharmaceutically acceptable salt thereof, and about 80 mg of the neurosteroid and a second composition can comprise about 50 mg of testosterone. In some aspects, the first composition can comprise about 120 mg of the SERM, or an equivalent amount of a pharmaceutically acceptable salt thereof, and about 80 mg of the neurosteroid and a second composition can comprise about 100 mg of testosterone. In some aspects, the first composition can comprise about 120 mg of the SERM, or an equivalent amount of a pharmaceutically acceptable salt thereof, and about 80 mg of the neurosteroid and a second composition can comprise about 200 mg of testosterone. In some aspects, the first composition can comprise about 150 mg of the SERM, or an equivalent amount of a pharmaceutically acceptable salt thereof, and about 100 mg of the neurosteroid and a second composition can comprise about 50 mg of testosterone. In some aspects, the first composition can comprise about 150 mg of the SERM, or an equivalent amount of a pharmaceutically acceptable salt thereof, and about 100 mg of the neurosteroid and a second composition can comprise about 100 mg of testosterone. In some aspects, the first composition can comprise about 150 mg of the SERM, or an equivalent amount of a pharmaceutically acceptable salt thereof, and about 100 mg of the neurosteroid and a second composition can comprise about 200 mg of testosterone.

In some aspects, the first composition can comprise about 5 mg of enclomiphene, or an equivalent amount of a pharmaceutically acceptable salt thereof, and about 2.5 mg of pregnenolone and the second composition can comprise about 50 mg of testosterone. In some aspects, the first composition can comprise about 5 mg of enclomiphene, or an equivalent amount of a pharmaceutically acceptable salt thereof, and about 2.5 mg of pregnenolone and the second composition can comprise about 100 mg of testosterone. In some aspects, the first composition can comprise about 5 mg of enclomiphene, or an equivalent amount of a pharmaceutically acceptable salt thereof, and about 2.5 mg of pregnenolone and the second composition can comprise about 200 mg of testosterone. In some aspects, the first composition can comprise about 10 mg of enclomiphene, or an equivalent amount of a pharmaceutically acceptable salt thereof, and about 2.5 mg of pregnenolone and the second composition can comprise about 50 mg of testosterone. In some aspects, the first composition can comprise about 10 mg of enclomiphene, or an equivalent amount of a pharmaceutically acceptable salt thereof, and about 2.5 mg of pregnenolone and the second composition can comprise about 100 mg of testosterone. In some aspects, the first composition can comprise about 10 mg of enclomiphene, or an equivalent amount of a pharmaceutically acceptable salt thereof, and about 2.5 mg of pregnenolone and the second composition can comprise about 200 mg of testosterone. In some aspects, the first composition can comprise about 12.5 mg of enclomiphene, or an equivalent amount of a pharmaceutically acceptable salt thereof, and about 5 mg of pregnenolone and the second composition can comprise about 50 mg of testosterone. In some aspects, the first composition can comprise about 12.5 mg of enclomiphene, or an equivalent amount of a pharmaceutically acceptable salt thereof, and about 5 mg of pregnenolone and the second composition can comprise about 100 mg of testosterone. In some aspects, the first composition can comprise about 12.5 mg of enclomiphene, or an equivalent amount of a pharmaceutically acceptable salt thereof, and about 5 mg of pregnenolone and the second composition can comprise about 200 mg of testosterone. In some aspects, the first composition can comprise about 25 mg of enclomiphene, or an equivalent amount of a pharmaceutically acceptable salt thereof, and about 20 mg of the neurosteroid and the second composition can comprise about 50 mg of testosterone. In some aspects, the first composition can comprise about 25 mg of enclomiphene, or an equivalent amount of a pharmaceutically acceptable salt thereof, and about 20 mg of the neurosteroid and the second composition can comprise about 100 mg of testosterone. In some aspects, the first composition can comprise about 25 mg of enclomiphene, or an equivalent amount of a pharmaceutically acceptable salt thereof, and about 20 mg of the neurosteroid and the second composition can comprise about 200 mg of testosterone. In some aspects, the first composition can comprise or about 50 mg of enclomiphene, or an equivalent amount of a pharmaceutically acceptable salt thereof, and about 40 mg of the neurosteroid and the second composition can comprise about 50 mg of testosterone. In some aspects, the first composition can comprise or about 50 mg of enclomiphene, or an equivalent amount of a pharmaceutically acceptable salt thereof, and about 40 mg of the neurosteroid and the second composition can comprise about 100 mg of testosterone. In some aspects, the first composition can comprise or about 50 mg of enclomiphene, or an equivalent amount of a pharmaceutically acceptable salt thereof, and about 40 mg of the neurosteroid and the second composition can comprise about 200 mg of testosterone. In some aspects, the first composition can comprise or about 100 mg of enclomiphene, or an equivalent amount of a pharmaceutically acceptable salt thereof, and about 60 mg of the neurosteroid and the second composition can comprise about 50 mg of testosterone. In some aspects, the first composition can comprise or about 100 mg of enclomiphene, or an equivalent amount of a pharmaceutically acceptable salt thereof, and about 60 mg of the neurosteroid and the second composition can comprise about 100 mg of testosterone. In some aspects, the first composition can comprise or about 100 mg of enclomiphene, or an equivalent amount of a pharmaceutically acceptable salt thereof, and about 60 mg of the neurosteroid and the second composition can comprise about 200 mg of testosterone. In some aspects, the first composition can comprise or about 150 mg of enclomiphene, or an equivalent amount of a pharmaceutically acceptable salt thereof, and about 100 mg of the neurosteroid and the second composition can comprise about 50 mg of testosterone. In some aspects, the first composition can comprise or about 150 mg of enclomiphene, or an equivalent amount of a pharmaceutically acceptable salt thereof, and about 100 mg of the neurosteroid and the second composition can comprise about 100 mg of testosterone. In some aspects, the first composition can comprise or about 150 mg of enclomiphene, or an equivalent amount of a pharmaceutically acceptable salt thereof, and about 100 mg of the neurosteroid and the second composition can comprise about 200 mg of testosterone.

In some aspects, the first composition can comprise about 5 mg of clomiphene, or an equivalent amount of a pharmaceutically acceptable salt thereof, and about 2.5 mg of pregnenolone and the second composition can comprise about 50 mg of testosterone. In some aspects, the first composition can comprise about 5 mg of clomiphene, or an equivalent amount of a pharmaceutically acceptable salt thereof, and about 2.5 mg of pregnenolone and the second composition can comprise about 100 mg of testosterone. In some aspects, the first composition can comprise about 5 mg of clomiphene, or an equivalent amount of a pharmaceutically acceptable salt thereof, and about 2.5 mg of pregnenolone and the second composition can comprise about 200 mg of testosterone. In some aspects, the first composition can comprise about 10 mg of clomiphene, or an equivalent amount of a pharmaceutically acceptable salt thereof, and about 2.5 mg of pregnenolone and the second composition can comprise about 50 mg of testosterone. In some aspects, the first composition can comprise about 10 mg of clomiphene, or an equivalent amount of a pharmaceutically acceptable salt thereof, and about 2.5 mg of pregnenolone and the second composition can comprise about 100 mg of testosterone. In some aspects, the first composition can comprise about 10 mg of clomiphene, or an equivalent amount of a pharmaceutically acceptable salt thereof, and about 2.5 mg of pregnenolone and the second composition can comprise about 200 mg of testosterone. In some aspects, the first composition can comprise about 12.5 mg of clomiphene, or an equivalent amount of a pharmaceutically acceptable salt thereof, and about 5 mg of pregnenolone and the second composition can comprise about 50 mg of testosterone. In some aspects, the first composition can comprise about 12.5 mg of clomiphene, or an equivalent amount of a pharmaceutically acceptable salt thereof, and about 5 mg of pregnenolone and the second composition can comprise about 100 mg of testosterone. In some aspects, the first composition can comprise about 12.5 mg of clomiphene, or an equivalent amount of a pharmaceutically acceptable salt thereof, and about 5 mg of pregnenolone and the second composition can comprise about 200 mg of testosterone. In some aspects, the first composition can comprise about 25 mg of clomiphene, or an equivalent amount of a pharmaceutically acceptable salt thereof, and about 20 mg of the neurosteroid and the second composition can comprise about 50 mg of testosterone. In some aspects, the first composition can comprise about 25 mg of clomiphene, or an equivalent amount of a pharmaceutically acceptable salt thereof, and about 20 mg of the neurosteroid and the second composition can comprise about 100 mg of testosterone. In some aspects, the first composition can comprise about 25 mg of clomiphene, or an equivalent amount of a pharmaceutically acceptable salt thereof, and about 20 mg of the neurosteroid and the second composition can comprise about 200 mg of testosterone. In some aspects, the first composition can comprise or about 50 mg of clomiphene, or an equivalent amount of a pharmaceutically acceptable salt thereof, and about 40 mg of the neurosteroid and the second composition can comprise about 50 mg of testosterone. In some aspects, the first composition can comprise or about 50 mg of clomiphene, or an equivalent amount of a pharmaceutically acceptable salt thereof, and about 40 mg of the neurosteroid and the second composition can comprise about 100 mg of testosterone. In some aspects, the first composition can comprise or about 50 mg of clomiphene, or an equivalent amount of a pharmaceutically acceptable salt thereof, and about 40 mg of the neurosteroid and the second composition can comprise about 200 mg of testosterone. In some aspects, the first composition can comprise or about 100 mg of clomiphene, or an equivalent amount of a pharmaceutically acceptable salt thereof, and about 60 mg of the neurosteroid and the second composition can comprise about 50 mg of testosterone. In some aspects, the first composition can comprise or about 100 mg of clomiphene, or an equivalent amount of a pharmaceutically acceptable salt thereof, and about 60 mg of the neurosteroid and the second composition can comprise about 100 mg of testosterone. In some aspects, the first composition can comprise or about 100 mg of clomiphene, or an equivalent amount of a pharmaceutically acceptable salt thereof, and about 60 mg of the neurosteroid and the second composition can comprise about 200 mg of testosterone. In some aspects, the first composition can comprise or about 150 mg of clomiphene, or an equivalent amount of a pharmaceutically acceptable salt thereof, and about 100 mg of the neurosteroid and the second composition can comprise about 50 mg of testosterone. In some aspects, the first composition can comprise or about 150 mg of clomiphene, or an equivalent amount of a pharmaceutically acceptable salt thereof, and about 100 mg of the neurosteroid and the second composition can comprise about 100 mg of testosterone. In some aspects, the first composition can comprise or about 150 mg of clomiphene, or an equivalent amount of a pharmaceutically acceptable salt thereof, and about 100 mg of the neurosteroid and the second composition can comprise about 200 mg of testosterone.

In some aspects, the first composition can comprise about 5 mg of toremifene, or an equivalent amount of a pharmaceutically acceptable salt thereof, and about 2.5 mg of pregnenolone and the second composition can comprise about 50 mg of testosterone. In some aspects, the first composition can comprise about 5 mg of toremifene, or an equivalent amount of a pharmaceutically acceptable salt thereof, and about 2.5 mg of pregnenolone and the second composition can comprise about 100 mg of testosterone. In some aspects, the first composition of the pharmaceutical combination can comprise about 5 mg of toremifene, or an equivalent amount of a pharmaceutically acceptable salt thereof, and about 2.5 mg of pregnenolone and the second composition can comprise about 200 mg of testosterone. In some aspects, the first composition can comprise about 10 mg of toremifene, or an equivalent amount of a pharmaceutically acceptable salt thereof, and about 2.5 mg of pregnenolone and the second composition can comprise about 50 mg of testosterone. In some aspects, the first composition can comprise about 10 mg of toremifene, or an equivalent amount of a pharmaceutically acceptable salt thereof, and about 2.5 mg of pregnenolone and the second composition can comprise about 100 mg of testosterone. In some aspects, the first composition of the pharmaceutical combination can comprise about 10 mg of toremifene, or an equivalent amount of a pharmaceutically acceptable salt thereof, and about 2.5 mg of pregnenolone and the second composition can comprise about 200 mg of testosterone. In some aspects, the first composition can comprise about 20 mg of toremifene, or an equivalent amount of a pharmaceutically acceptable salt thereof, and about 10 mg of the neurosteroid and the second composition can comprise about 50 mg of testosterone. In some aspects, the first composition can comprise about 20 mg of toremifene, or an equivalent amount of a pharmaceutically acceptable salt thereof, and about 10 mg of the neurosteroid and the second composition can comprise about 100 mg of testosterone. In some aspects, the first composition can comprise about 20 mg of toremifene, or an equivalent amount of a pharmaceutically acceptable salt thereof, and about 10 mg of the neurosteroid and the second composition can comprise about 200 mg of testosterone. In some aspects, the first composition can comprise about 40 mg of toremifene, or an equivalent amount of a pharmaceutically acceptable salt thereof, and about 20 mg of the neurosteroid and the second composition can comprise about 50 mg of testosterone. In some aspects, the first composition can comprise about 40 mg of toremifene, or an equivalent amount of a pharmaceutically acceptable salt thereof, and about 20 mg of the neurosteroid and the second composition can comprise about 100 mg of testosterone. In some aspects, the first composition can comprise about 40 mg of toremifene, or an equivalent amount of a pharmaceutically acceptable salt thereof, and about 20 mg of the neurosteroid and the second composition can comprise about 200 mg of testosterone. In some aspects, the first composition can comprise about 60 mg of toremifene, or an equivalent amount of a pharmaceutically acceptable salt thereof, and about 40 mg of the neurosteroid and the second composition can comprise about 50 mg of testosterone. In some aspects, the first composition can comprise about 60 mg of toremifene, or an equivalent amount of a pharmaceutically acceptable salt thereof, and about 40 mg of the neurosteroid and the second composition can comprise about 100 mg of testosterone. In some aspects, the first composition can comprise or about 60 mg of toremifene, or an equivalent amount of a pharmaceutically acceptable salt thereof, and about 40 mg of the neurosteroid and the second composition can comprise about 200 mg of testosterone. In some aspects, the first composition can comprise or about 80 mg of toremifene, or an equivalent amount of a pharmaceutically acceptable salt thereof, and about 60 mg of the neurosteroid and the second composition can comprise about 50 mg of testosterone. In some aspects, the first composition can comprise or about 80 mg of toremifene, or an equivalent amount of a pharmaceutically acceptable salt thereof, and about 60 mg of the neurosteroid and the second composition can comprise about 100 mg of testosterone. In some aspects, the first composition can comprise or about 80 mg of toremifene, or an equivalent amount of a pharmaceutically acceptable salt thereof, and about 60 mg of the neurosteroid and the second composition can comprise about 200 mg of testosterone. In some aspects, the first composition can comprise or about 100 mg of toremifene, or an equivalent amount of a pharmaceutically acceptable salt thereof, and about 60 mg of the neurosteroid and the second composition can comprise about 50 mg of testosterone. In some aspects, the first composition can comprise or about 100 mg of toremifene, or an equivalent amount of a pharmaceutically acceptable salt thereof, and about 60 mg of the neurosteroid and the second composition can comprise about 100 mg of testosterone. In some aspects, the first composition can comprise or about 100 mg of toremifene, or an equivalent amount of a pharmaceutically acceptable salt thereof, and about 60 mg of the neurosteroid and the second composition can comprise about 200 mg of testosterone. In some aspects, the first composition can comprise or about 120 mg of toremifene, or an equivalent amount of a pharmaceutically acceptable salt thereof, and about 80 mg of the neurosteroid and the second composition can comprise about 50 mg of testosterone. In some aspects, the first composition can comprise or about 120 mg of toremifene, or an equivalent amount of a pharmaceutically acceptable salt thereof, and about 80 mg of the neurosteroid and the second composition can comprise about 100 mg of testosterone. In some aspects, the first composition can comprise or about 120 mg of toremifene, or an equivalent amount of a pharmaceutically acceptable salt thereof, and about 80 mg of the neurosteroid and the second composition can comprise about 200 mg of testosterone.

In some aspects, the pharmaceutical combination can further comprise a 5α-reductase inhibitor. In some aspects, the first composition comprises the 5α-reductase inhibitor in an amount or range as previously disclosed herein. In some aspects, the pharmaceutical combination comprises a third composition comprising the 5α-reductase inhibitor in an amount or range as previously disclosed herein. In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects, the 5α-reductase inhibitor can be dutasteride. In some aspects, the 5α-reductase inhibitor can be finasteride.

In some aspects, the pharmaceutical combination can further comprise an aromatase inhibitor. In some aspects, the first composition can comprise the aromatase inhibitor in an amount or range as previously disclosed herein. In some aspects, the pharmaceutical combination can further comprise a third composition comprising the aromatase inhibitor in an amount or range as previously disclosed herein. In some aspects, the aromatase inhibitor can be selected from the group consisting of atamestane, exemestane, and formestane, and non-steroids, such as aminoglutethimide, roglethimide, pyridoglutethimide, trilostane, testolactone, vorozole, fadrozole, anastrozole, letrozole, and combinations thereof. In some aspects, the aromatase inhibitor can be anastrozole.

In some aspects, the pharmaceutical combination can further comprise ketoconazole. In some aspects, the first composition can comprise ketoconazole. In some aspects, the pharmaceutical combination can further comprise a third composition comprising ketoconazole.

The present disclosure is also directed to a pharmaceutical combination comprising a first composition comprising a therapeutically effective amount of a selective estrogen receptor modulator (SERM) in a form suitable for topical or transdermal administration, and a second composition comprising testosterone in a form suitable for topical or transdermal administration. In some aspects, the first composition and the second composition can be administered simultaneously, concurrently, or sequentially.

In some aspects, the first composition comprising the therapeutically effective amount of the SERM can be in a form suitable for topical or transdermal administration. In some aspects, the first composition can be in a form suitable for topical administration, including a lotion, emulsion, cream, gel, ointment, foam, liquid, paste or other topically administrable form. In some aspects, the first composition comprising the therapeutically effective amount of the SERM can be in a form suitable for transdermal administration, including a transdermal patch, transdermal lotion, transdermal cream, transdermal gel, transdermal ointment, transdermal foam, transdermal liquid, transdermal paste or other transdermally administrable form.

In some aspects, the second composition comprising testosterone can be in a form suitable for topical administration. In some aspects, the first composition can be in a form suitable for topical administration, including a lotion, emulsion, cream, gel, ointment, foam, liquid, paste or other topically administrable form. In some aspects, the second composition comprising testosterone can be in a form suitable for transdermal administration. In some aspects, the second composition can be suitable for transdermal administration, including a transdermal patch, transdermal lotion, transdermal cream, transdermal gel, transdermal ointment, transdermal foam, transdermal liquid, transdermal paste or other transdermally administrable form.

In some aspects, the first composition can be the pharmaceutical composition, described above, comprising therapeutically effective amounts of the SERM and the steroid hormone. In some aspects, the steroid hormone is selected from the group consisting of a neurosteroid, DHEA, estrogen, DHT, and combinations thereof. In some aspects, the steroid hormone is a neurosteroid.

In other aspects, the combination can comprise a first composition comprising a therapeutically effective amount of a selective estrogen receptor modulator (SERM), a second composition comprising testosterone in a form suitable for topical or transdermal administration, and a third composition comprising a therapeutically effective amount of the neurosteroid. In some aspects, the third composition comprising the therapeutically effective amount of the neurosteroid can be in a form suitable for oral administration. In some aspects of this combination, the third composition comprising the therapeutically effective amount of the neurosteroid can be in a form suitable for sublingual administration. In some aspects, the third composition comprising the therapeutically effective amount of the neurosteroid in a form suitable for sublingual administration can be a tablet. In some aspects, the third composition comprising the therapeutically effective amount of the neurosteroid can be in a form suitable for topical administration. In some aspects, the third composition comprising the therapeutically effective amount of the neurosteroid in a form suitable for topical administration can be a topical cream. In some aspects, the third composition comprising the therapeutically effective amount of the neurosteroid can be in a form suitable for transdermal administration. In some aspects, the third composition comprising the therapeutically effective amount of the neurosteroid in a form suitable for transdermal administration can be a transdermal patch. In some aspects, the third composition can comprise the neurosteroid in an amount or range as previously disclosed herein. In some aspects, the neurosteroid can be pregnenolone. In some aspects, the third composition can comprise pregnenolone in an amount or range as previously disclosed herein. In certain aspects of the combination comprising the three compositions, the first, second, and third compositions, can be administered simultaneously, concurrently, or sequentially.

In some aspects, the first composition of the pharmaceutical combination can comprise the SERM in an amount or range as previously disclosed herein. In some aspects, the first composition can comprise enclomiphene in an amount or range as previously disclosed herein. In some aspects, the first composition can comprise clomiphene in an amount or range as previously disclosed herein. In some aspects, the first composition can comprise toremifene in an amount or range as previously disclosed herein.

In some aspects, the first composition can further comprise a neurosteroid in an amount or range as previously disclosed herein. In some aspects, the first composition can further comprise pregnenolone in an amount or range as previously disclosed herein.

In some aspects, the first composition can further comprise the excipients in an amount or range as previously disclosed herein.

In some aspects, the second composition of the pharmaceutical combination can comprise testosterone in an amount or range as previously disclosed herein. In some aspects, the testosterone can be natural or native testosterone (also known as testosterone base or unmodified testosterone or unesterified testosterone) or an isomer or derivative thereof. In some aspects, the testosterone can be native testosterone. In some aspects, the testosterone can be a testosterone ester.

In some aspects, the second composition can further comprise at least one pharmaceutically acceptable excipient in an amount or range as previously disclosed herein.

In some aspects, the pharmaceutical combination can further comprise a 5α-reductase inhibitor. In some aspects, the first composition further comprises the 5α-reductase inhibitor in an amount or range as previously disclosed herein. In some aspects, the pharmaceutical combination can further comprise a third composition comprising the 5α-reductase inhibitor in an amount or range as previously disclosed herein. In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects, the 5α-reductase inhibitor can be dutasteride. In some aspects, the 5α-reductase inhibitor can be finasteride.

In some aspects, the pharmaceutical combination can further comprise an aromatase inhibitor. In some aspects, the first composition further comprises the aromatase inhibitor in an amount or range as previously disclosed herein. In some aspects, the pharmaceutical combination can further comprise a third composition comprising the aromatase inhibitor in an amount or range as previously disclosed herein. In some aspects, the aromatase inhibitor can be selected from the group consisting of atamestane, exemestane, and formestane, and non-steroids, such as aminoglutethimide, roglethimide, pyridoglutethimide, trilostane, testolactone, vorozole, fadrozole, anastrozole, letrozole, and combinations thereof. In some aspects, the aromatase inhibitor can be anastrozole. In some aspects, the aromatase inhibitor can be exemestane.

In some aspects, the pharmaceutical combination can further comprise ketoconazole. In some aspects, the first composition further comprises ketoconazole. In some aspects, the pharmaceutical combination can further comprise a third composition comprising ketoconazole.

In some aspects, the pharmaceutical combination can comprise a first composition in a form suitable for topical or transdermal administration comprising about 5 mg to about 150 mg of enclomiphene citrate; and a second composition in a form suitable for topical or transdermal administration comprising about 50 mg to about 400 mg of native testosterone or testosterone ester.

The present disclosure is also directed to a pharmaceutical combination comprising a first composition comprising a therapeutically effective amount of a selective estrogen receptor modulator (SERM) and testosterone in a form suitable for topical or transdermal administration. In some aspects, the pharmaceutical combination comprises a second composition comprising a neurosteroid.

Methods of Treatment

The present disclosure is further directed to the method of increasing testosterone levels in a subject in need thereof comprising administering the pharmaceutical composition or the pharmaceutical combination described herein. In some aspects, the method can at least partially reduce the suppression of endogenous testosterone and maintain baseline levels of LH, and FSH production. In some aspects, the method can maintain testicular function, size, and volume and reduce risk of testicular shrinkage, impaired fertility, and dependence. In some aspects, the subject is a male mammal or human. In some aspects, the subject is a mammal or human whose serum testosterone levels fall below 400 ng/dL resulting in a low testosterone diagnosis. A blood serum testosterone test can be used to determine endogenous testosterone levels. In some aspects, the subject is a mammal or human whose symptoms include, but are not limited to, low libido, low energy, decreased strength, decreased endurance, erectile dysfunction, and combinations thereof. In some aspects, the subject is a mammal or human with symptomatic hypogonadism with normal endocrine function (e.g., normal LH, FSH, and testosterone levels), alternatively known as "functional hypogonadism." In some aspects, the subject is a mammal or human with secondary hypogonadism. In some aspects, the subject is a mammal or human with type II diabetes, metabolic syndrome, osteoporosis, infertility, and combinations thereof.

In some aspects of the method, the pharmaceutical composition can be administered once a day. In some aspects of the method, the pharmaceutical composition can be administered twice a day. In some aspects of the method, the pharmaceutical composition can be administered three times a day. In some aspects of the method, the pharmaceutical composition can be administered four times a day.

In some aspects of the method, the pharmaceutical combination can be administered once a day. In some aspects of the method, the pharmaceutical combination can be administered twice a day. In some aspects of the method, the pharmaceutical combination can be administered three times a day. In some aspects of the method, the pharmaceutical combination can be administered four times a day.

In some aspects of the method, the pharmaceutical composition comprising a SERM, e.g., enclomiphene, or an equivalent amount of a pharmaceutically acceptable salt thereof, and a neurosteroid, e.g., pregnenolone, can be administered to the subject. In some aspects of the method, the pharmaceutical composition can comprise about 1.5 mg of enclomiphene, or an equivalent amount of a pharmaceutically acceptable salt thereof, and about 5 mg of pregnenolone. In some aspects of the method, the pharmaceutical composition can comprise about 2 mg of enclomiphene, or an equivalent amount of a pharmaceutically acceptable salt thereof, and about 5 mg of pregnenolone; about 3.125 mg of enclomiphene, or an equivalent amount of a pharmaceutically acceptable salt thereof, and about 2.5 mg of pregnenolone; about 3.125 mg of enclomiphene, or an equivalent amount of a pharmaceutically acceptable salt thereof, and about 5 mg of pregnenolone; about 4 mg of enclomiphene, or an equivalent amount of a pharmaceutically acceptable salt thereof, and about 5 mg of pregnenolone; about 6.25 mg of enclomiphene, or an equivalent amount of a pharmaceutically acceptable salt thereof, and about 5 mg of pregnenolone; about 12.5 mg of enclomiphene, or an equivalent amount of a pharmaceutically acceptable salt thereof, and about 10 mg of pregnenolone; about 25 mg of enclomiphene, or an equivalent amount of a pharmaceutically acceptable salt thereof, and about 20 mg of pregnenolone; or about 50 mg of enclomiphene, or an equivalent amount of a pharmaceutically acceptable salt thereof, and about 40 mg of pregnenolone.

In some aspects of the method, the pharmaceutical combination comprising a first composition comprising a SERM, e.g., enclomiphene, or an equivalent amount of a pharmaceutically acceptable salt thereof, and a second composition comprising testosterone in a form suitable for oral administration, can be administered to the subject. In some aspects of the method, the first composition can comprise about 1.5 mg of enclomiphene, or an equivalent amount of a pharmaceutically acceptable salt thereof, and the second composition can comprise about 200 mg of testosterone. In some aspects of the method, the first composition can comprise about 2 mg of enclomiphene, or an equivalent amount of a pharmaceutically acceptable salt thereof, and the second composition can comprise 200 mg of testosterone. In some aspects of the method, the first composition can comprise about 3.125 mg of enclomiphene, or an equivalent amount of a pharmaceutically acceptable salt thereof, and the second composition can comprise about 200 mg of testosterone. In some aspects of the method, the first composition can comprise about 4 mg of enclomiphene, or an equivalent amount of a pharmaceutically acceptable salt thereof, and the second composition can comprise about 200 mg of testosterone. In some aspects of the method, the first composition can comprise about 6.25 mg of enclomiphene, or an equivalent amount of a pharmaceutically acceptable salt thereof, and the second composition can comprise about 200 mg of testosterone. In some aspects of the method, the first composition can comprise about 12.5 mg of enclomiphene, or an equivalent amount of a pharmaceutically acceptable salt thereof, and the second composition can comprise about 200 mg of testosterone. In some aspects of the method, the first composition can comprise about 25 mg of enclomiphene, or an equivalent amount of a pharmaceutically acceptable salt thereof, and the second composition can comprise about 200 mg of testosterone. In some aspects of the method, the first composition can comprise about 50 mg of enclomiphene, or an equivalent amount of a pharmaceutically acceptable salt thereof, and the second composition can comprise about 200 mg of testosterone.

In some aspects of the method, the pharmaceutical combination comprising a first composition comprising a SERM, e.g., enclomiphene, or an equivalent amount of a pharmaceutically acceptable salt thereof, and a second composition comprising testosterone in a form suitable for topical or transdermal administration, can be administered to the subject. In some aspects of the method, the first composition can comprise enclomiphene, clomiphene, or toremifene, or a pharmaceutically acceptable salt thereof, in an amount or range as previously disclosed herein, and the second composition can comprise testosterone in an amount or range as previously disclosed herein.

In some aspects of the method, the pharmaceutical combination comprising a first composition comprising a SERM (e.g., enclomiphene), or an equivalent amount of a pharmaceutically acceptable salt thereof, and a neurosteroid (e.g., pregnenolone), and a second composition comprising testosterone in a form suitable for oral administration, can be administered to the subject. In some aspects of the method, the first composition can comprise about 1.5 mg of enclomiphene, or an equivalent amount of a pharmaceutically acceptable salt thereof, and about 5 mg of pregnenolone and the second composition can comprise about 200 mg of testosterone. In some aspects of the method, the first composition can comprise about 2 mg of enclomiphene, or an equivalent amount of a pharmaceutically acceptable salt thereof, and about 5 mg of pregnenolone and the second composition can comprise about 200 mg of testosterone. In some aspects of the method, the first composition can comprise about 3.125 mg of enclomiphene, or an equivalent amount of a pharmaceutically acceptable salt thereof, and about 2.5 mg of pregnenolone and the second composition can comprise about 200 mg of testosterone. In some aspects of the method, the first composition can comprise about 3.125 mg of enclomiphene, or an equivalent amount of a pharmaceutically acceptable salt thereof, and about 5 mg of pregnenolone and the second composition can comprise about 200 mg of testosterone. In some aspects of the method, the first composition can comprise about 4 mg of enclomiphene, or an equivalent amount of a pharmaceutically acceptable salt thereof, and about 5 mg of pregnenolone and the second composition can comprise about 200 mg of testosterone. In some aspects of the method, the first composition can comprise about 6.25 mg of enclomiphene, or an equivalent amount of a pharmaceutically acceptable salt thereof, and about 5 mg of pregnenolone and the second composition can comprise about 200 mg of testosterone. In some aspects of the method, the first composition can comprise about 12.5 mg of enclomiphene, or an equivalent amount of a pharmaceutically acceptable salt thereof, and about 10 mg of pregnenolone and the second composition can comprise about 200 mg of testosterone. In some aspects of the method, the first composition can comprise about 25 mg of enclomiphene, or an equivalent amount of a pharmaceutically acceptable salt thereof, and about 20 mg of pregnenolone and the second composition can comprise about 200 mg of testosterone. In some aspects of the method, the first composition can comprise about 50 mg of enclomiphene, or an equivalent amount of a pharmaceutically acceptable salt thereof, and about 40 mg of pregnenolone and the second composition can comprise about 200 mg of testosterone.

In some aspects of the method, the pharmaceutical combination comprising a first composition comprising a SERM (e.g., enclomiphene), or an equivalent amount of a pharmaceutically acceptable salt thereof, and a neurosteroid (e.g., pregnenolone), and a second composition comprising testosterone in a form suitable for topical or transdermal administration, can be administered to the subject. In some aspects of the method, the first composition can comprise enclomiphene, clomiphene, or toremifene, or a pharmaceutically acceptable salt thereof, and pregnenolone, in an amount or range as previously disclosed herein, and the second composition can comprise testosterone in an amount or range as previously disclosed herein.

In some aspects of the method, the pharmaceutical composition comprising a SERM (e.g., enclomiphene), or an equivalent amount of a pharmaceutically acceptable salt thereof, and testosterone in a form suitable for topical or transdermal administration, can be administered to the subject. In some aspects of the method, the composition can comprise enclomiphene, or a pharmaceutically acceptable salt thereof, and testosterone, in an amount or range as previously disclosed herein. In some aspects of the method, the composition can comprise clomiphene, or a pharmaceutically acceptable salt thereof, and testosterone, in an amount or range as previously disclosed herein. In some aspects of the method, the composition can comprise toremifene, or a pharmaceutically acceptable salt thereof, or toremifene, in an amount or range as previously disclosed herein.

In some aspects of the method, the pharmaceutical composition or the pharmaceutical combination can further comprise a 5α-reductase inhibitor. In some aspects of the method, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects of the method, the 5α-reductase inhibitor can be dutasteride. In some aspects of the method, the 5α-reductase inhibitor can be finasteride.

In some aspects of the method, the pharmaceutical composition or the pharmaceutical combination can further comprise an aromatase inhibitor, a compound that inhibits the action of aromatase, the enzyme that converts androgens into estrogens by aromatization. In some aspects of the method, the aromatase inhibitor is selected from the group consisting of atamestane, exemestane, and formestane, and non-steroids, such as aminoglutethimide, roglethimide, pyridoglutethimide, trilostane, testolactone, vorozole, fadrozole, anastrozole, letrozole, and combinations thereof. In some aspects of the method, the aromatase inhibitor can be anastrozole. In some aspects, the aromatase inhibitor can be exemestane.

In some aspects, the present disclosure provides a method of increasing a subject's total testosterone level by at least about 50%, about 60%, about 70%, about 80%, about 90%, or about 100% compared to the subject's baseline total testosterone level. In other aspects, the present disclosure provides a method of increasing a subject's total testosterone by at least about 150%, about 200%, about 250%, or about 300% compared to the subject's baseline total testosterone level. In certain aspects, the method described herein can achieve the desired increase in total testosterone levels about 1 hour, about 2 hours, about 3 hours, about 4 hours, or about 5 hours after administration.

In some aspects, the present disclosure provides a method of increasing a subject's free testosterone level by at least about 50%, about 60%, about 70%, about 80%, about 90%, or about 100% compared to the subject's baseline free testosterone level. In other aspects, the present disclosure provides a method of increasing a subject's free testosterone level by at least about 150%, about 200%, about 250%, about 300%, about 350%, or about 400% compared to the subject's baseline free testosterone level. In certain aspects, the method described herein can achieve the desired increase in free testosterone levels about 1 hour, about 2 hours, about 3 hours, about 4 hours, or about 5 hours after administration.

In some aspects, the present disclosure provides a method of maintaining a subject's baseline LH level. In some aspects, the subject's baseline LH level can be in a clinically normal range of 1 IU/L or more. In some aspects, the present disclosure provides a method of maintaining a subject's LH level in a clinically normal range (1 IU/L or more).

In some aspects, the present disclosure provides a method of maintaining a subject's baseline FSH level. In some aspects, the subject's baseline FSH level can be in a clinically normal range of 1 IU/L or more. In some aspects, the present disclosure provides a method of maintaining a subject's FSH level in a clinically normal range (1 IU/L or more).

In some aspects, the present disclosure provides a method of increasing testosterone levels in a subject in need thereof, comprising administering to the subject a first composition comprising about 1 mg to about 50 mg of a selective estrogen receptor modulator in a form suitable for oral or sublingual administration, and a second composition comprising about 100 mg to about 800 mg testosterone in a form suitable for oral administration.

In some aspects, the present disclosure provides a method of increasing testosterone levels in a subject in need thereof, comprising administering to the subject a first composition comprising about 5 mg to about 250 mg of a selective estrogen receptor modulator in a form suitable for oral or sublingual administration, and a second composition comprising about 50 mg to about 800 mg testosterone in a form suitable for topical or transdermal administration.

In some aspects, the present disclosure provides a method of increasing testosterone levels in a subject in need thereof, comprising administering to the subject a first composition comprising about 5 mg to about 250 mg of a selective estrogen receptor modulator in a form suitable for topical or transdermal administration, and a second composition comprising about 50 mg to about 800 mg testosterone in a form suitable for topical or transdermal administration.

In some aspects, the present disclosure provides a method of increasing testosterone levels in a subject in need thereof, comprising administering to the subject a composition comprising about 5 mg to about 250 mg of a selective estrogen receptor modulator and about 50 mg to about 800 mg of testosterone in a form suitable for topical or transdermal administration.

In some aspects, the subject can be a human subject and administering the first and second compositions can increase the subject's total testosterone level by at least about 50%, about 60%, about 70%, about 80%, about 90%, or about 100% compared to the subject's baseline total testosterone level. In some aspects, the subject can be a human subject and administering the first and second compositions can increase the subject's total testosterone level by at least about 150%, about 200%, about 250%, or about 300% compared to the subject's baseline total testosterone level. In some aspects, the method described herein can achieve the desired increase in total testosterone levels about 1 hour, about 2 hours, about 3 hours, about 4 hours, or about 5 hours after administration.

In some aspects, the selective estrogen receptor modulator can be selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof. In some aspects, the selective estrogen receptor modulator can be enclomiphene or a pharmaceutically acceptable salt thereof. In some aspects, the pharmaceutically acceptable salt of enclomiphene can be enclomiphene citrate.

In some aspects, the first composition can comprise about 3 mg, about 3.125 mg, about 6.25 mg, about 12.5 mg, about 25 mg, or about 50 mg of the selective estrogen receptor modulator.

In some aspects, the second composition can comprise about 50 mg, about 100 mg, about 200 mg, about 400 mg, about 600 mg, or about 800 mg of testosterone.

In some aspects, the first composition further can comprise a neurosteroid. In some aspects, the neurosteroid can be selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof. In some aspects, the neurosteroid can be pregnenolone.

In some aspects, the first composition can further comprise about 5 mg to about 40 mg of pregnenolone. In some aspects, the first composition can comprise about 5 mg, about 10 mg, about 20 mg, or about 40 mg of pregnenolone.

In some aspects, the first composition can be in the form of a sublingual tablet. In some aspects, the second composition comprising testosterone in a form suitable for oral administration can be a tablet or capsule.

In some aspects, the first composition can be administered sublingually. In some aspects, the second composition can be administered orally.

In some aspects, the first composition can be in the form of an oral or sublingual tablet or capsule. In some aspects, the second composition comprising testosterone in a form suitable for topical administration can be a lotion, an emulsion, a cream, a gel, an ointment, a foam, a liquid, a paste, or other topically administrable form.

In some aspects, the first composition can be administered orally or sublingually. In some aspects, the second composition can be administered topically to, e.g., the inner arms, wrists, shoulders, upper arms, abdomen, lateral sides of the abdomen, front or inner thighs, and the scrotum.

In some aspects, the first composition can be in the form of an oral or sublingual tablet or capsule. In some aspects, the second composition comprising testosterone in a form suitable for transdermal administration can be a transdermal patch, transdermal lotion, transdermal cream, transdermal gel, transdermal ointment, transdermal foam, transdermal liquid, transdermal paste, or other transdermally administrable form.

In some aspects, the first composition can be administered orally or sublingually. In some aspects, the second composition can be administered transdermally to, e.g., the inner arms, wrists, shoulders, upper arms, abdomen, lateral sides of the abdomen, front or inner thighs, and the scrotum.

In some aspects, the first and second compositions can be administered topically. In some aspects, the first and second compositions can be topically administered to the same body part. In some aspects, the first and second compositions can be topically administered to different body parts.

In some aspects, the first and second compositions can be administered transdermally. In some aspects, the first and second compositions can be transdermally administered to the same body part. In some aspects, the first and second compositions can be transdermally administered to different body parts.

In some aspects, the first composition can be administered topically and the second composition can be administered transdermally. In some aspects, the first composition can be administered transdermally and the second composition can be administered topically.

In some aspects, the method can further comprise administering a 5α-reductase inhibitor. In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some aspects, the 5α-reductase inhibitor can be dutasteride. In some aspects, the method can comprise administering about 0.1 mg to about 5 mg of dutasteride.

In some aspects, the present disclosure provides a method of increasing testosterone levels in a subject in need thereof, comprising administering to the subject a first composition in a form suitable for sublingual administration comprising: about 1 mg to about 50 mg of enclomiphene citrate, cellulose, a non-nutritive sweetener, a flavoring agent, and magnesium stearate; and at least one second composition in a form suitable for oral administration and lymphatic absorption comprising about 200 mg of native testosterone, safflower oil, cellulose, and magnesium stearate.

In some aspects, the present disclosure provides a method of increasing testosterone levels in a subject in need thereof, comprising administering to the subject a first composition in a form suitable for oral administration comprising: about 1 mg to about 150 mg of enclomiphene citrate, cellulose, a non-nutritive sweetener, a flavoring agent, and magnesium stearate; and at least one second composition in a form suitable for topical or transdermal administration comprising: about 50 to about 200 mg of native testosterone (i.e., unmodified or unesterified testosterone) or testosterone ester and at least one pharmaceutically acceptable excipient.

In some aspects, the present disclosure provides a method of increasing testosterone levels in a subject in need thereof, comprising administering to the subject a first composition in a form suitable for topical or transdermal administration comprising: about 5 mg to about 150 mg of enclomiphene citrate and at least one pharmaceutically acceptable excipient; and at least one second composition in a form suitable for topical or transdermal administration comprising: about 50 to about 200 mg of native testosterone (i.e., unmodified or unesterified testosterone) or testosterone ester and at least one pharmaceutically acceptable excipient.

In some aspects, the present disclosure provides a method of increasing testosterone levels in a subject in need thereof, comprising administering to the subject a composition in a form suitable for topical or transdermal administration comprising: about 5 mg to about 150 mg of enclomiphene citrate; about 50 to about 200 mg of native testosterone (i.e., unmodified or unesterified testosterone) or testosterone ester; and at least one pharmaceutically acceptable excipient.

In some aspects, the subject can be a human subject and administering the first and second compositions can increase the subject's total testosterone level by at least about 50%, about 60%, about 70%, about 80%, about 90%, or about 100% compared to the subject's baseline total testosterone level. In some aspects, the subject can be a human subject and administering the first and second compositions can increase the subject's total testosterone level by at least about 150%, about 200%, about 250%, or about 300% compared to the subject's baseline total testosterone level. In some aspects, the method described herein can achieve the desired increase in total testosterone levels about 1 hour, about 2 hours, about 3 hours, about 4 hours, or about 5 hours after administration.

In some aspects, the first composition can comprise about 3 mg, about 3.125 mg, about 6.25 mg, about 12.5 mg, about 25 mg, or about 50 mg of the enclomiphene citrate.

In some aspects, the second composition can comprise about 50 mg, about 100 mg, about 200 mg, about 400 mg, about 600 mg, or about 800 mg of native testosterone.

In some aspects, the first composition can further comprise a neurosteroid. In some aspects, the neurosteroid can be selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof. In some aspects, the neurosteroid can be pregnenolone.

In some aspects, the first composition can further comprise about 5 mg to about 40 mg of pregnenolone. In some aspects, the first composition can comprise about 5 mg, about 10 mg, about 20 mg, or about 40 mg of pregnenolone.

In some aspects, the first composition can be in the form of a sublingual tablet. In some aspects, the second composition comprising native testosterone in a form suitable for oral administration and lymphatic absorption can be a tablet or capsule.

In some aspects, the first composition can be administered sublingually. In some aspects, the second composition can be administered orally.

In some aspects, the method can further comprise administering a 5α-reductase inhibitor. In some aspects, the 5α-reductase inhibitor can be selected from the group consisting of flutamide, nilutamide, enzalutamide, bicalutamide, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, and combinations thereof. In some, the 5α-reductase inhibitor can be dutasteride. In some aspects, the method can comprise administering about 0.1 mg to about 5 mg of dutasteride.

Exemplary Embodiments

The present disclosure provides the additional embodiments:

(1) A composition for sublingual administration comprising:

i) about 1 mg to about 80 mg of enclomiphene; and ii) about 1 mg to about 60 mg of pregnenolone.

(2) The composition of (1), comprising about 1.5 mg to about 50 mg of enclomiphene.

(3) The composition of (1) or (2), comprising about 2 mg to about 40 mg of pregnenolone.

(4) The composition of any one of (1)-(3), comprising about 6.25 mg of enclomiphene.

(5) The composition of any one of (1)-(3), comprising about 12.5 mg of enclomiphene.

(6) The composition of any one of (1)-(3), comprising about 25 mg of enclomiphene.

(7) The composition of any one of (1)-(6), comprising about 5 mg of pregnenolone.

(8) The composition of any one of (1)-(6), comprising about 10 mg of pregnenolone.

(9) The composition of any one of (1)-(6), comprising about 20 mg of pregnenolone.

(10) The composition of any one of (1)-(9), further comprising a filler.

(11) The composition of (10), wherein the filler comprises cellulose.

(12) The composition of any one of (1)-(11), further comprising a sweetener.

(13) The composition of (12), wherein the sweetener is a non-nutritive sweetener.

(14) The composition of (13), wherein the non-nutritive sweetener comprises a mixture of steviol glycosides.

(15) The composition of any one of (1)-(14), further comprising a flavoring agent.

(16) The composition of (15), wherein the flavoring agent is an orange flavoring agent.

(17) The composition of any one of (1)-(16), further comprising a lubricant.

(18) The composition of (17), wherein the lubricant is magnesium stearate.

(19) The composition of any one of (1)-(18), wherein the composition is in the form of a sublingual tablet.

(20) A method of increasing testosterone levels in a subject in need thereof, comprising administering to the subject the composition of any one of (1)-(19).

(21) A pharmaceutical combination, comprising:

i) the composition of any one of (1)-(19); and ii) a second composition comprising testosterone in a form suitable for oral administration.

(22) The combination of (21), wherein the second composition comprising testosterone in a form suitable for oral administration is a tablet or capsule suitable for lymphatic absorption.

(23) The combination of (21) or (22), comprising about 100 mg to about 1,500 mg of testosterone.

(24) The combination of any one of (21)-(23), comprising about 200 mg to about 1,200 mg of testosterone.

(25) The combination of any one of (21)-(24), comprising about 200 mg of testosterone.

(26) The combination of any one of (21)-(24), comprising about 400 mg of testosterone.

(27) The combination of any one of (21)-(24), comprising about 600 mg of testosterone.

(28) The combination of any one of (21)-(24), comprising about 800 mg of testosterone.

(29) The combination of any one of (21)-(28), wherein the second composition comprises an oil.

(30) The combination of (29), wherein the oil comprises safflower oil.

(31) The combination of (29) or (30), wherein the second composition comprises a filler.

(32) The combination of (31), wherein the filler comprises cellulose.

(33) The combination of any one of (29)-(32), wherein the second composition comprises a lubricant.

(34) The combination of (33), wherein the lubricant is magnesium stearate.

(35) A method of increasing testosterone levels in a subject in need thereof, comprising administering the pharmaceutical combination of any one of (21)-(34).

(36) A pharmaceutical combination comprising:

i) a first composition comprising a selective estrogen receptor modulator; and ii) a second composition comprising testosterone in a form suitable for oral administration.

(37) The combination of (36), wherein the selective estrogen receptor modulator is selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof.

(38) The combination of (36) or (37), wherein the selective estrogen receptor modulator is enclomiphene.

(39) The combination of (38), comprising about 1 mg to about 80 mg of enclomiphene.

(40) The combination of (38) or (39), comprising about 2 mg to about 50 mg of enclomiphene.

(41) The combination of any one of (36)-(40), wherein the first composition further comprises a neurosteroid.

(42) The combination of (41), wherein the neurosteroid is selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof.

(43) The combination of (41) or (42), wherein the neurosteroid is pregnenolone.

(44) The combination of (43), comprising about 1 mg to about 80 mg of pregnenolone.

(45) The combination of (43) or (44), comprising about 2 mg to about 40 mg of pregnenolone.

(46) The combination of any one of (36)-(45), wherein the first composition is in a form suitable for sublingual administration.

(47) The combination of (46), wherein the first composition is a sublingual tablet.

(48) The combination of any one of (36)-(47), wherein the second composition comprising testosterone is a tablet or capsule suitable for lymphatic absorption.

(49) The combination of any one of (36)-(48), comprising about 100 mg to about 1,500 mg of testosterone.

(50) The combination of any one of (36)-(49), comprising about 200 mg to about 1,200 mg of testosterone.

(51) The combination of any one of (36)-(50), comprising about 200 mg of testosterone.

(52) The combination of any one of (36)-(50), comprising about 400 mg of testosterone.

(53) The combination of any one of (36)-(50), comprising about 600 mg of testosterone.

(54) The combination of any one of (36)-(50), comprising about 800 mg of testosterone.

(55) The combination of any one of (36)-(54), further comprising a 5α-reductase inhibitor.

(56) The combination of (55), wherein the 5α-reductase inhibitor is dutasteride.

(57) The combination of any one of (36)-(56), further comprising an aromatase inhibitor.

(58) The combination of (57), wherein the aromatase inhibitor is anastrozole.

(59) A method of increasing testosterone levels in a subject in need thereof, comprising administering the pharmaceutical combination of any one of (36)-(58).

(60) A pharmaceutical combination comprising:

i) a first composition comprising about 1 mg to about 50 mg of a selective estrogen receptor modulator; and ii) a second composition comprising about 100 mg to about 800 mg testosterone in a form suitable for oral administration.

(61) The combination of (60), wherein the selective estrogen receptor modulator is selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof.

(62) The combination of (60) or (61), wherein the selective estrogen receptor modulator is enclomiphene or a pharmaceutically acceptable salt thereof.

(63) The combination of (61) or (62), wherein the pharmaceutically acceptable salt of enclomiphene is enclomiphene citrate.

(64) The combination of any one of (60)-(63), wherein the first composition comprises about 3 mg, about 3.125 mg, about 6.25 mg, about 12.5 mg, about 25 mg, or about 50 mg of the selective estrogen receptor modulator.

(65) The combination of any one of (60)-(64), wherein the second composition comprises about 200 mg, about 400 mg, about 600 mg, or about 800 mg of testosterone.

(66) The combination of any one of (60)-(65), wherein the first composition further comprises a neurosteroid.

(67) The combination of (66), wherein the neurosteroid is selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof.

(68) The combination of (66) or (67), wherein the neurosteroid is pregnenolone.

(69) The combination of (68), wherein the first composition comprises about 5 mg to about 40 mg of pregnenolone.

(70) The combination of (68) or (69), wherein the first composition comprises about 5 mg, about 10 mg, about 20 mg, or about 40 mg of pregnenolone.

(71) The combination of any one of (60)-(70), wherein the first composition further comprises a pharmaceutically acceptable excipient.

(72) The combination of (71), wherein the pharmaceutically acceptable excipient is selected from the group consisting of a filler, a sweetener, a flavoring agent, a lubricant, and combinations thereof.

(73) The combination of any one of (60)-(72), wherein the first composition is in the form of a sublingual tablet.

(74) The combination of any one of (60)-(73), wherein the second composition further comprises a pharmaceutically acceptable excipient.

(75) The combination of (74), wherein the pharmaceutically acceptable excipient is selected from the group consisting of an oil, a filler, a lubricant, and combinations thereof.

(76) The combination of any one of (60)-(75), wherein the second composition comprising testosterone in a form suitable for oral administration is a tablet or capsule.

(77) A pharmaceutical combination comprising:

i) a first composition in a form suitable for sublingual administration comprising:
  a) about 1 mg to about 50 mg of enclomiphene citrate;
  b) cellulose;
  c) a non-nutritive sweetener;
  d) a flavoring agent; and
  e) magnesium stearate;

ii) at least one second composition in a form suitable for oral administration and lymphatic absorption comprising:
  a) about 200 mg of native testosterone;
  b) safflower oil;
  c) cellulose; and
  d) magnesium stearate.

(78) A pharmaceutical composition comprising:

i) about 1 mg to about 50 mg of a selective estrogen receptor modulator; and ii) about 100 mg to about 800 mg of testosterone, wherein the pharmaceutical composition is suitable for oral administration, sublingual administration, or a combination thereof.

(79) The composition of (78), wherein the selective estrogen receptor modulator is selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof.

(80) The composition of (78) or (79), wherein the selective estrogen receptor modulator is enclomiphene or a pharmaceutically acceptable salt thereof.

(81) The composition of (79) or (80), wherein the pharmaceutically acceptable salt of enclomiphene is enclomiphene citrate.

(82) The composition of any one of (78)-(81), comprising about 3 mg, about 3.125 mg, about 6.25 mg, about 12.5 mg, about 25 mg, or about 50 mg of the selective estrogen receptor modulator.

(83) The composition of any one of (78)-(82), comprising about 200 mg, about 400 mg, about 600 mg, or about 800 mg of testosterone.

(84) The composition of any one of (78)-(83), further comprising a neurosteroid.

(85) The composition of (84), wherein the neurosteroid is selected from the group consisting of 25-hydroxycholesterol, 3α,5α-androstanediol, 3α,5β-androstanediol, androsterone, etiocholanolone, dihydrotestosterone, 3α-dihydroprogesterone, allopregnanediol, pregnanediol, pregnenolone, anicequol, estratetraenol, caprospinol, dehydroepiandrosterone, and combinations thereof.

(86) The composition of (84) or (85), wherein the neurosteroid is pregnenolone.

(87) The composition of (86), comprising about 5 mg to about 40 mg of pregnenolone.

(88) The composition of (86) or (87), comprising about 5 mg, about 10 mg, about 20 mg, or about 40 mg of pregnenolone.

(89) The composition of any one of (78)-(88), further comprising a pharmaceutically acceptable excipient.

(90) A method of increasing testosterone levels in a subject in need thereof, comprising administering to the subject:

i) a first composition comprising about 1 mg to about 50 mg of a selective estrogen receptor modulator; and ii) a second composition comprising about 100 mg to about 800 mg testosterone in a form suitable for oral administration.

(91) The method of (90), wherein the subject is a human subject and administering the first and second compositions increases the subject's total testosterone level by about 100% compared to the subject's baseline total testosterone level.

(92) The method of (90) or (91), wherein the subject is a human subject and administering the first and second compositions maintains the subject's LH level at about 1 IU/L or more.

(93) The method of any one of (90)-(92), wherein the subject is a human subject and administering the first and second compositions maintains the subject's FSH level at about 1 IU/L or more.

(94) The method of any one of (90)-(93), wherein the selective estrogen receptor modulator is selected from the group consisting of clomiphene, enclomiphene, tamoxifen, toremifene, acolbifene, lasoxifene, bazedoxifene, droloxifene, raloxifene, metabolites thereof, and pharmaceutically acceptable salts or solvates thereof.

(95) The method of any one of (90)-(94), wherein the selective estrogen receptor modulator is enclomiphene or a pharmaceutically acceptable salt thereof.

(96) The method of (94) or (95), wherein the pharmaceutically acceptable salt of enclomiphene is enclomiphene citrate.

(97) The method of any one of (90)-(96), wherein the first composition comprises about 3 mg, about 3.125 mg, about 6.25 mg, about 12.5 mg, about 25 mg, or about 50 mg of the selective estrogen receptor modulator.

(98) The method of any one of (90)-(97), wherein the second composition comprises about 200 mg, about 400 mg, about 600 mg, or about 800 mg of testosterone.

(99) The method of any one of (90)-(98), wherein the first composition further comprises a neurosteroid.

(100) The method of (99), wherein the neurosteroid is pregnenolone.

(101) The method of (100), wherein the first composition comprises about 5 mg to about 40 mg of pregnenolone.

(102) The method of (100) or (101), wherein the first composition comprises about 5 mg, about 10 mg, about 20 mg, or about 40 mg of pregnenolone.

(103) The method of any one of (90)-(102), wherein the first composition is in the form of a sublingual tablet.

(104) The method of any one of (90)-(103), wherein the second composition comprising testosterone in a form suitable for oral administration is a tablet or capsule.

(105) The method of any one of (90)-(104), wherein the first composition is administered sublingually.

(106) The method of any one of (90)-(105), wherein the second composition is administered orally.

(107) The method of any one of (90)-(106), further comprising administering about 0.1 mg to about 5 mg of dutasteride.

(108) A method of increasing testosterone levels in a subject in need thereof, comprising administering to the subject:

i) a first composition in a form suitable for sublingual administration comprising:
a) about 1 mg to about 50 mg of enclomiphene citrate;
b) cellulose;
c) a non-nutritive sweetener;
d) a flavoring agent; and
e) magnesium stearate; and ii) at least one second composition in a form suitable for oral administration and lymphatic absorption comprising:
a) about 200 mg of native testosterone;
b) safflower oil;
c) cellulose; and
d) magnesium stearate.

(109) The method of (108), wherein the subject is a human subject and administering the first and second compositions increases the subject's total testosterone level by about 100% compared to the subject's baseline total testosterone level.

(110) The method of (108) or (109), wherein the subject is a human subject and administering the combination maintains the subject's LH level at about 1 IU/L or more.

(111) The method of any one of (108)-(110), wherein the subject is a human subject and administering the combination maintains the subject's FSH level at about 1 IU/L or more.

(112) The method of any one of (108)-(111), wherein the first composition comprises about 3 mg, about 3.125 mg, about 6.25 mg, about 12.5 mg, about 25 mg, or about 50 mg of the enclomiphene citrate.

(113) The method of any one of (108)-(112), wherein the second composition comprises about 200 mg, about 400 mg, about 600 mg, or about 800 mg of native testosterone.

(114) The method of any one of (108)-(113), wherein the first composition further comprises a neurosteroid.

(115) The method of (114), wherein the neurosteroid is pregnenolone.

(116) The method of (115), wherein the first composition comprises about 5 mg to about 40 mg of pregnenolone.

(117) The method of (115) or (116), wherein the first composition comprises about 5 mg, about 10 mg, about 20 mg, or about 40 mg of pregnenolone.

(118) The method of any one of (108)-(117), wherein the first composition is in the form of a sublingual tablet.

(119) The method of any one of (108)-(118), wherein the second composition comprising native testosterone in a form suitable for oral administration and lymphatic absorption is a tablet or capsule.

(120) The method of any one of (108)-(119), wherein the first composition is administered sublingually.

(121) The method of any one of (108)-(120), wherein the second composition is administered orally.

(122) The method of any one of (108)-(121), further comprising administering about 0.1 mg to about 5 mg of dutasteride.

(123) A method of increasing testosterone levels in a subject in need thereof, comprising:

i) administering to the subject an oral or sublingual tablet or capsule comprising about 5 mg to about 80 mg of enclomiphene citrate, clomiphene citrate, or toremifene citrate; and ii) topically administering to the subject about 50 mg to about 400 mg of testosterone base or testosterone ester, wherein administering the oral or sublingual tablet or capsule and topically administering testosterone base or testosterone ester at least maintains a subject's baseline LH level and FSH level at about 1 IU/L or more, or increases a subject's LH level and FSH level to about 1 IU/L or more.

(124) The method of (123), wherein the oral or sublingual tablet or capsule is a sublingual tablet.

(125) The method of (123), wherein the oral or sublingual tablet or capsule comprises enclomiphene citrate.

(126) The method of (125), wherein the oral or sublingual tablet or capsule comprises about 5 mg to about 80 mg of enclomiphene citrate.

(127) The method of (126), wherein the oral or sublingual tablet or capsule comprises about 6.25 mg, about 12.5 mg, about 25 mg, or about 50 mg of the enclomiphene citrate.

(128) The method of (123), wherein the oral or sublingual tablet or capsule comprises clomiphene citrate.

(129) The method of (128), wherein the oral or sublingual tablet or capsule comprises about 5 mg to about 80 mg of clomiphene citrate.

(130) The method of (123), wherein the oral or sublingual tablet or capsule comprises toremifene citrate.

(131) The method of (130), wherein the oral or sublingual tablet or capsule comprises about 5 mg to about 120 mg of toremifene citrate.

(132) The method of (123), wherein the subject is topically administered about 50 mg to about 200 mg of testosterone base or testosterone ester.

(133) The method of (123), wherein the oral or sublingual tablet or capsule further comprises a neurosteroid.

(134) The method of (133), wherein the neurosteroid is pregnenolone.

(135) The method of (133), wherein the oral or sublingual tablet or capsule comprises about 1 mg to about 40 mg of pregnenolone.

(136) The method of (123), wherein the oral or sublingual tablet or capsule further comprises cellulose, a non-nutritive sweetener, a flavoring agent, and magnesium stearate.

(137) The method of (123), wherein the subject is a human subject and administering the oral or sublingual tablet or capsule and topically administering testosterone base or testosterone ester increases the subject's total testosterone level by at least about 50% compared to the subject's baseline total testosterone level.

(138) A method of increasing testosterone levels in a subject in need thereof, comprising administering to the subject:

i) about 5 mg to about 250 mg of enclomiphene citrate, clomiphene citrate, or toremifene citrate; and ii) about 50 mg to about 400 mg of testosterone base or testosterone ester, wherein at least the testosterone base or testosterone ester is administered topically or transdermally, wherein administering enclomiphene citrate, clomiphene citrate, or toremifene citrate and testosterone base or testosterone ester maintains a subject's LH level and FSH level at about 1 IU/L or more, or increases a subject's LH level and FSH level to about 1 IU/L or more.

(139) The method of (138), wherein the subject is topically administered testosterone base or testosterone ester.

(140) The method of (139), wherein the subject is topically administered about 50 mg to about 400 mg of testosterone base or testosterone ester daily.

(141) The method of (140), wherein the subject is topically administered about 50 mg to about 200 mg of testosterone base or testosterone ester daily.

(142) The method of (138), wherein the subject is topically administered enclomiphene citrate.

(143) The method of (142), wherein the subject is topically administered about 5 mg to about 150 mg per day of enclomiphene citrate.

(144) The method of (138), wherein the subject is topically administered clomiphene citrate.

(145) The method of (144), wherein the subject is topically administered about 5 mg to about 150 mg per day of clomiphene citrate.

(146) The method of (139), wherein the subject is topically administered toremifene citrate.

(147) The method of (146), wherein the subject is topically administered about 5 mg to about 240 mg per day of toremifene citrate.

(148) The method of (138), wherein the enclomiphene citrate, clomiphene citrate, or toremifene citrate is administered orally or sublingually.

(149) The method of (138), wherein the subject is transdermally administered testosterone base or testosterone ester.

(150) The method of (149), wherein the subject is transdermally administered enclomiphene citrate, clomiphene citrate, or toremifene citrate.

(151) The method of (150), wherein the subject is transdermally administered enclomiphene citrate.

(152) The method of (138), wherein the enclomiphene citrate, clomiphene citrate, or toremifene citrate is administered as a first topical or transdermal composition and the testosterone is administered as a second topical or transdermal composition.

(153) The method of (138), wherein the enclomiphene citrate, clomiphene citrate, or toremifene citrate and the testosterone is administered as a topical or transdermal composition.

(154) The method of (138), wherein the enclomiphene citrate, clomiphene citrate, or toremifene citrate and the testosterone are administered by a transdermal patch.

(155) The method of (138), wherein the subject is a human subject and administering the therapeutically effective amount of enclomiphene citrate, clomiphene citrate, or toremifene citrate and the therapeutically effective amount of testosterone base or testosterone ester increases the subject's total testosterone level by at least about 50% compared to the subject's baseline total testosterone level.

EXAMPLES

These examples are provided for the purpose of illustration only and the embodiments described herein should in no way be construed as being limited to these examples. Rather, the embodiments should be construed to encompass any and all variations which become evident as a result of the teaching provided herein.

Example 1: Baseline Test

This example investigated the anti-suppressive properties of a SERM (enclomiphene) after administration of testosterone and enclomiphene.

Baseline hormone levels without any pharmacological intervention were measured to determine if testosterone, LH and FSH levels were maintained after the administration of testosterone and enclomiphene (see Table 1, n=1). Calculated free testosterone levels were 114 pg/mL.

TABLE 1

| Baseline hormone levels | | |
|---|---|---|
| | Result/Status | Cutoff/Expected Values |
| Endocrinology | | |
| Testosterone, Total | 460.00 | 249.0-836.0 ng/dL |
| Serology | | |
| Estradiol | 33.9 | 11.3-43.0 pg/mL |
| LH | 5.6 | 1.7-8.6 mIU/mL |
| Prolactin | 10.9 | 4.0-15.0 ng/mL |
| Cortisol | 17.50 | |
| Morning | 6.02-18.40 ug/dL | |
| Afternoon: | 2.68-10.50 ug/dL | |
| SHBG | 23.8 | 16.5-56.0 nmol/L |
| FSH | 6.6 | |
| Adult Male: | 1.5-12.4 mIU/mL | |

Example 2: Pre-TRT with 6.25 mg of Enclomiphene and 5 mg of LGD-4033

This example investigated the effects of co-administration of a SERM (enclomiphene) and a selective androgen receptor modulator (SARM) (LGD-4033) on endogenous testosterone, LH, and FSH production. LGD-4033 acted as an anabolic-androgenic steroid and suppressed the production of LH/FSH/testosterone.

Hormone levels were measured after co-administration of 6.25 mg of enclomiphene and 5 mg of LGD-4033. Total testosterone and LH levels remained at or above baseline levels while free testosterone and FSH levels remained elevated over the course of three subsequent tests (see Table 2, n=1).

TABLE 2

| Hormone levels after 6.25 mg of enclomiphene + 5 mg of LGD-4033 | |
|---|---|
| Total Testosterone: | 437/594/641 ng/dl |
| Free Testosterone: | 141.7/147.9/149 pg/mL |
| Estradiol: | 21/32/24 p g/mL |
| LH: | 5.7/5.7 IU/L |
| FSH: | 8.4/9.3 IU/L |
| SHBG: | 7/10/15 nmol/L |

Example 3: Pre-TRT Experiment with 6.25 mg of Enclomiphene

This example investigated the effects of administering a SERM (enclomiphene) on endogenous testosterone, LH, and FSH production.

Hormone levels were measured after administration of 6.25 mg of enclomiphene (see Table 3, n=1). Calculated free testosterone levels were 197 pg/mL, a significant elevation from baseline (114 pg/mL, a 73% increase).

TABLE 3

| Hormone levels after 6.25 mg of enclomiphene | | | | |
|---|---|---|---|---|
| Test Name | In Range | Out of Range | Reference Range | Lab |
| Testosterone, Free, Bioavailable and Total, MS | | | | |
| Albumin | 4.6 | | 3.6-5.1 g/dL | SLI |
| Sex Hormone Binding Globulin | 20 | | 10-50 nmol/L | SLI |
| Testosterone, Free and Bioavailable | | | | |
| Testosterone, Bioavailable | | | | |
| Testosterone, Free | 153.7 | | 46.0-224.0 pg/mL | |
| Testosterone, Bioavailable | 322.9 | | 110.0-575.0 ng/dL | |
| Testosterone, Total, MS | 724 | | 250-1100 ng/dL | SLI |

Example 4: TRT with 200 mg of Testosterone and 6.25 mg of Enclomiphene after 30 Days (+4 and +12 Hours)

This example investigated the anti-suppressive properties of a SERM (enclomiphene) after administration of testosterone and enclomiphene.

Hormone levels were measured after co-administration of 200 mg of testosterone and 6.25 mg of enclomiphene for 30 days. Testosterone concentration was measured at +4 hours and +12 hours after administration. Testosterone peaks between 3-5 hours and is generally out of the system within 12 hours (with acute suppression from baseline), as seen in FIG. 1. Testosterone concentration was measured at +4 hours after administration to capture the peak testosterone concentration ($c_{Max}$) and +12 hours after administration to capture the trough testosterone concentration ($c_{Min}$) to determine if endogenous testosterone suppression is prevented with the enclomiphene. Results (see Tables 4 and 5, n=1) showed a strong elevation in testosterone concentration at $c_{Max}$ (total testosterone: 1500+, free testosterone: 505+), while LH and FSH were elevated above baseline (11 and 9.8). Even after the exogenous testosterone was out of the system ($c_{Min}$), total testosterone (565) and free testosterone (164) remained elevated. Even after the exogenous testosterone was out of the system ($c_{Min}$), exogenous testosterone was not suppressed as testosterone data alone predicted.

TABLE 4

| Hormone levels at +4 hours after 200 mg of testosterone + 6.25 mg of enclomiphene | | |
|---|---|---|
| | Result/Status | Cutoff/Expected Values |
| Endocrinology | | |
| Testosterone, Total | 1500.0 High | 249.0-836.0 ng/dL |
| Serology | | |
| Estradiol | 35.5 | 11.3-43.0 pg/mL |
| LH | 11.0 High | 1.7-8.6 mIU/mL |
| Prolactin | 3.8 Low | 4.0-15.0 ng/ml |
| Cortisol | 12.80 | |
| Morning | 6.02-18.40 ug/dL | |
| Afternoon: | 2.68-10.50 ug/dL | |
| SHBG | 17.5 | 16.5-56.0 nmol/L |
| FSH | 9.8 | |
| Adult Male: | 1.5-12.4 mIU/mL | |

TABLE 5

| Hormone levels at +12 hours after 200 mg of testosterone + 6.25 mg of enclomiphene | | |
|---|---|---|
| | Result/Status | Cutoff/ Expected Values |
| Endocrinology | | |
| Testosterone, Total | 556.0 | 249.0-836.0 ng/dL |
| Serology | | |
| Estradiol | 34.5 | 11.3-43.0 pg/mL |
| LH | 12.7 High | 1.7-8.6 mIU/mL |
| Prolactin | 19.8 High | 4.0-15.0 ng/mL |
| Cortisol | 16.10 | |
| Morning | 6.02-18.40 ug/dL | |
| Afternoon: | 2.68-10.50 ug/dL | |
| SHBG | 17.5 | 16.5-56.0 nmol/L |
| FSH | 9.7 | |
| Adult Male: | 1.5-12.4 mIU/mL | |

Example 5: TRT with 200 mg of Testosterone BID+6.25 mg of Enclomiphene (+7.5 and +16 Hours)

This example investigated the anti-suppressive properties of a SERM (enclomiphene) after administration of testosterone and enclomiphene. This example also investigated whether a higher dosage of testosterone affected the anti-suppressive properties of enclomiphene.

Hormone levels were measured after co-administration of 200 mg of testosterone twice a day (BID) (200 mg at 8 AM and 200 mg at 4 PM) and 6.25 mg of enclomiphene. Testosterone concentration was measured at +7.5 hours, outside of the 3-5 hour peak window for testosterone, which resulted in lower testosterone levels than those seen in Example 4, despite the higher dosage (see Table 6, n=1). Testosterone concentration was also measured at +16 hours to see longer-term effects. Testosterone, LH, and FSH levels remained elevated above baseline, despite doubling the testosterone dosage, showing continued success at preventing suppression (see Table 7, n=1).

TABLE 6

| Hormone levels at +7.5 hours after 200 mg of testosterone BID + 6.25 mg of enclomiphene | | |
|---|---|---|
| | Result/ Status | Cutoff/ Expected Values |
| Endocrinology | | |
| Testosterone, Total | 663.0 | 249.0-836.0 ng/dL |
| Serology | | |
| Estradiol | 24.5 | 11.3-43.0 pg/mL |
| LH | 11.2 High | 1.7-8.6 mIU/mL |
| Prolactin | 9.4 | 4.0-15.0 ng/mL |
| SHBG | 18.0 | 16.5-56.0 mmol/L |
| DHEA-S | 539.0 High | 89.0-492.0 ug/dL |
| FSH | 8.4 | |

TABLE 7

| Hormone levels at +16 hours after 200 mg of testosterone BID + 6.25 mg of enclomiphene | | |
|---|---|---|
| | Result/Status | Cutoff/ Expected Values |
| Endocrinology | | |
| Testosterone, Total | 716.0 | 249.0-836.0 ng/dL |
| Serology | | |
| Estradiol | 31.7 | 11.3-43.0 pg/mL |
| LH | 14.1 High | 1.7-8.6 mIU/mL |
| Prolactin | 16.9 High | 4.0-15.0 ng/mL |
| Cortisol | 25.00 | |
| Morning | 6.02-18.40 ug/dL | |
| Afternoon: | 2.68-10.50 ug/dL | |
| SHBG | 18.1 | 16.5-56.0 nmol/L |
| FSH | 9.7 | |
| Adult Male: | 1.5-12.4 mIU/mL | |

Example 6: TRT with 200 mg of Testosterone BID+3.125 mg of Enclomiphene (+4 and +20 Hours)

This example investigated the anti-suppressive properties of a SERM (enclomiphene) after administration of testosterone and enclomiphene. This example also investigated whether a lower dosage of enclomiphene affected its anti-suppressive properties.

Hormone levels were measured after co-administration of 200 mg of testosterone (BID) and 3.125 mg of enclomiphene. Testosterone concentration was measured at +4 and +20 hours. Testosterone, LH, and ESH levels remained slightly above baseline, but not as high as on the 6.25 mg dosage (see Tables 8 and 9, n=1).

TABLE 8

| Hormone levels at +4 hours after 200 mg of testosterone BID + 3.125 mg of enclomiphene | | |
|---|---|---|
| | Result/Status | Cutoff/ Expected Values |
| Endocrinology | | |
| Testosterone, Total | 1381.0 High | 249.0-836.0 ng/dL |
| Serology | | |
| Estradiol | 31.7 | 11.3-43.0 pg/mL |
| LH | 7.8 | 1.7-8.6 mIU/mL |
| Prolactin | 5.4 | 4.0-15.0 ng/mL |
| Cortisol | 10.50 | |
| Morning | 6.02-18.40 ug/dL | |
| Afternoon: | 2.68-10.50 ug/dL | |
| SHBG | 17.7 | 16.5-56.0 nmol/L |
| FSH | 7.4 | |
| Adult Male: | 1.5-12.4 mIU/mL | |

TABLE 9

| Hormone levels at +20 hours after 200 mg of testosterone BID + 3.125 mg of enclomiphene | | |
|---|---|---|
| | Result/Status | Cutoff/ Expected Values |
| Endocrinology | | |
| Testosterone, Total | 531.0 | 249.0-836.0 ng/dL |
| Serology | | |
| Estradiol | 45.2 High | 11.3-43.0 pg/mL |
| LH | 9.5 High | 1.7-8.6 mIU/mL |
| Prolactin | 22.4 High | 4.0-15.0 ng/mL |
| SHBG | 19.3 | 16.5-56.0 mmol/L |
| DHEA-S | 508.0 High | 89.0-492.0 ug/dL |
| FSH | 7.9 | |
| Adult Male: | 1.5-12.4 mIU/mL | |

Example 7: TRT with 200 mg of Testosterone BID+10 mg of Toremifene (+4 and +20 Hours)

This example investigated the anti-suppressive properties of a SERM (toremifene) after administration of testosterone and toremifene.

Enclomiphene was replaced by toremifene to determine whether SERMs can prevent TRT-related suppression. Toremifene is less potent mg per mg, so triple the dosage was used. Hormone levels were measured after co-administration of 200 mg of testosterone (BID) and 10 mg of toremifene. Testosterone concentration was measured at +4 and +20 hours. The +4 hour test had an insufficient quantity of blood, so only testosterone was tested. The +20 hour test showed that testosterone, LH, and FSH was still maintained above baseline (see Tables 10 and 11, n=1).

TABLE 10

| Hormone levels at +4 hours after 200 mg of testosterone BID + 10 mg of toremifene | | |
|---|---|---|
| | Result/Status | Cutoff/ Expected Values |
| Endocrinology | | |
| Testosterone, Total | 1500.0 High | 249.0-836.0 ng/dL |
| Serology | | |
| Estradiol | — QNS | 11.3-43.0 pg/mL |
| LH | — QNS | 1.7-8.6 mIU/mL |
| Prolactin | — QNS | 4.0-15.0 ng/mL |
| Cortisol | — QNS | |
| Morning | 6.02-18.40 ug/dL | |
| Afternoon: | 2.68-10.50 ug/dL | |
| SHBG | — QNS | 16.5-56.0 nmol/L |
| FSH | — QNS | |
| Adult Male: | 1.5-12.4 mIU/mL | |

TABLE 11

| Hormone levels at +20 hours after 200 mg of testosterone BID + 10 mg of toremifene | | |
|---|---|---|
| | Result/Status | Cutoff/ Expected Values |
| Endocrinology | | |
| Testosterone, Total | 502.0 | 249.0-836.0 ng/dL |
| Serology | | |
| Estradiol | 31.3 | 11.3-43.0 pg/mL |
| LH | 7.7 | 1.7-8.6 mIU/mL |
| Prolactin | 14.4 | 4.0-15.0 ng/mL |
| Cortisol | 17.30 | |
| Morning | 6.02-18.40 ug/dL | |
| Afternoon: | 2.68-10.50 ug/dL | |
| SHBG | 14.9 Low | 16.5-56.0 nmol/L |
| FSH | 8.0 | |

Example 8: TRT with 400 mg of Testosterone BID+10 mg of Toremifene (+4 and +18 Hours)

This example investigated the anti-suppressive properties of a SERM (toremifene) after administration of testosterone and toremifene. This example also investigated whether a higher dosage of testosterone affected the anti-suppressive properties of toremifene.

Hormone levels were measured after co-administration of 400 mg of testosterone (BID) (400 mg at 8 AM and 400 mg at 4 PM) and 10 mg of toremifene. Testosterone concentration was measured at +4 and +18 hours. Testosterone, LH, and FSH levels remained stable although the +18 hour levels were slightly suppressed due to sleep deprivation (4 hours of sleep prior to the test) and not pharmacology (see Tables 12 and 13, n=1). No endogenous testosterone suppression occurred after 3 months of consecutive TRT administration, suggesting an effective long-term treatment.

TABLE 12

| Hormone levels at +4 hours after 400 mg of testosterone BID + 10 mg of toremifene | | |
|---|---|---|
| | Result/Status | Cutoff/ Expected Values |
| Endocrinology | | |
| Testosterone, Total | 1329.0 High | 249.0-836.0 ng/dL |
| Serology | | |
| Estradiol | 19.3 | 11.3-43.0 pg/mL |
| LH | 9.1 High | 1.7-8.6 mIU/mL |
| Prolactin | 6.8 | 4.0-15.0 ng/mL |
| Cortisol | 11.0 | |
| Morning | 6.02-18.40 ug/dL | |
| Afternoon: | 2.68-10.50 ug/dL | |
| SHBG | 13.9 Low | 16.5-56.0 nmol/L |
| FSH | 5.7 | |
| Adult Male: | 1.5-12.4 mIU/mL | |

TABLE 13

| Hormone levels at +18 hours after 400 mg of testosterone BID + 10 mgof toremifene | | |
|---|---|---|
| | Result/Status | Cutoff/ Expected Values |
| Endocrinology | | |
| Testosterone, Total | 374.0 | 249.0-836.0 ng/dL |
| Serology | | |
| Estradiol | <15.0 | 11.3-43.0 pg/mL |
| LH | 3.9 | 1.7-8.6 mIU/mL |
| Prolactin | 5.3 | 4.0-15.0 ng/mL |
| Cortisol | 14.00 | |
| Morning | 6.02-18.40 ug/dL | |
| Afternoon: | 2.68-10.50 ug/dL | |
| SHBG | 14.0 Low | 16.5-56.0 nmol/L |
| FSH | 5.0 | |
| Adult Male: | 1.5-12.4 mIU/mL | |

Example 9: Hormone Levels Once TRT with 200 mg of Testosterone BID+10 mg of Toremifene Cycle Concluded This example investigated whether endogenous hormone levels would return to baseline levels upon conclusion of a 2 month cycle.

Hormone levels were measured after the 2 month cycle of testosterone (BID) and 10 mg of toremifene concluded. No testosterone suppression occurred after cycle conclusion of testosterone and toremifene. Total and free testosterone levels were normal/slightly above baseline since toremifene has a longer half-life, so it was not completely out of the system (see Table 14, n=1).

TABLE 14

| Hormone levels after TRT with 200 mg of testosterone BID + 10 mg of toremifene (cycle conclusion) | | | |
|---|---|---|---|
| Test Name | Result | Reference Range | Lab |
| Testosterone, Free, Bioavailable and Total, Males (Adult), Immunoassay | | | |
| Testosterone, Total, Males (Adult), 1A | 565 | 250-827 ng/dL | EN |
| Albumin | 4.9 | 3.6-5.1 g/dL | EN |
| Sex Hormone Binding Globulin | 14 | 10-50 nmol/L | EN |
| Testosterone, Free | 136.8 | 46.0-224.0 pg/mL | EN |
| Testosterone, Bioavailable | 305.2 | 110.0-575.0 ng/dL | EN |
| Estradiol, Ultrasensitive, LC/MS | 27 | <OR = 29 pg/mL | EZ |

Example 10: TRT with 200-600 mg Testosterone+30 g Fat+3.125 mg, 6.25 mg, or 12.5 mg Enclomiphene (+4 Hours)

This example investigated the anti-suppressive properties of a SERM (enclomiphene) after administration of oral testosterone, fat, and enclomiphene.

Figure 2:
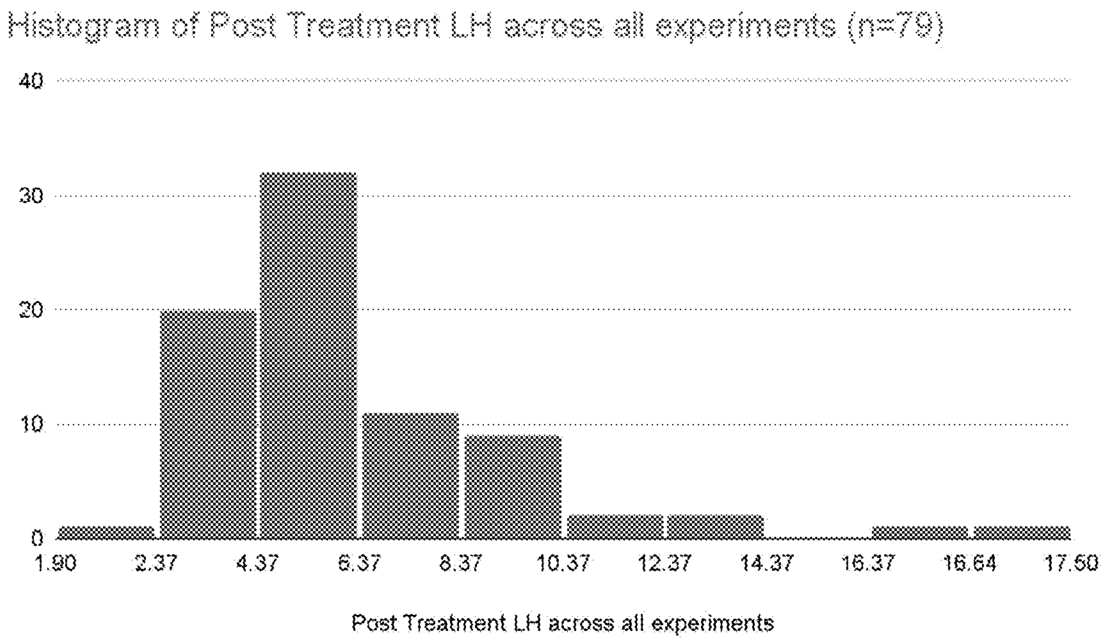
FIG. 2 is a histogram of LH levels after administration of testosterone and enclomiphene.
Figure 3:
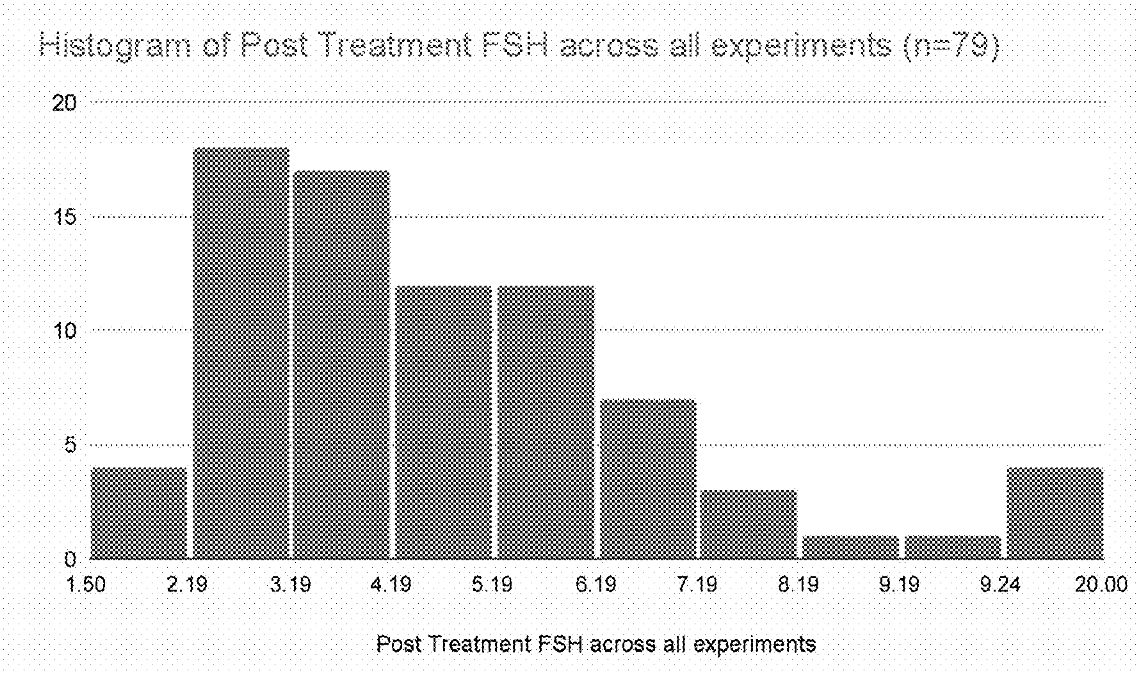
FIG. 3 is a histogram of FSH levels after administration of testosterone and enclomiphene.
Figure 4:
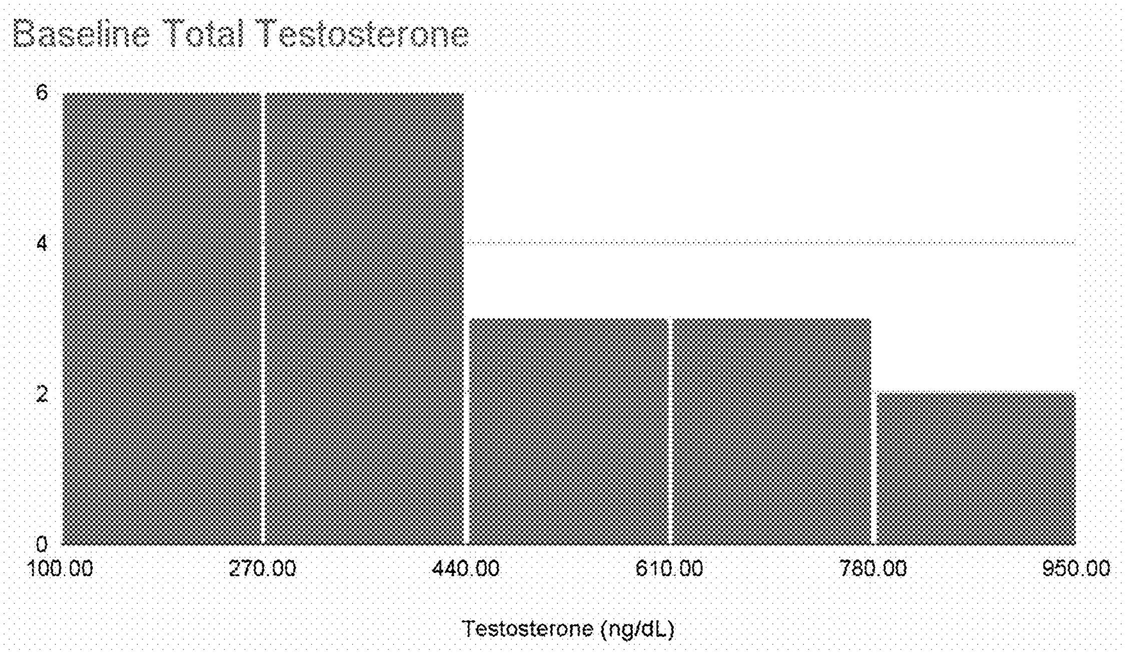
FIG. 4 is a graph of baseline total testosterone levels prior to administration of 200-600 mg testosterone, 30 g fat, and 3.125 mg, 6.25 mg, or 12.5 mg enclomiphene.
Figure 5:
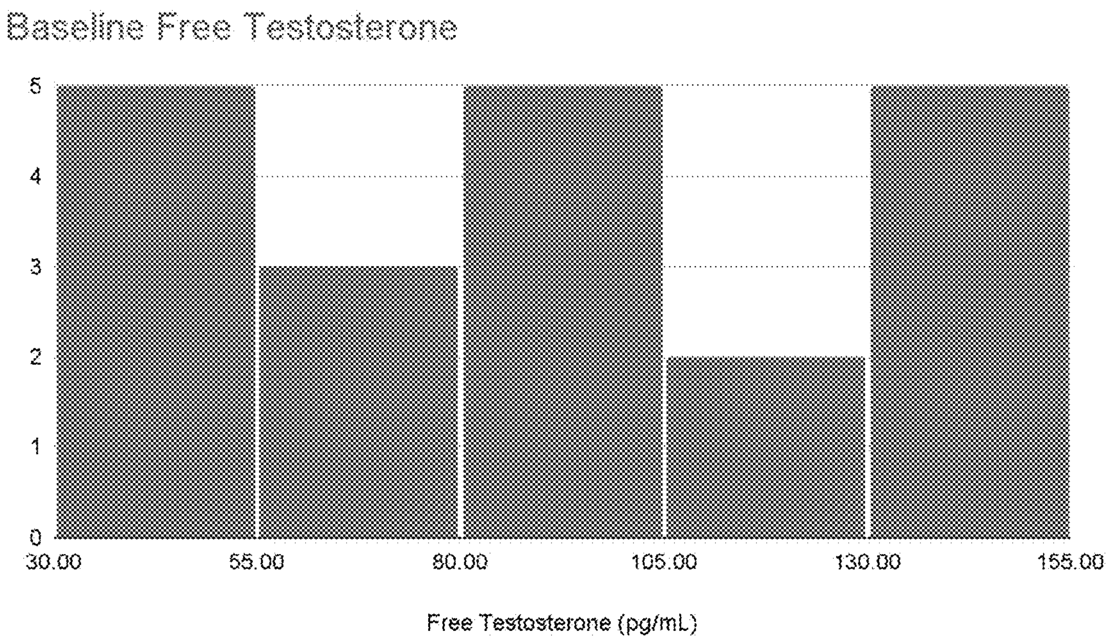
FIG. 5 is a graph of baseline free testosterone levels prior to administration of 200-600 mg testosterone, 30 g fat, and 3.125 mg, 6.25 mg, or 12.5 mg enclomiphene.
Figure 6:
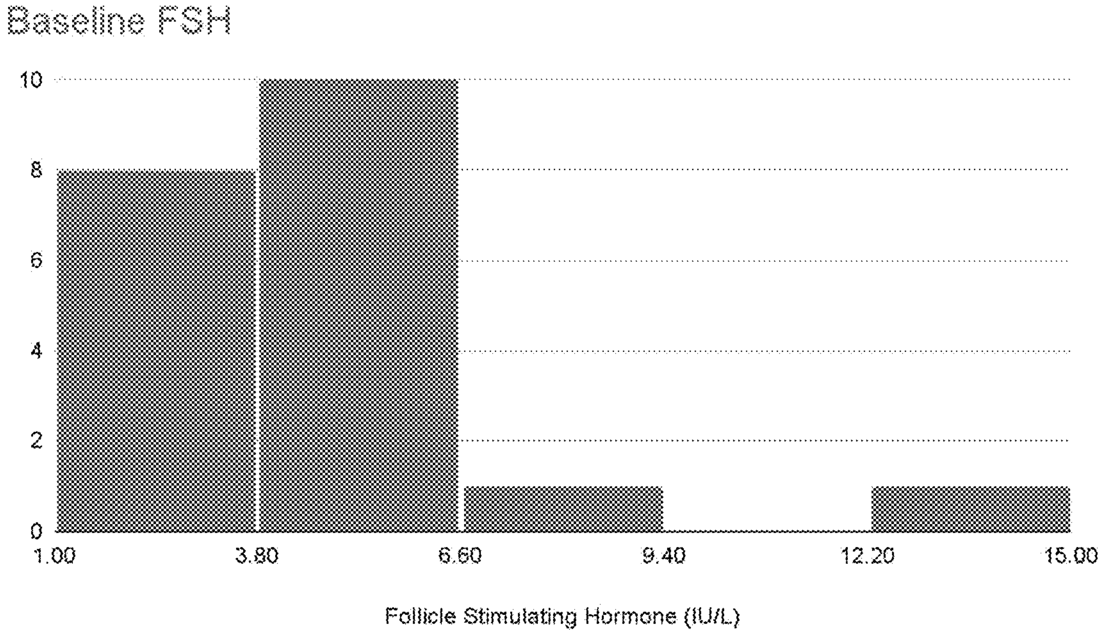
FIG. 6 is a graph of baseline FSH levels prior to administration of 200-600 mg testosterone, 30 g fat, and 3.125 mg, 6.25 mg, or 12.5 mg enclomiphene.
Figure 7:
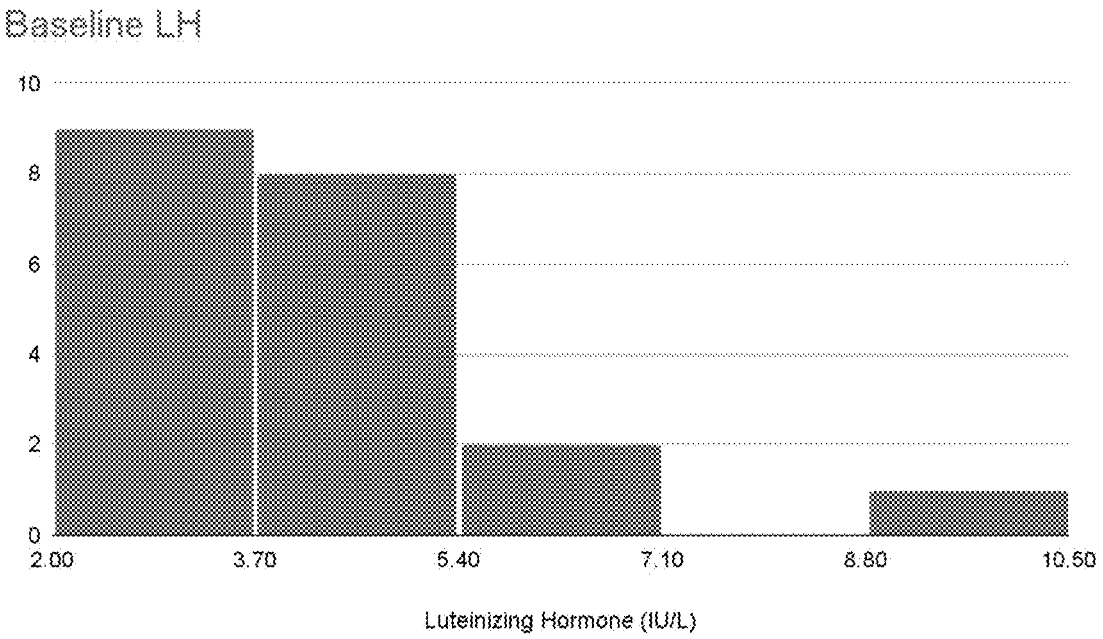
FIG. 7 is a graph of baseline LH levels prior to administration of 200-600 mg testosterone, 30 g fat, and 3.125 mg, 6.25 mg, or 12.5 mg enclomiphene.
Figure 8:
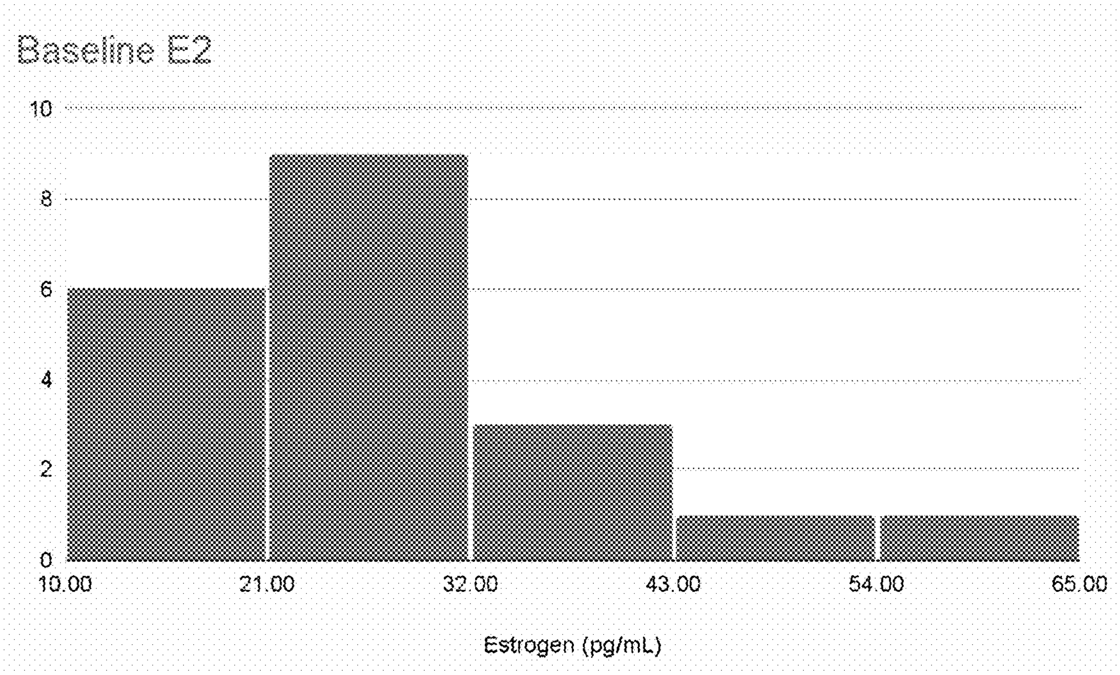
FIG. 8 is a graph of baseline estradiol (E2) levels prior to administration of 200-600 mg testosterone, 30 g fat, and 3.125 mg, 6.25 mg, or 12.5 mg enclomiphene.
Figure 9:
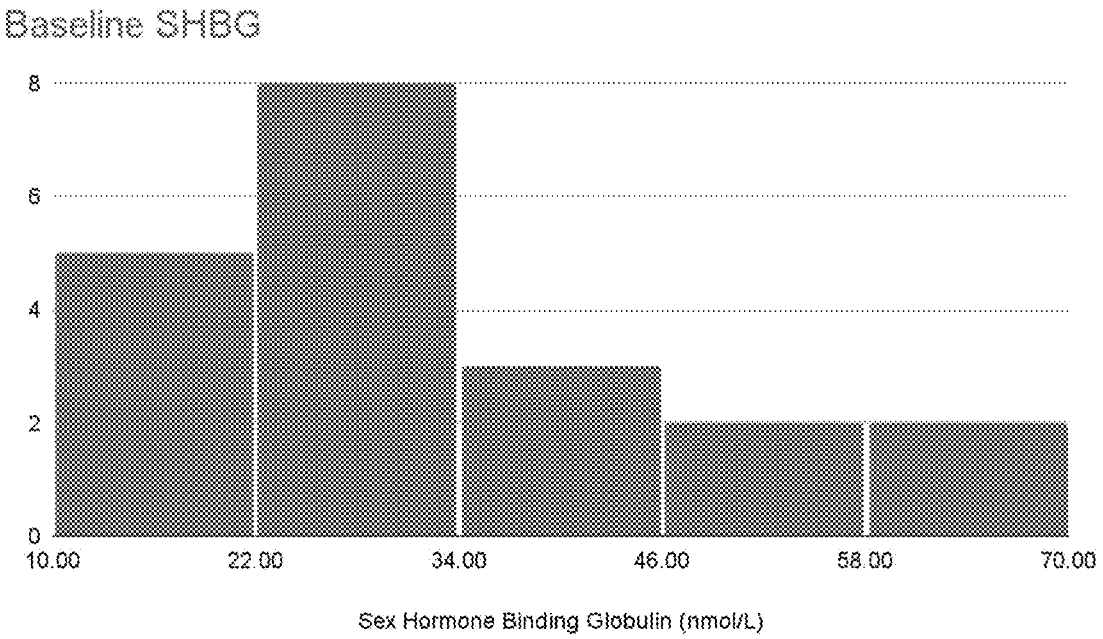
FIG. 9 is a graph of baseline sex hormone-binding globulin (SHBG) levels prior to administration of 200-600 mg testosterone, 30 g fat, and 3.125 mg, 6.25 mg, or 12.5 mg enclomiphene.
Figure 10:
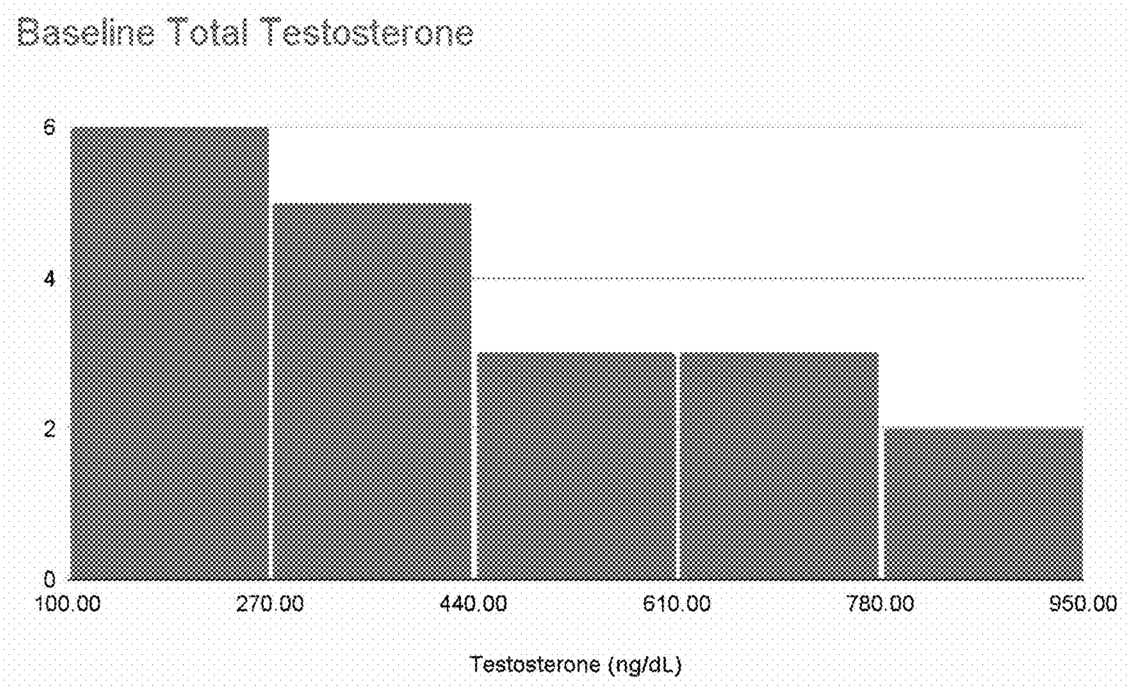
FIG. 10 is a graph of baseline total testosterone levels prior to administration of 800 mg testosterone and 3.125 mg, 6.25 mg, or 12.5 mg enclomiphene.
Figure 11:
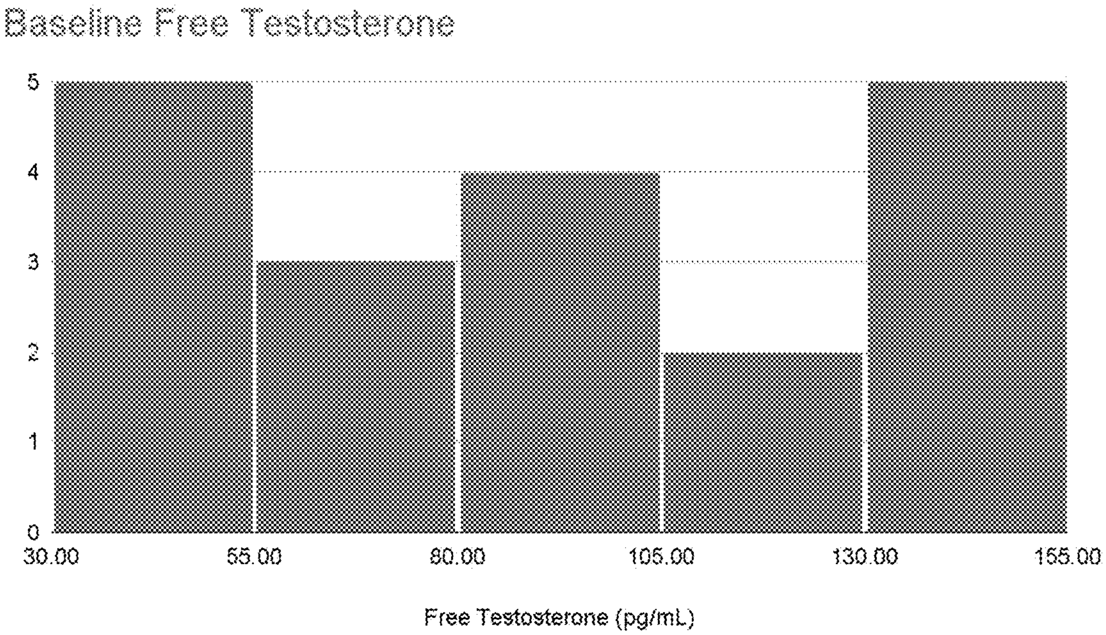
FIG. 11 is a graph of baseline free testosterone levels prior to administration of 800 mg testosterone and 3.125 mg, 6.25 mg, or 12.5 mg enclomiphene.
Figure 12:
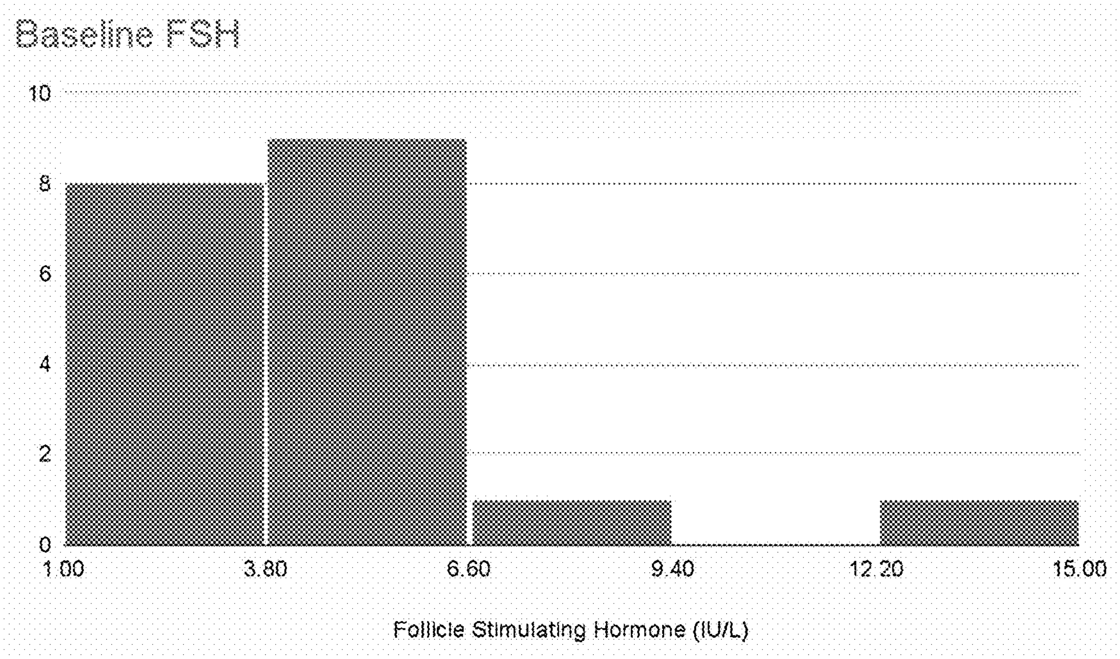
FIG. 12 is a graph of baseline FSH levels prior to administration of 800 mg testosterone and 3.125 mg, 6.25 mg, or 12.5 mg enclomiphene.
Figure 13:
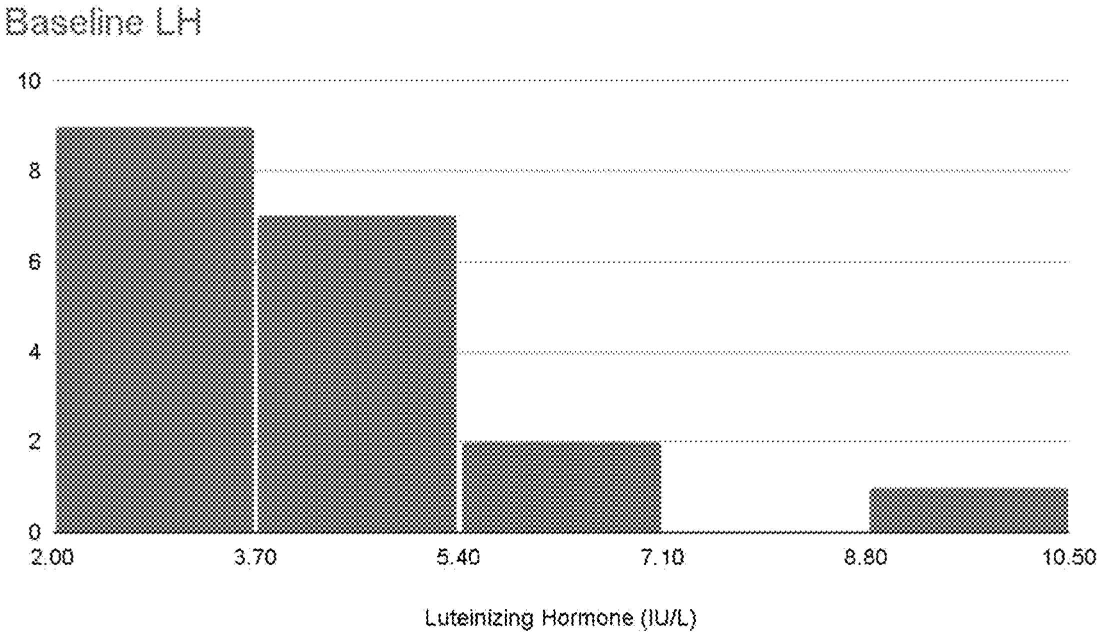
FIG. 13 is a graph of baseline LH levels prior to administration of 800 mg testosterone and 3.125 mg, 6.25 mg, or 12.5 mg enclomiphene.
Figure 14:
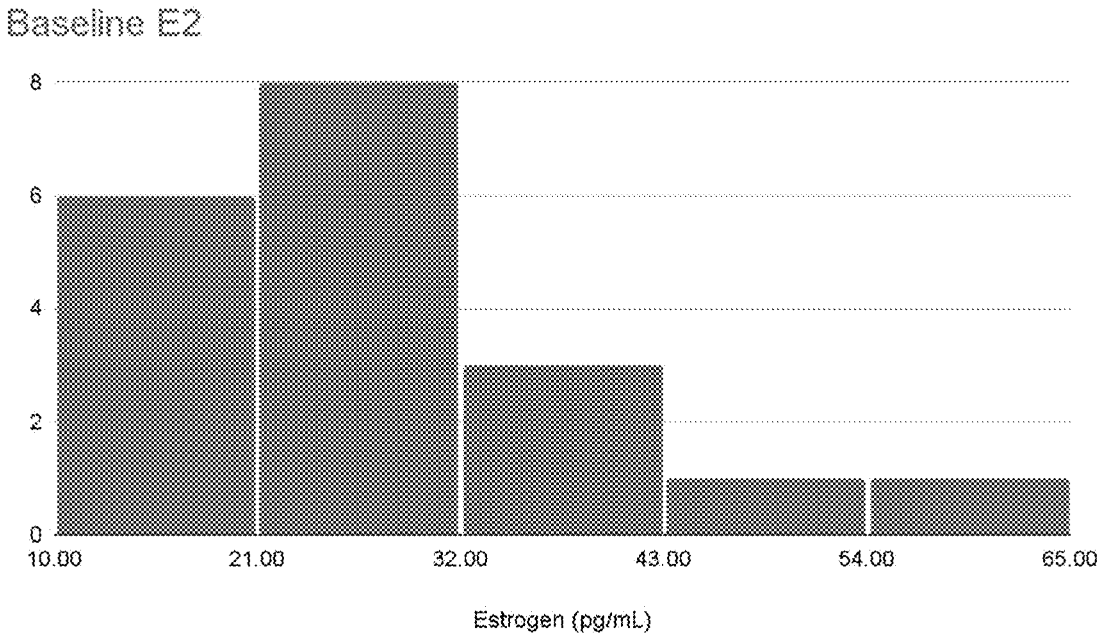
FIG. 14 is a graph of baseline E2 levels prior to administration of 800 mg testosterone and 3.125 mg, 6.25 mg, or 12.5 mg enclomiphene.
Figure 15:
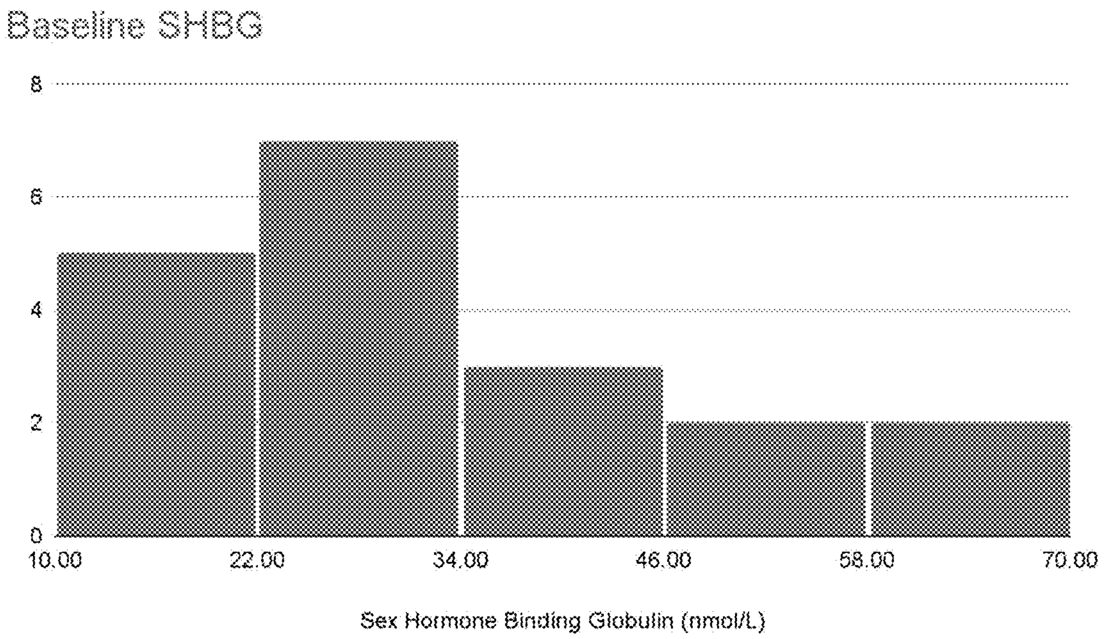
FIG. 15 is a graph of baseline SHBG levels prior to administration of 800 mg testosterone and 3.125 mg, 6.25 mg, or 12.5 mg enclomiphene.
Figure 16:
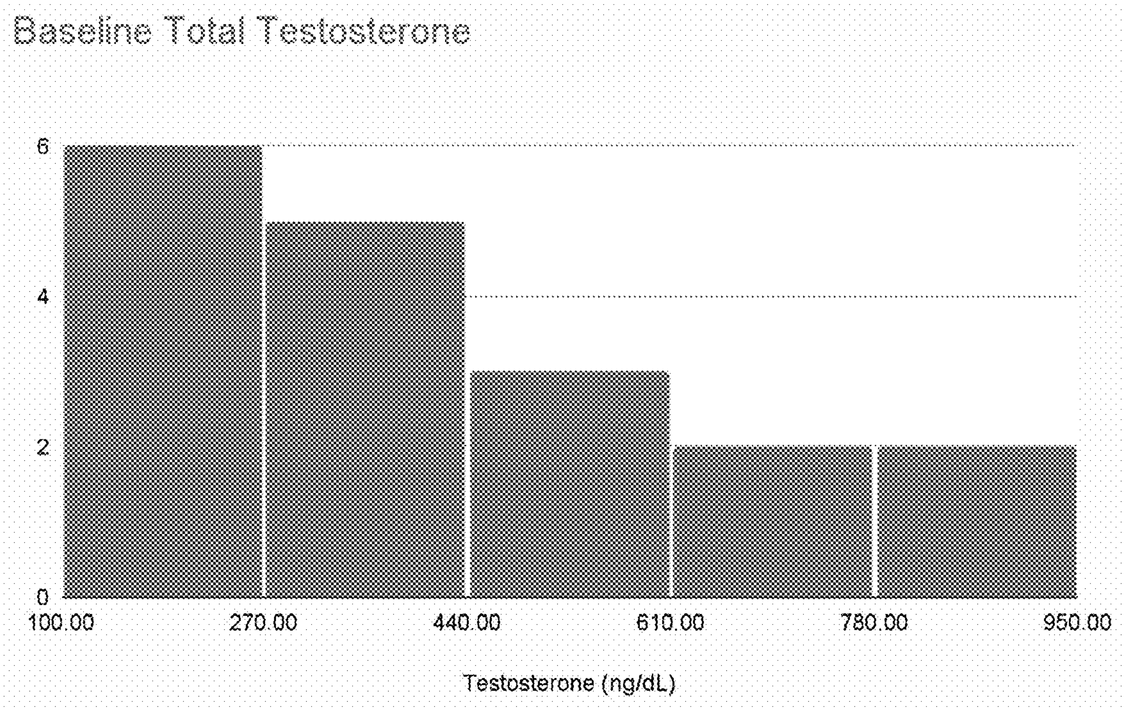
FIG. 16 is a graph of baseline total testosterone levels prior to administration of 800 mg testosterone, 30 g fat, and 3.125 mg, 6.25 mg, or 12.5 mg enclomiphene.
Figure 17:
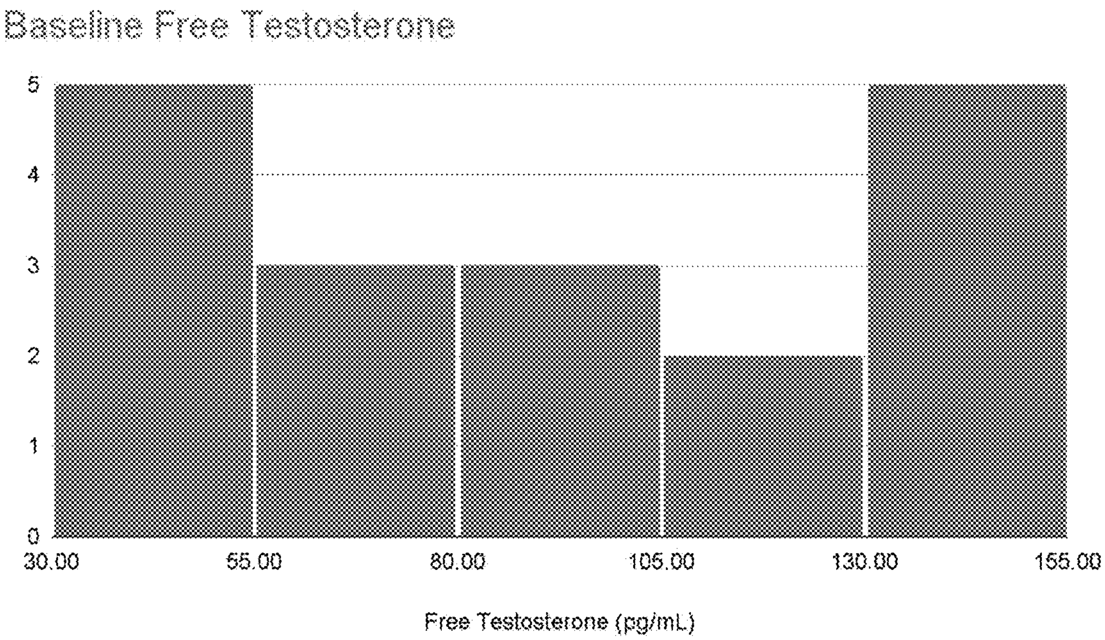
FIG. 17 is a graph of baseline free testosterone levels prior to administration of 800 mg testosterone, 30 g fat, and 3.125 mg, 6.25 mg, or 12.5 mg enclomiphene.
Figure 18:
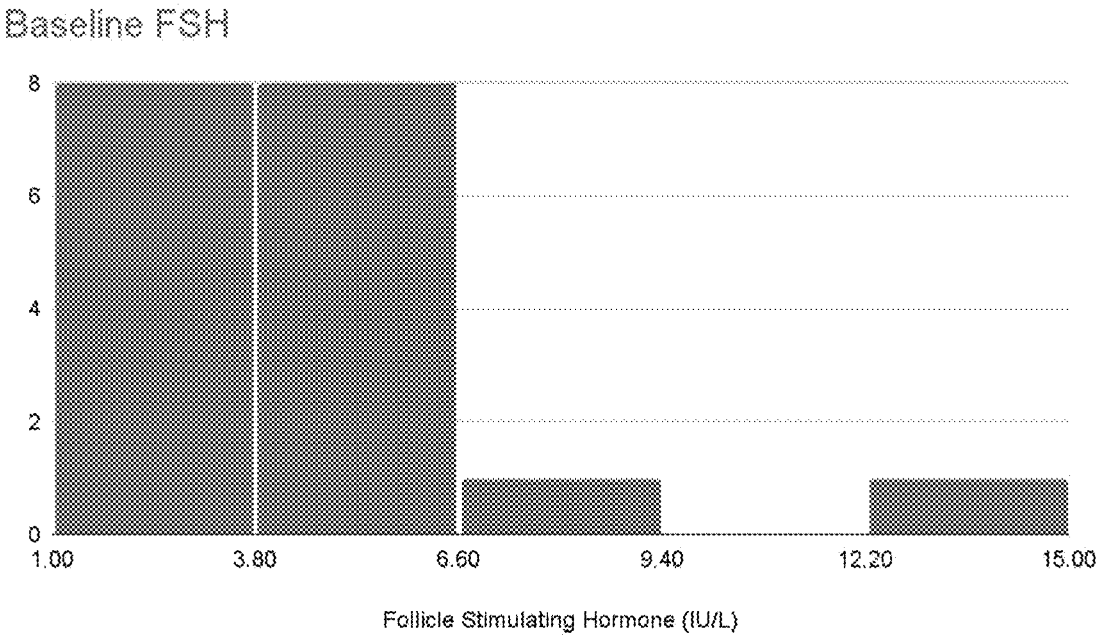
FIG. 18 is a graph of baseline FSH levels prior to administration of 800 mg testosterone, 30 g fat, and 3.125 mg, 6.25 mg, or 12.5 mg enclomiphene.
Figure 19:
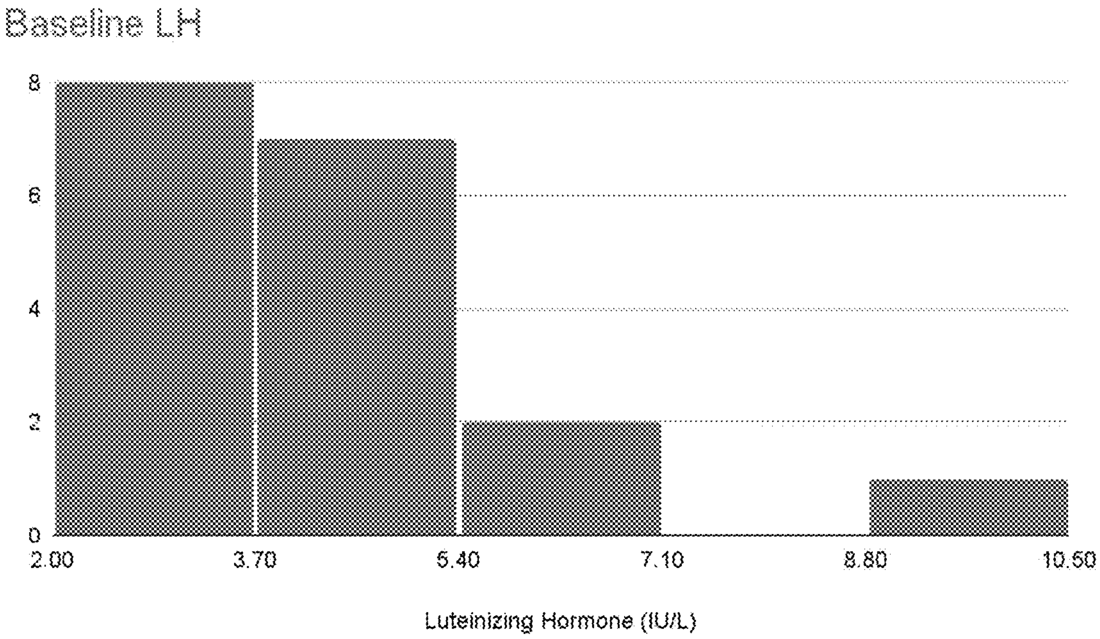
FIG. 19 is a graph of baseline LH levels prior to administration of 800 mg testosterone, 30 g fat, and 3.125 mg, 6.25 mg, or 12.5 mg enclomiphene.
Figure 20:
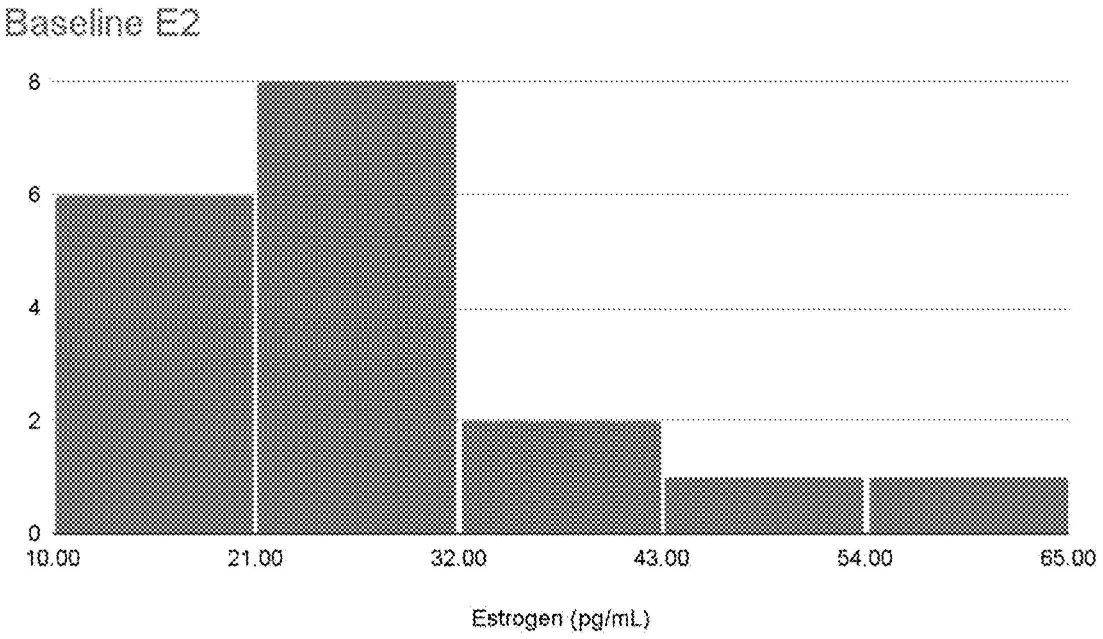
FIG. 20 is a graph of baseline E2 levels prior to administration of 800 mg testosterone, 30 g fat, and 33.125 mg, 6.25 mg, or 12.5 mg enclomiphene.
Figure 21:
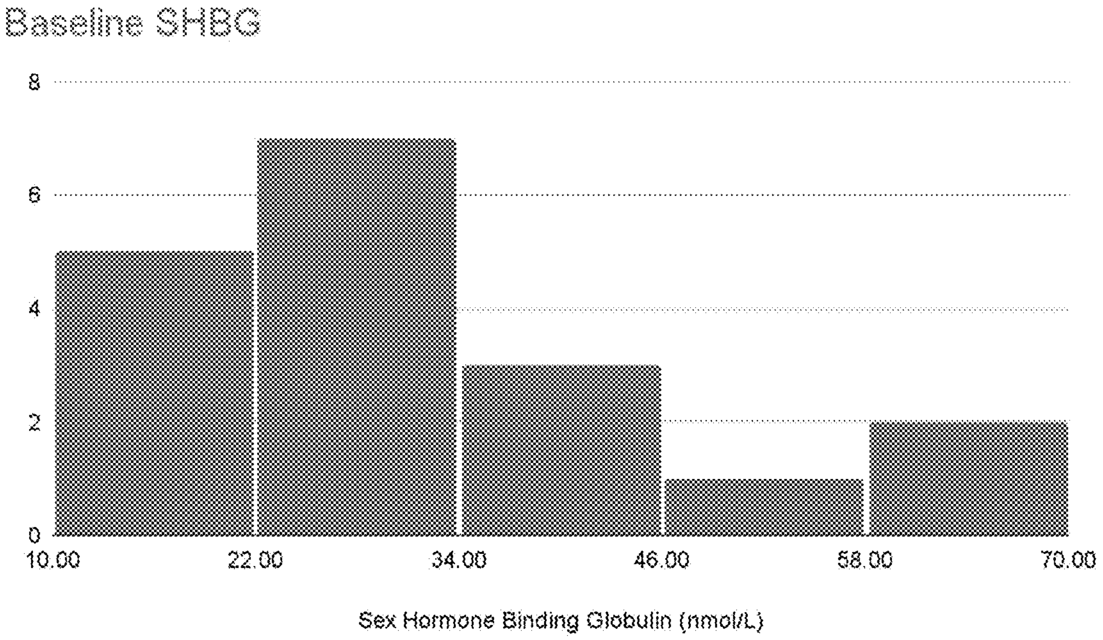
FIG. 21 is a graph of baseline SHBG levels prior to administration of 800 mg testosterone, 30 g fat, and 3.125 mg, 6.25 mg, or 12.5 mg enclomiphene.
Figure 22:
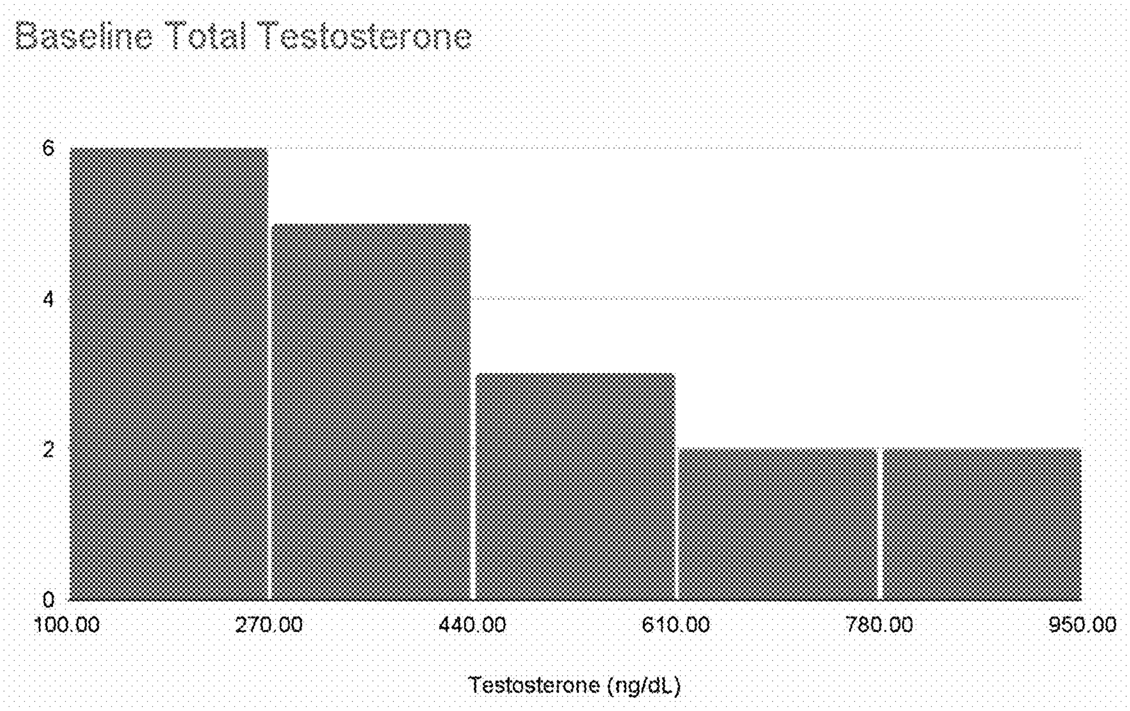
FIG. 22 is a graph of baseline total testosterone levels prior to administration of 800 mg testosterone, 30 g fat, and 3.125 mg, 6.25 mg, or 12.5 mg enclomiphene.
Figure 23:
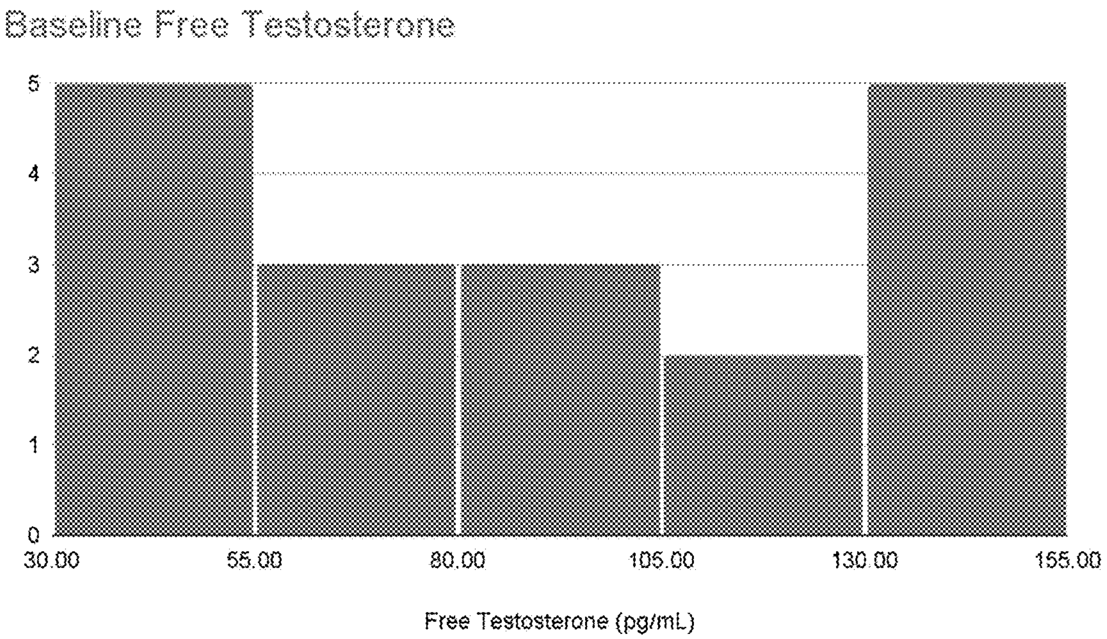
FIG. 23 is a graph of baseline free testosterone levels prior to administration of 800 mg testosterone, 30 g fat, and 3.125 mg, 6.25 mg, or 12.5 mg enclomiphene.
Figure 24:
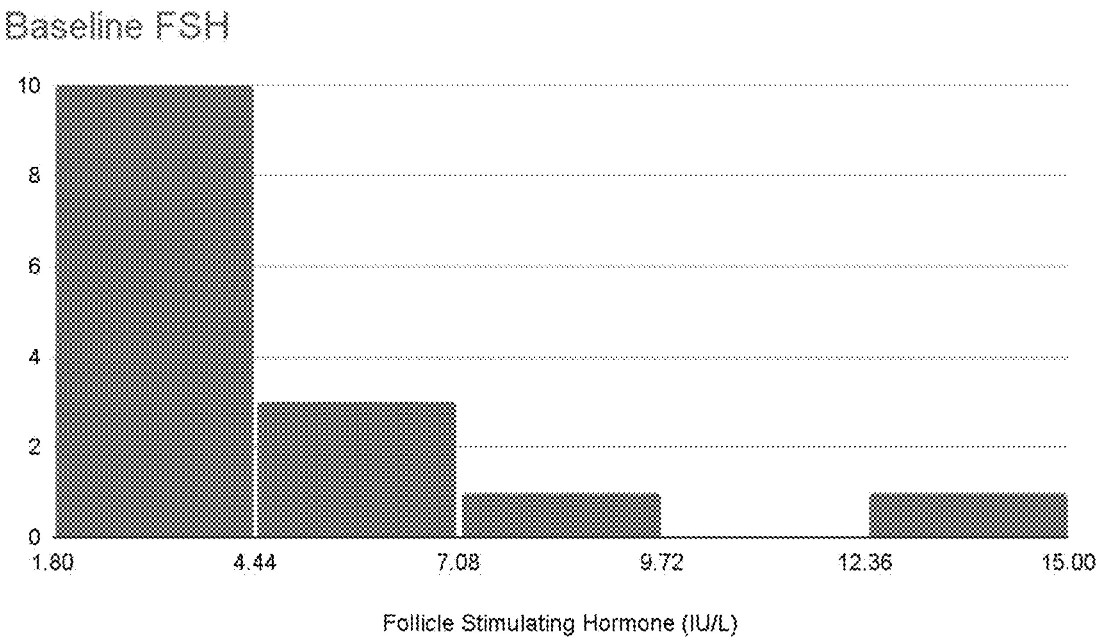
FIG. 24 is a graph of baseline FSH levels prior to administration of 800 mg testosterone, 30 g fat, and 3.125 mg, 6.25 mg, or 12.5 mg enclomiphene.
Figure 25:
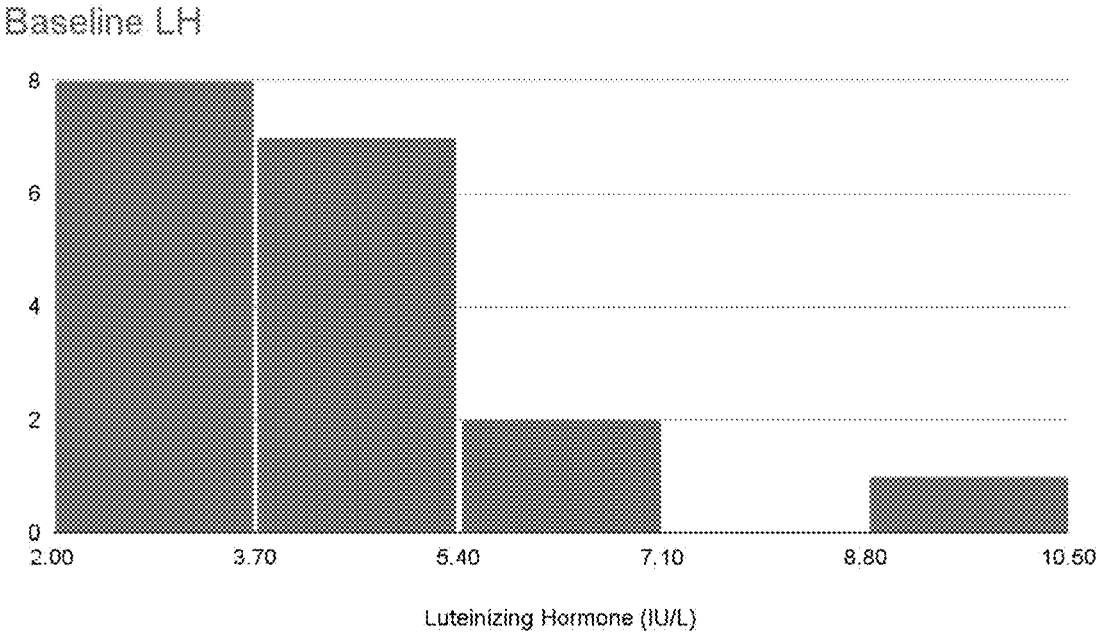
FIG. 25 is a graph of baseline LH levels prior to administration of 800 mg testosterone, 30 g fat, and 3.125 mg, 6.25 mg, or 12.5 mg enclomiphene.
Figure 26:
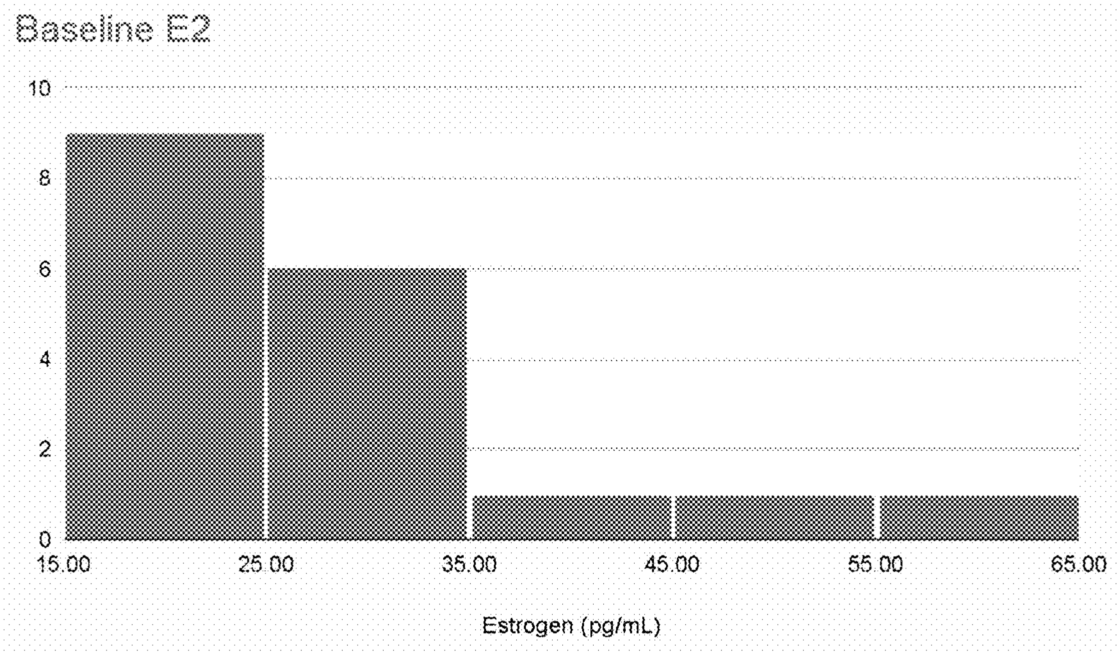
FIG. 26 is a graph of baseline E2 levels prior to administration of 800 mg testosterone, 30 g fat, and 33.125 mg, 6.25 mg, or 12.5 mg enclomiphene.
Figure 27:
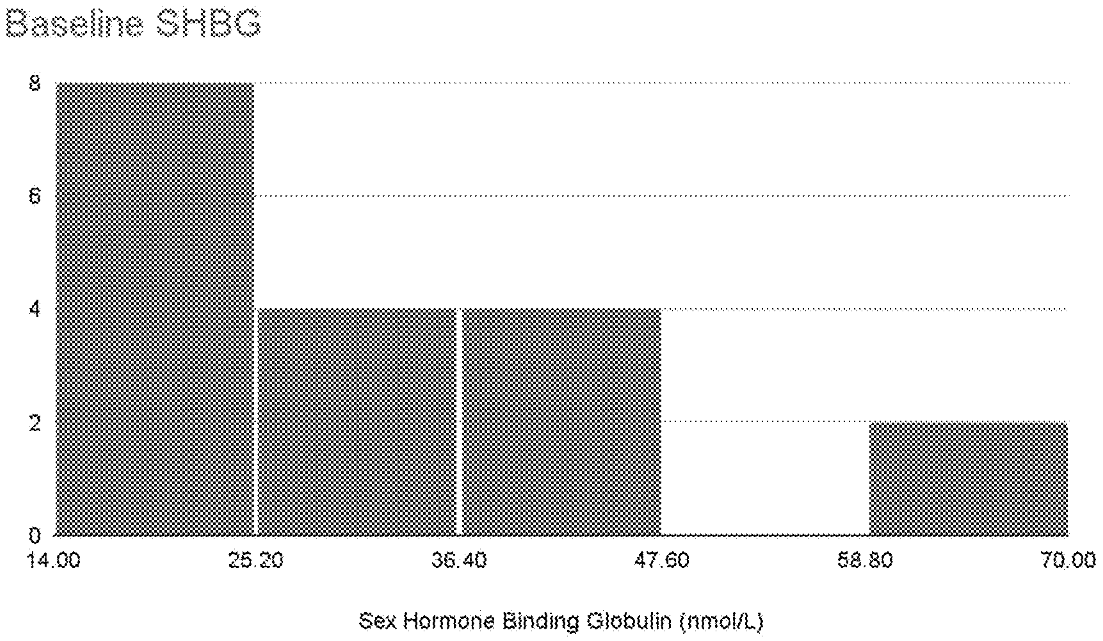
FIG. 27 is a graph of baseline SHBG levels prior to administration of 800 mg testosterone, 30 g fat, and 3.125 mg, 6.25 mg, or 12.5 mg enclomiphene.
Figure 28:
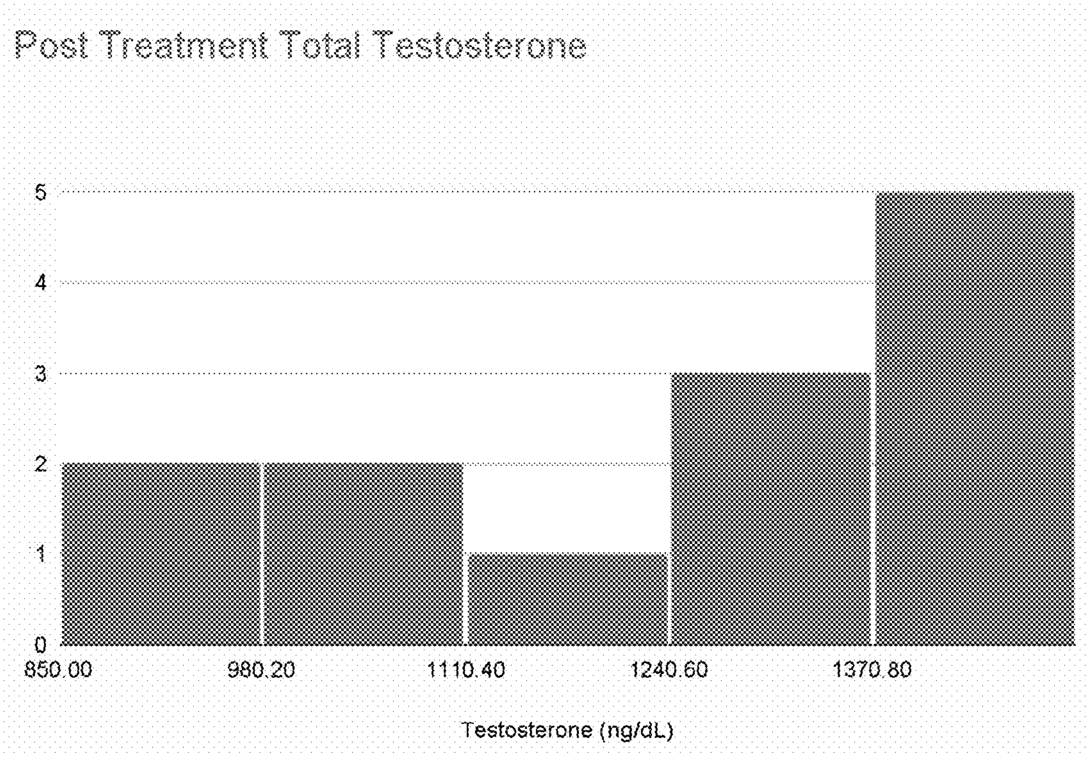
FIG. 28 is a graph of total testosterone levels after administration of 800 mg testosterone, 30 g fat, and 3.125 mg, 6.25 mg, or 12.5 mg enclomiphene.
Figure 29:
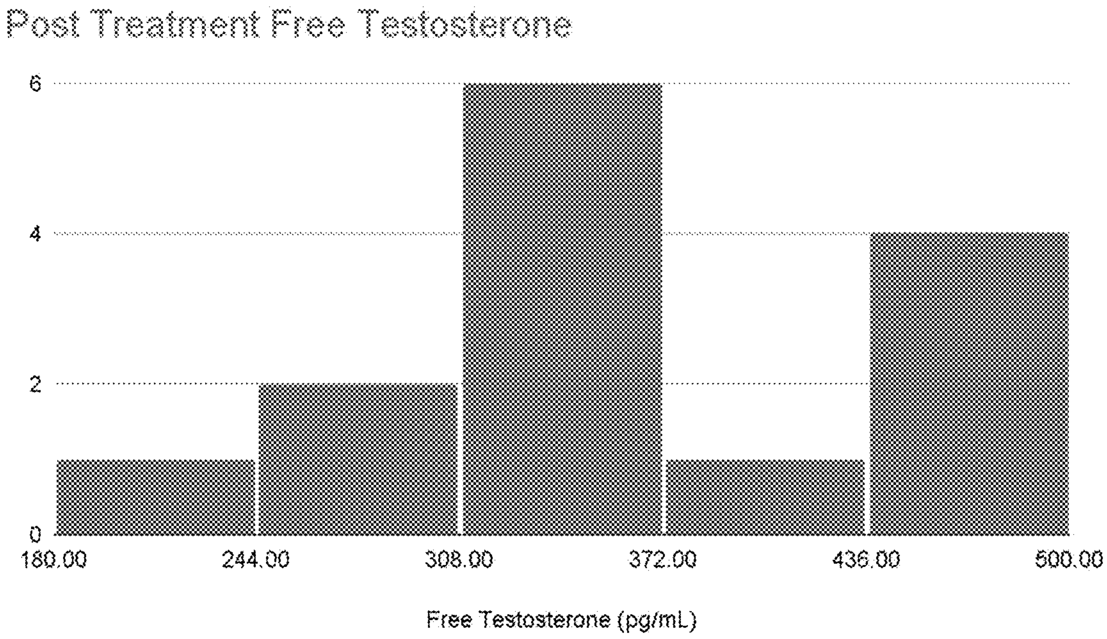
FIG. 29 is a graph of free testosterone levels after administration of 800 mg testosterone, 30 g fat, and 3.125 mg, 6.25 mg, or 12.5 mg enclomiphene.
Figure 30:
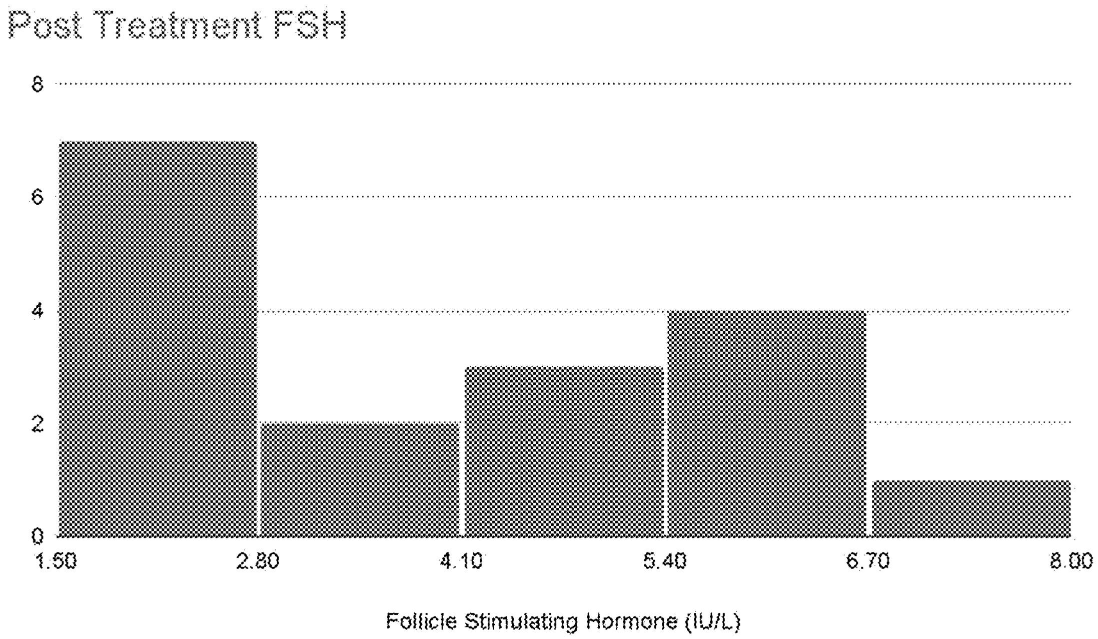
FIG. 30 is a graph of FSH levels after administration of 800 mg testosterone, 30 g fat, and 3.125 mg, 6.25 mg, or 12.5 mg enclomiphene.
Figure 31:
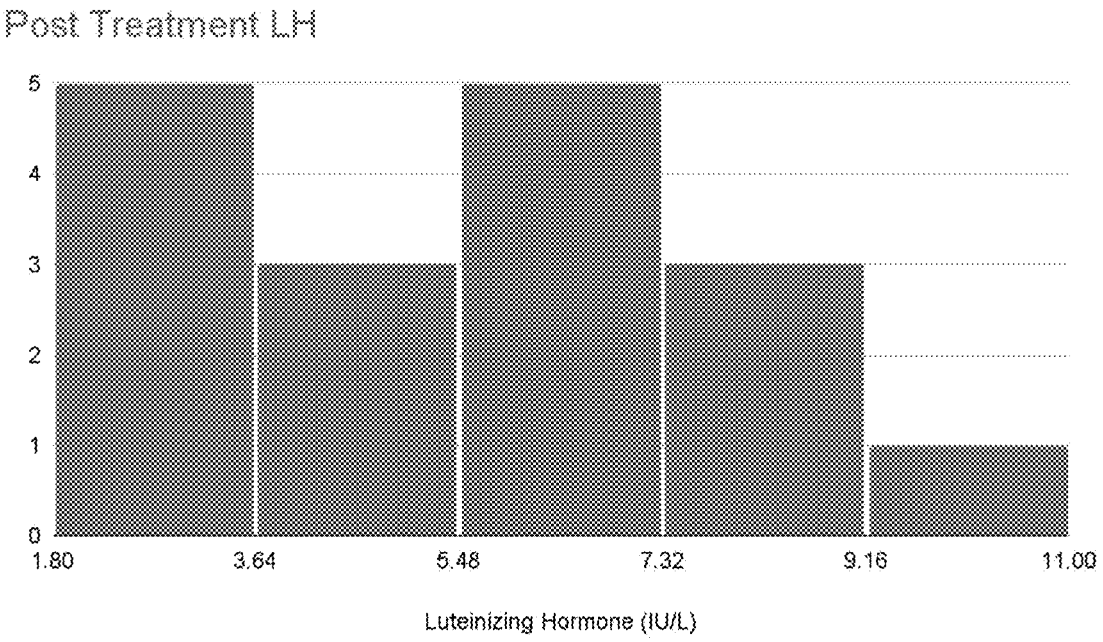
FIG. 31 is a graph of LH levels after administration of 800 mg testosterone, 30 g fat, and 3.125 mg, 6.25 mg, or 12.5 mg enclomiphene.
Figure 32:
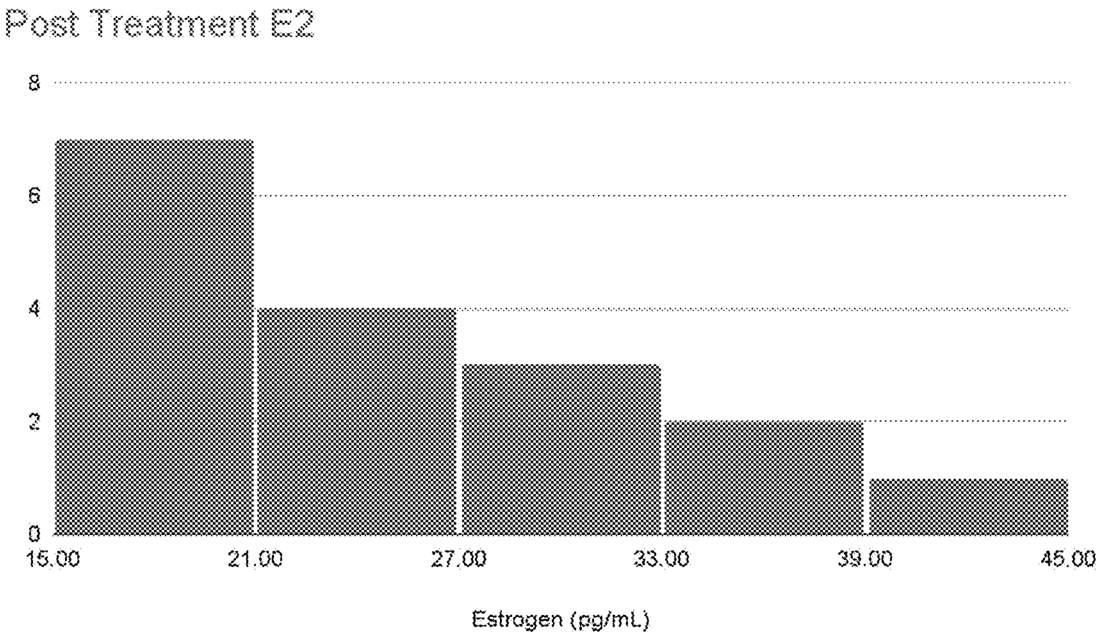
FIG. 32 is a graph of E2 levels after administration of 800 mg testosterone, 30 g fat, and 3.125 mg, 6.25 mg, or 12.5 mg enclomiphene.
Figure 33:
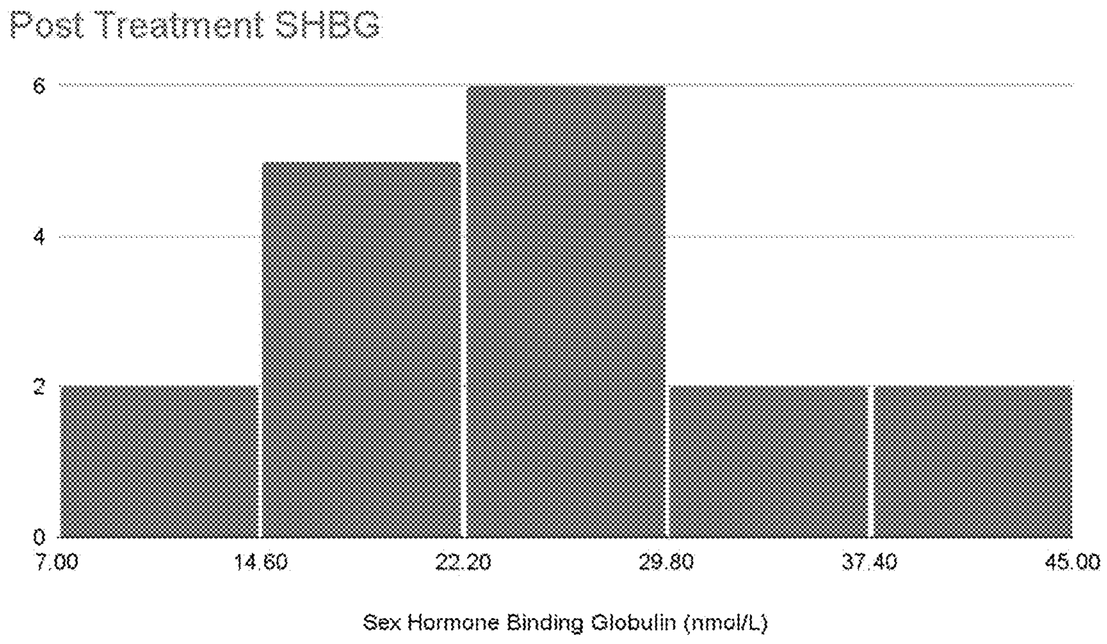
FIG. 33 is a graph of SHBG levels after administration of 800 mg testosterone, 30 g fat, and 3.125 mg, 6.25 mg, or 12.5 mg enclomiphene.

Hormone levels were measured before and after co-administration of 200-600 mg of testosterone, 30 g of fat (included for optimal lymphatic absorption), and 3.125 mg, 6.25 mg, or 12.5 mg of enclomiphene. See FIGS. 4 to 9 for baseline hormone levels. Testosterone concentration was measured at +4 hours. Testosterone, LH, and FSH levels showed that the 200-600 mg doses of testosterone were less effective at consistently elevating testosterone levels compared to the standardized 800 mg dose of testosterone (see Table 15, n=24). See FIGS. 2 and 3 for compiled post treatment hormone levels for examples 10 to 13.

TABLE 15

Hormone levels at +4 hours after 200-600 mg of testosterone + 30 g of fat + 3.125 mg, 6.25 mg, or 12.5 mg enclomiphene

| Parameter | Mean (SD) | Change from Baseline | Average Relative Change from Baseline | p-value |
|---|---|---|---|---|
| Total T (ng/dL) | | | | |
| Baseline | 442.0 (238.1) | | | |
| Post Treatment | 856.6 (311.1) | 414.6 | 169.40% | $p < 0.025$ |
| Free T (pg/mL) | | | | |
| Baseline | 91.4 (42.4) | | | |
| Post Treatment | 232.3 (99.3) | 140.9 | 227.20% | $p < 0.025$ |
| LH (IU/L) | | | | |
| Baseline | 4.3 (1.9) | | | |
| Post Treatment | 7.0 (4.9) | 2.7 | 76.90% | $p < 0.025$ |
| FSH (IU/L) | | | | |
| Baseline | 4.9 (3.2) | | | |
| Post Treatment | 5.4 (8.8) | 0.5 | 13.20% | $p = 0.1$ |
| E2 (pg/mL) | | | | |
| Baseline | 26.1 (11.2) | | | |
| Post Treatment | 27.5 (8.3) | 1.4 | 15.90% | $p = 0.19$ |
| SHBG (nmol/L) | | | | |
| Baseline | 32.5 (16.1) | | | |
| Post Treatment | 26.3 (9.9) | −6.2 | −10.60% | $p < 0.025$ |

Example 11: TRT with 800 mg Testosterone+3.125 mg, 6.25 mg, or 12.5 mg Enclomiphene (+4 Hours, Fasting)

This example investigated the anti-suppressive properties of a SERM (enclomiphene) after administration of oral testosterone and enclomiphene under fasted conditions.

Hormone levels were measured before and after co-administration of 800 mg of testosterone and 3.125 mg, 6.25 mg, or 12.5 mg of enclomiphene. See FIGS. 10 to 15 for baseline hormone levels. Testosterone concentration was measured at +4 hours. Testosterone, LH, and FSH levels showed that testosterone levels might have been artificially elevated due to the protocol instructing participants to eat only 1 hour after dosing. Participants who reported fasting for over 3 hours post-dosing had on average testosterone levels below 600 ng/dL, indicating the substantial impact of fasting and the timing of fat consumption on treatment efficacy (see Table 16, n=19). See FIGS. 2 and 3 for compiled post treatment hormone levels for examples 10 to 13.

TABLE 16

Hormone levels at +4 hours after 800 mg of testosterone + 3.125 mg, 6.25 mg, or 12.5 mg enclomiphene (fasting)

| Parameter | Mean (SD) | Change from Baseline | Average Relative Change from Baseline | p-value |
|---|---|---|---|---|
| Total T (ng/dL) | | | | |
| Baseline | 437.5 (2.0) | | | |
| Post Treatment | 1099.1 (372.6) | 661.6 | 262.9% | $p < 0.025$ |
| Free T (pg/mL) | | | | |
| Baseline | 88.5 (43.8) | | | |
| Post Treatment | 309.3 (130.6) | 220.8 | 377.6% | $p < 0.025$ |
| LH (IU/L) | | | | |
| Baseline | 4.2 (2.0) | | | |
| Post Treatment | 5.9 (2.3) | 1.7 | 71.1% | $p < 0.025$ |
| FSH (IU/L) | | | | |
| Baseline | 4.5 (3.0) | | | |
| Post Treatment | 4.4 (2.1) | 0.1 | 9.7% | $p = 0.29$ |
| E2 (pg/mL) | | | | |
| Baseline | 27.3 (12.1) | | | |
| Post Treatment | 24.6 (8.3) | −2.7 | −0.5% | $p = 0.68$ |
| SHBG (nmol/L) | | | | |
| Baseline | 55.0 (15.8) | | | |
| Post Treatment | 25.3 (9.3) | −29.7 | −14.4% | $p < 0.025$ |

Example 12: TRT with 800 mg Testosterone+30 g Fat+3.125 mg, 6.25 mg, or 12.5 mg Enclomiphene (+1 Hour)

This example investigated the anti-suppressive properties of a SERM (enclomiphene) after administration of oral testosterone, fat, and enclomiphene.

Hormone levels were measured before and after co-administration of 800 mg of testosterone, 30 g of fat, and 3.125 mg, 6.25 mg, or 12.5 mg of enclomiphene. See FIGS. 16 to 21 for baseline hormone levels. Testosterone concentration was measured at +1 hour. Testosterone, LH, and FSH levels showed lower increases in testosterone levels compared to the 4-hour tests. Total testosterone increased by an average of 415.4 ng/dL (182.1% relative change), and free testosterone increased by an average of 135.5 pg/mL (240.3% relative change) (see Table 17, n=18). See FIGS. 2 and 3 for compiled post treatment hormone levels for examples 10 to 13.

TABLE 17

Hormone levels at +1 hour after 800 mg of testosterone + 30 g of fat + 3.125 mg, 6.25 mg, or 12.5 mg enclomiphene

| Parameter | Mean (SD) | Change from Baseline | Average Relative Change from Baseline | p-value |
|---|---|---|---|---|
| Total T (ng/dL) | | | | |
| Baseline | 441.7 (269.4) | | | |
| Post Treatment | 857.1 (297.8) | 415.4 | 182.1% | $p < 0.025$ |
| Free T (pg/mL) | | | | |
| Baseline | 84.1 (41.9) | | | |
| Post Treatment | 219.6 (80.0) | 135.5 | 240.3% | $p < 0.025$ |
| LH (IU/L) | | | | |
| Baseline | 3.8 (1.4) | | | |
| Post Treatment | 6.8 (3.5) | 3.0 | 91.6% | $p < 0.025$ |
| FSH (IU/L) | | | | |
| Baseline | 4.1 (1.5) | | | |
| Post Treatment | 4.8 (1.9) | 0.7 | 23.9% | $p = 0.028$ |

TABLE 17-continued

| Parameter | Mean (SD) | Change from Baseline | Average Relative Change from Baseline | p-value |
|---|---|---|---|---|
| Hormone levels at +1 hour after 800 mg of testosterone + 30 g of fat + 3.125 mg, 6.25 mg, or 12.5 mg enclomiphene | | | | |
| E2 (pg/mL) | | | | |
| Baseline | 28.2 (12.0) | | | |
| Post Treatment | 20.7 (5.3) | −7.5 | −18.5% | p = 0.998 |
| SHBG (nmol/L) | | | | |
| Baseline | 35.8 (18.1) | | | |
| Post Treatment | 26.1 (10.9) | −9.7 | −16.4% | p < 0.025 |

Example 13: TRT with 800 mg Testosterone+30 g Fat+3.125 mg, 6.25 mg, or 12.5 mg Enclomiphene (+4 Hours)

This example investigated the anti-suppressive properties of a SERM (enclomiphene) after administration of oral testosterone, fat, and enclomiphene.

Hormone levels were measured before and after co-administration of 800 mg of testosterone, 30 g of fat, and 3.125 mg, 6.25 mg, or 12.5 mg of enclomiphene. See FIGS. 22 to 27 for baseline hormone levels and FIGS. 28 to 33 for post treatment hormone levels. Testosterone concentration was measured at +4 hours. Total testosterone increased by an average of 865.5 ng/dL (307.6% relative change), free testosterone increased by an average of 295 pg/mL (470.1% relative change), and LH and FSH levels remained within clinically normal ranges for all subjects post treatment (clinically normal range for LH is 1 IU/L or more and clinically normal range for FSH is 1 IU/L or more) (see Table 18, n=18). The maintenance of LH and FSH levels within clinically normal ranges demonstrated the efficacy of enclomiphene in preventing hormonal suppression after the administration of oral testosterone. See FIGS. 2 and 3 for compiled post treatment hormone levels for examples 10 to 13.

TABLE 18

| Parameter | Mean (SD) | Change from Baseline | Average Relative Change from Baseline | p-value |
|---|---|---|---|---|
| Hormone levels at +4 hour after 800 mg of testosterone + 30 g of fat + 3.125 mg, 6.25 mg, or 12.5 mg enclomiphene | | | | |
| Total T (ng/dL) | | | | |
| Baseline | 462.1 (256.6) | | | |
| Post Treatment | 1327.6 (223.4) | 865.5 | 307.6% | p < 0.025 |
| Free T (pg/mL) | | | | |
| Baseline | 88.0 (39.8) | | | |
| Post Treatment | 383.0 (87.3) | 295 | 470.1% | p < 0.025 |
| LH (IU/L) | | | | |
| Baseline | 3.8 (1.4) | | | |
| Post Treatment | 6.1 (3.5) | 2.3 | 69% | p < 0.025 |
| FSH (IU/L) | | | | |
| Baseline | 4.0 (1.5) | | | |
| Post Treatment | 4.4 (1.8) | 0.4 | 16.2% | p = 0.26 |
| E2 (pg/mL) | | | | |
| Baseline | 27.4 (12.3) | | | |
| Post Treatment | 22.7 (8.1) | −4.7 | −7.1% | p = 0.964 |

TABLE 18-continued

| Parameter | Mean (SD) | Change from Baseline | Average Relative Change from Baseline | p-value |
|---|---|---|---|---|
| Hormone levels at +4 hour after 800 mg of testosterone + 30 g of fat + 3.125 mg, 6.25 mg, or 12.5 mg enclomiphene | | | | |
| SHBG (nmol/L) | | | | |
| Baseline | 36.8 (17.4) | | | |
| Post Treatment | 27.1 (10.5) | −9.7 | −18.9% | p < 0.025 |

Example 14: Left-Tailed Wilcoxon Test for Example 12 and Example 13 Estradiol Measurements The Shapiro-Wilk test was used to assess the variability in distribution characteristics across different parameters for examples 12 and 13. The statistical analysis indicated that baseline total testosterone (Total T) and baseline free testosterone (Free T) were normally distributed, while other parameters such as luteinizing hormone (LH), follicle-stimulating hormone (FSH), estradiol (E2), and sex hormone-binding globulin (SHBG) deviated from a normal distribution.

The Wilcoxon signed-rank test, a non-parametric method for analyzing changes from baseline to post-treatment across all variables, was used. Statistical analysis results showed high p-values, close to 1, in the right-tailed Wilcoxon tests, along with a noticeable decrease in estrogen levels (18.5% estrogen level decrease in example 12 and 7.1% estrogen level decrease in example 13). This prompted a reevaluation of the current estrogen approach.

A left-tailed Wilcoxon test was used to determine if the observed decrease in estrogen levels was statistically significant for results. The left-tailed Wilcoxon test confirmed that the observed decrease in estrogen levels was statistically significant (see Table 19).

TABLE 19

| Parameter | Mean (SD) | Change from Baseline | Average Relative Change from Baseline | p-value |
|---|---|---|---|---|
| Left-tailed Wilcoxon test | | | | |
| (Example 12) E2 (pg/mL) | | | | |
| Baseline | 26.8 (12.1) | | | |
| Post Treatment | 20.1 (5.3) | −6.7 | −18.5% | p < 0.025 |
| (Example 13) E2 (pg/mL) | | | | |
| Baseline | 27.4 (12.3) | | | |
| Post Treatment | 22.7 (8.1) | −4.7 | −7.1% | p < 0.025 |

Example 15: TRT with 100 mg of Topical Testosterone+Oral Enclomiphene

This Example investigated the anti-suppressive properties of an oral SERM (enclomiphene) after administration of topical testosterone.

Forty-five male patients were administered 100 mg of topical testosterone with enclomiphene. Several patients had previously been administered injectable testosterone without enclomiphene support, resulting in severely suppressed baseline gonadotropin levels. During the experiment, patients initially received 6.25 mg of enclomiphene with 100 mg topical testosterone. However, only one patient (2.2%) maintained LH and FSH levels above the normal thresholds of 1 IU/L and 1 IU/L, respectively. Upon increasing the enclomiphene dosage, 12.5 mg was effective at maintaining LH and FSH above the normal thresholds for 28 patients (62.2%), while the remaining 17 patients (37.8%) required the higher 25 mg dose to achieve optimal results, as shown in Table 22 below.

The data presented in Tables 20 and 21 below demonstrate that even after long periods of being suppressed by previous testosterone therapy, patients who were administered at least 12.5 mg of enclomiphene along with 100 mg of topical testosterone showed remarkable improvement in gonadotropin function. The testosterone, LH, and FSH levels of all 45 patients remained elevated above baseline, showing continued success at preventing suppression.

For example, one patient presented with initial LH/FSH values of 0.3/0.3 IU/L and a trough testosterone level of 431 ng/dL while administered injectable testosterone. After switching to topical testosterone and enclomiphene, his LH/FSH levels rose significantly to 23.7/27.9 IU/L, and his total testosterone reached 851 ng/dL.

TABLE 20

Average Hormone Values at Different Enclomiphene Doses with 100 mg Topical Testosterone

| Parameter | Baseline (Pre-Treatment) | 6.25 mg Enclomiphene | 12.5-25 mg Enclomiphene |
|---|---|---|---|
| LH (IU/L) | 6.56 | 0.71 | 7.26 |
| FSH (IU/L) | 5.06 | 1.29 | 6.38 |
| SHBG (nmol/L) | 39.56 | 36.28 | 42.72 |
| Estradiol (pg/mL) | 19.99 | 24.34 | 30.73 |
| Free Testosterone (pg/mL) | 85.91 | 265.34 | 271.69 |
| Total Testosterone (ng/dL) | 459.16 | 1190.88 | 1210.22 |

TABLE 21

Average Changes in Hormone Levels from Baseline

| Parameter | Change with 6.25 mg Enclomiphene | Change with 12.5-25 mg Enclomiphene |
|---|---|---|
| LH (IU/L) | −5.85 (−89.2%) | 0.70 (+10.7%) |
| FSH (IU/L) | −3.77 (−74.5%) | 1.32 (+26.1%) |
| SHBG (nmol/L) | −3.28 (−8.3%) | 3.16 (+8.0%) |
| Estradiol (pg/mL) | 4.35 (+21.8%) | 10.74 (+53.7%) |
| Free Testosterone (pg/mL) | 179.43 (+208.9%) | 185.78 (+216.3%) |
| Total Testosterone (ng/dL) | 731.72 (+159.4%) | 751.06 (+163.6%) |

TABLE 22

Enclomiphene Dosage Distribution and Effectiveness

| Enclomiphene Dose | Number of Patients | Percentage | LH/FSH Above Threshold |
|---|---|---|---|
| 6.25 mg | 45 | 100% | 1 patient (2.2%) |
| 12.5 mg | 28 | 62.20% | 28 patients (100%) |
| 25 mg | 17 | 37.80% | 17 patients (100%) |
| Total at optimal dose | 45 | 100% | 45 patients (100%) |

Example 16: TRT with 200 mg of Topical Testosterone+Oral Enclomiphene

This Example investigated the anti-suppressive properties of an oral SERM (enclomiphene) after administration of topical testosterone.

One male patient was administered 200 mg of topical testosterone daily with 50 mg of oral enclomiphene every other day. The data presented in Table 23 demonstrated that a patient who was administered 50 mg of enclomiphene every other day along with 200 mg of topical testosterone daily maintained LH and FSH levels above 1 U/mL with elevated testosterone levels.

TABLE 23

Average Changes in Hormone Levels from Baseline

| Parameter | Baseline (Pre-Treatment) | Pre-Application (Day 1) | 4 Hours Post-Application (Day 1) | 12 Hours Post-Application (Day 1) | Pre-Application (Day 2) | 4 Hours Post-Application (Day 2) | 12 Hours Post-Application (Day 2) |
|---|---|---|---|---|---|---|---|
| Free Testosterone (pg/mL) | 76.8 | 92.8 | 294 | 302 | 53.2 | 300 | 281 |
| Total Testosterone (ng/dL) | 408 | 620 | 1500 | 1500 | 376 | 1500 | 1461 |
| Vitmin D | 38 | 85 | 87 | 81 | 89 | 88 | 86 |
| LH (IU/L) | 5.7 | 3.2 | 2.4 | 2.2 | 3.1 | 2.3 | 2.1 |
| FSH (IU/L) | 4.1 | 1.7 | 1.7 | 1.5 | 1.9 | 1.8 | 1.7 |
| E2 (pg/mL) | 19 | 22 | 29.6 | 39 | 24.2 | 22.9 | 29.5 |
| SHBG (nmol/L) | 37.8 | 53.2 | 56.6 | 54.4 | 56.2 | 54.9 | 57.2 |
| Prolactin (ng/mL) | 20.5 | — | — | — | — | — | — |
| ALT (IU/L) | 16 | 23 | 23 | 23 | 23 | 25 | 26 |
| PSA | 0.4 | 0.6 | 0.5 | 0.5 | 0.6 | 0.5 | 0.6 |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of increasing testosterone levels in a subject in need thereof, comprising:

(i) administering to the subject an oral or sublingual tablet or capsule comprising about 5 mg to about 80 mg of enclomiphene citrate, clomiphene citrate, or toremifene citrate; and (ii) topically administering to the subject about 50 mg to about 400 mg of testosterone base or testosterone ester, wherein administering the oral or sublingual tablet or capsule and topically administering testosterone base or testosterone ester maintains a subject's LH level and FSH level at about 1 IU/L or more, or increases a subject's LH level and FSH level to about 1 IU/L or more.

2. The method of claim 1, wherein the oral or sublingual tablet or capsule is a sublingual tablet.

3. The method of claim 1, wherein the oral or sublingual tablet or capsule comprises enclomiphene citrate.

4. The method of claim 3, wherein the oral or sublingual tablet or capsule comprises about 5 mg to about 80 mg of enclomiphene citrate.

5. The method of claim 4, wherein the oral or sublingual tablet or capsule comprises about 6.25 mg, about 12.5 mg, about 25 mg, or about 50 mg of the enclomiphene citrate.

6. The method of claim 1, wherein the oral or sublingual tablet or capsule comprises clomiphene citrate.

7. The method of claim 6, wherein the oral or sublingual tablet or capsule comprises about 5 mg to about 80 mg of clomiphene citrate.

8. The method of claim 1, wherein the oral or sublingual tablet or capsule comprises toremifene citrate.

9. The method of claim 8, wherein the oral or sublingual tablet or capsule comprises about 5 mg to about 120 mg of toremifene citrate.

10. The method of claim 1, wherein the subject is topically administered about 50 mg to about 200 mg of testosterone base or testosterone ester.

11. The method of claim 1, wherein the subject is a human subject and administering the oral or sublingual tablet or capsule and topically administering testosterone base or testosterone ester increases the subject's total testosterone level by at least about 50% compared to the subject's baseline total testosterone level.

12. A method of increasing testosterone levels in a subject in need thereof, comprising administering to the subject:

(i) about 5 mg to about 250 mg of enclomiphene citrate, clomiphene citrate, or toremifene citrate; and (ii) about 50 mg to about 400 mg of testosterone base or testosterone ester, wherein at least the testosterone base or testosterone ester is administered topically or transdermally, wherein administering enclomiphene citrate, clomiphene citrate, or toremifene citrate and testosterone base or testosterone ester maintains a subject's LH level and FSH level at about 1 IU/L or more, or increases a subject's LH level and FSH level to about 1 IU/L or more.

13. The method of claim 12, wherein the subject is topically administered testosterone base or testosterone ester.

14. The method of claim 13, wherein the subject is topically administered about 50 mg to about 400 mg of testosterone base or testosterone ester daily.

15. The method of claim 14, wherein the subject is topically administered about 50 mg to about 200 mg of testosterone base or testosterone ester daily.

16. The method of claim 12, wherein the subject is topically administered enclomiphene citrate.

17. The method of claim 16, wherein the subject is topically administered about 5 mg to about 150 mg per day of enclomiphene citrate.

18. The method of claim 12, wherein the subject is topically administered clomiphene citrate.

19. The method of claim 18, wherein the subject is topically administered about 5 mg to about 150 mg per day of clomiphene citrate.

20. The method of claim 12, wherein the subject is topically administered toremifene citrate.

21. The method of claim 20, wherein the subject is topically administered about 5 mg to about 240 mg per day of toremifene citrate.

22. The method of claim 12, wherein the enclomiphene citrate, clomiphene citrate, or toremifene citrate is administered orally or sublingually.

23. The method of claim 12, wherein the subject is transdermally administered testosterone base or testosterone ester.

24. The method of claim 12, wherein the subject is transdermally administered enclomiphene citrate, clomiphene citrate, or toremifene citrate.

25. The method of claim 24, wherein the subject is transdermally administered enclomiphene citrate.

26. The method of claim 12, wherein the enclomiphene citrate, clomiphene citrate, or toremifene citrate is administered as a first topical or transdermal composition and the testosterone is administered as a second topical or transdermal composition.

27. The method of claim 12, wherein the enclomiphene citrate, clomiphene citrate, or toremifene citrate and the testosterone is administered as a topical or transdermal composition.

28. The method of claim 12, wherein the enclomiphene citrate, clomiphene citrate, or toremifene citrate and the testosterone are administered by a transdermal patch.

29. The method of claim 12, wherein the subject is a human subject and administering the therapeutically effective amount of enclomiphene citrate, clomiphene citrate, or toremifene citrate and the therapeutically effective amount of testosterone base or testosterone ester increases the subject's total testosterone level by at least about 50% compared to the subject's baseline total testosterone level.

* * * * *